United States Patent
Bang et al.

(10) Patent No.: US 10,087,484 B2
(45) Date of Patent: Oct. 2, 2018

(54) METHOD FOR SYNTHESIZING GENE USING HIGH-DEPTH OLIGONUCLEOTIDE TILING

(71) Applicant: UNIVERSITY-INDUSTRY FOUNDATION, YONSEI UNIVERSITY, Seoul (KR)

(72) Inventors: Duhee Bang, Seoul (KR); Nam Jin Cho, Seoul (KR); Han Na Seo, Seoul (KR); Eui Jin Kwon, Seoul (KR)

(73) Assignee: UNIVERSITY-INDUSTRY FOUNDATION, YONSEI UNIVERSITY (KR)

( * ) Notice: Subject to any disclaimer, the term of this patent is extended or adjusted under 35 U.S.C. 154(b) by 238 days.

(21) Appl. No.: 15/184,805

(22) Filed: Jun. 16, 2016

(65) Prior Publication Data

US 2016/0369335 A1   Dec. 22, 2016

(30) Foreign Application Priority Data

Jun. 17, 2015 (KR) .................. 10-2015-0085940
Jun. 16, 2016 (KR) .................. 10-2016-0074949

(51) Int. Cl.
| | |
|---|---|
| *C12Q 1/68* | (2018.01) |
| *C12N 15/10* | (2006.01) |
| *C12P 19/34* | (2006.01) |
| *C12Q 1/6874* | (2018.01) |
| *C12Q 1/6806* | (2018.01) |
| *C12Q 1/6834* | (2018.01) |

(52) U.S. Cl.
CPC ....... *C12Q 1/6874* (2013.01); *C12N 15/1031* (2013.01); *C12P 19/34* (2013.01); *C12Q 1/6806* (2013.01); *C12Q 1/6834* (2013.01)

(58) Field of Classification Search
None
See application file for complete search history.

(56) References Cited

U.S. PATENT DOCUMENTS

2015/0329854 A1* 11/2015 Bang .................. C12N 15/102
506/17

FOREIGN PATENT DOCUMENTS

KR   1020140075635   6/2014

OTHER PUBLICATIONS

Bang et al. "Gene synthesis by circular assembly amplification" 5(1) Nature Methods 37-39 (Nov. 25, 2007).*
First Office Action for KR application No. 10-2016-0074949, dated May 16, 2017, 6 pages.
Yoon et al., "microDuMIP: target-enrichment technique for microarray-based duplex molecular inversion probes", Nucleic Acids Research, 2015, vol. 43, No. 5, 9 pages.
Kosuri et al. "A Scalable Gene Synthesis Platform Using High-Fidelity DNA Microchips", Nat Biotechnol. Dec. 2010; 28(12):1295-1299.
Kim "Shotgun DNA synthesis for the high-throughput construction of large DNA molecules", Nucleic Acids Research, 2012, vol. 40, No. 18: 1-8.
Schwartz et al. "Accurate gene synthesis with tag-directed retrieval of sequence-verified DNA molecules", Nat Methods, Sep. 2012; 9(9): 913-915.
Matzas et al. "Next Generation Gene Synthesis by targeted retrieval of bead-immobilized, sequence verified DNA clones from a high throughput pyrosequencing device", Nat Biotechnol. Dec. 2010; 28(12): 1291-1294.

* cited by examiner

*Primary Examiner* — Nancy J Leith
(74) *Attorney, Agent, or Firm* — Swanson & Bratschun, L.L.C.

(57) ABSTRACT

Provided is a method for stably synthesizing an error-free gene using a high-depth oligonucleotide tiling, which includes designing an oligonucleotide fragment by an over-overlapping method, synthesizing the oligonucleotide fragment using DNA microarray, retrieving error-free oligonucleotide fragments retrieved by next generation sequencing, and assembling the error-free oligonucleotide fragments.

7 Claims, 3 Drawing Sheets

Specification includes a Sequence Listing.

[FIG. 1]
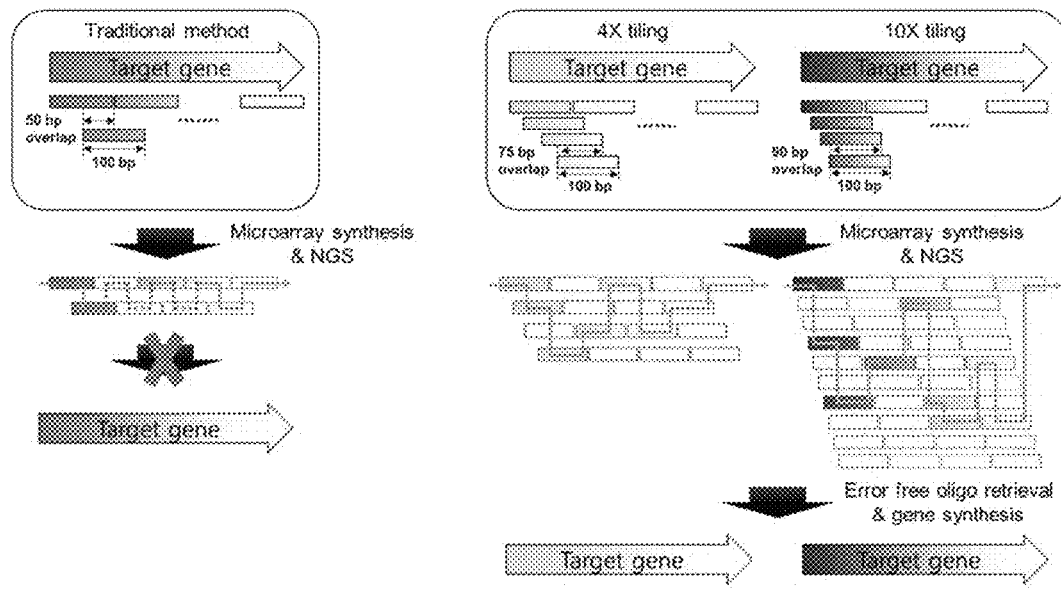
[FIG. 2]
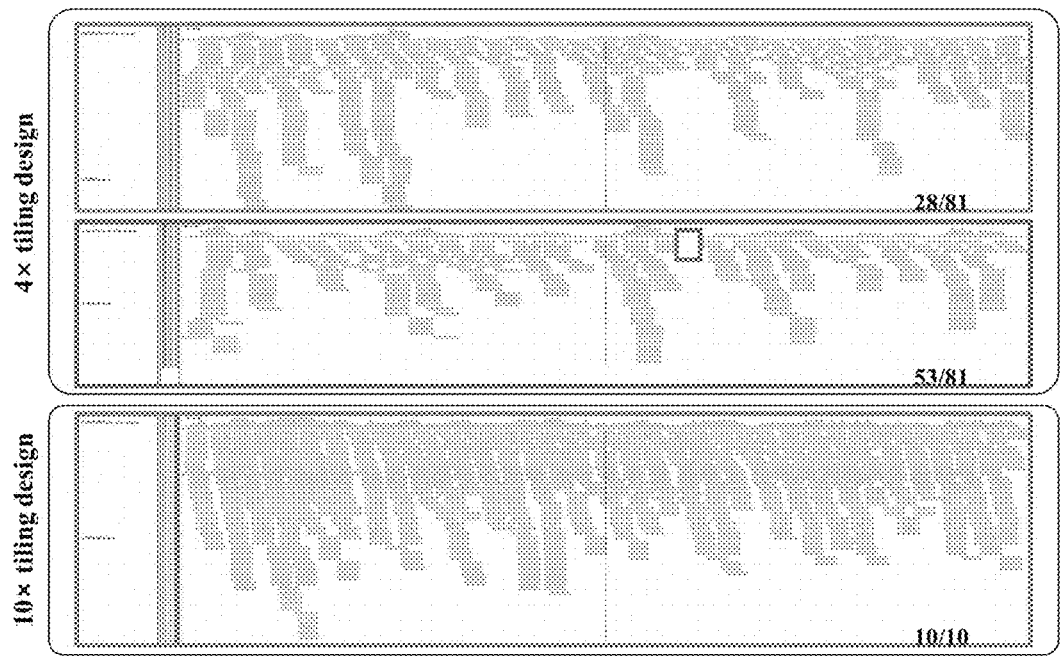

[FIG. 3]
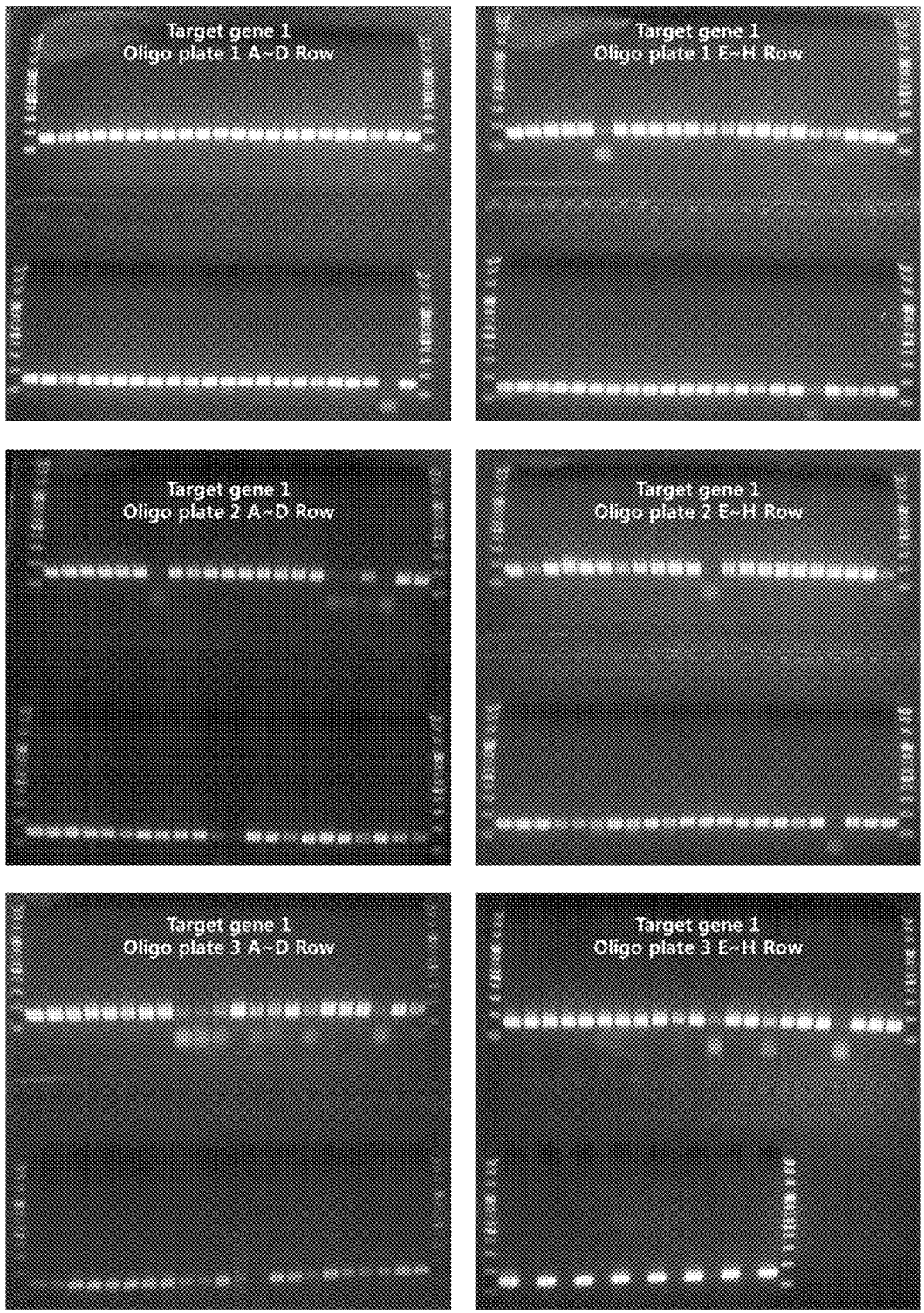

[FIG. 4]
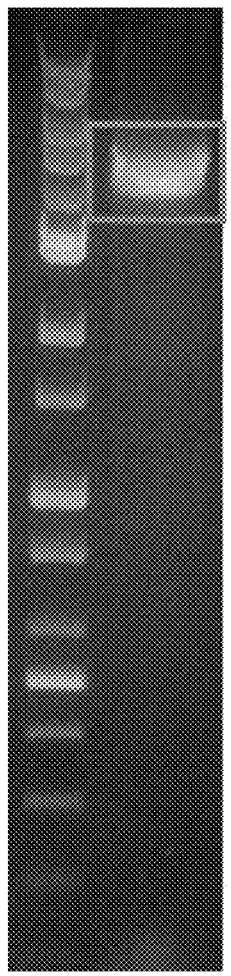

METHOD FOR SYNTHESIZING GENE USING HIGH-DEPTH OLIGONUCLEOTIDE TILING

CROSS-REFERENCE TO RELATED APPLICATIONS

This application claims priority to and the benefit of Korean Patent Application No. 2015-0085940, filed on Jun. 17, 2015, and Korean Patent Application No. 2016-0074949, filed on Jun. 16, 2016, the disclosure of which is incorporated herein by reference in its entirety.

SEQUENCE STATEMENT

Incorporated by reference herein in its entirety is the Sequence Listing entitled "0338-101-US_ST25.TXT" created Jun. 16, 2016, size of 177 kilobyte.

BACKGROUND

1. Field of the Invention

The present invention relates to a method for stably synthesizing a gene by a single microarray oligonucleotide synthesis process using a high-depth oligonucleotide tiling and a single process of selecting the synthesized oligonucleotide without an error based on next generation sequencing.

2. Discussion of Related Art

Generally, gene synthesis refers to technology for synthesizing a long nucleic acid fragment with a length difficult to be synthesized, or longer, by a general oligo synthesis technique (generally 200 nucleotides (hereinafter, referred to as nt)) by assembling short nucleic acid fragments, that is, an oligonucleotide (hereinafter, referred to as an "oligo"). Gene synthesis is essential technology for biology-related research, and may be used in protein engineering, genome engineering, biochemical production, etc. The gene synthesis process generally includes designing an oligo fragment that will be used in gene synthesis, synthesizing the designed oligo fragment, assembling synthesized oligo fragments, and screening a sequence of a gene synthesized without an error through sequencing of the synthesized gene.

First, to design oligos for synthesizing a gene, fragmentation of a base sequence of the gene to be synthesized may be performed. Here, each of the fragmented oligos is designed to have a region overlapping adjacent oligos, wherein the region is used in the following assembly process. Here, an overlapped length of the oligo fragment is generally designed to be half of the total oligo length or less and thus minimize the number of the oligo fragments.

Generally, an oligo fragment for synthesizing a gene is chemically synthesized using one oligo in one column Since the synthesis efficiency in this process is not 100%, the synthesized oligos include a mixture of an oligo synthesized in a desired shape and an oligo having an undesired sequence. Errors generated in this process are generally errors introduced in the gene synthesis, and play a critical role in allowing the process of screening an error-free gene sequence to be labor-intensive. Also, since a cost for the synthesis of the oligo fragment using a column is very high, a considerable amount of the cost required for gene synthesis is consumed in this process.

As a method for assembling an oligo, assembly PCR, ligase chain reaction (LCR) or Gibson assembly may be used. It is confirmed if deletion, insertion or substitution has occurred in the genes assembled by the above-described method by comparison with sequences that were synthesized, by base sequence analysis. To this end, a base sequence is analyzed by cloning the gene, followed by Sanger sequencing. This process is very labor-intensive, and requires a high cost.

There have been many attempts to solve the limitations of such conventional gene synthesis technology, which are a high oligo synthesis cost and a labor-intensive process for analyzing a base sequence. First, an attempt used a method for synthesizing an oligo fragment required for gene synthesis through the DNA microarray synthesis technology. According to DNA microarray synthesis technology, several tens of thousands of oligo fragments can be simultaneously synthesized at low cost, and therefore the cost for synthesizing an oligo fragment can be reduced. According to microarray synthesis technology, since the synthesized oligo fragments are present in a mixture in one tube, and the amount of the synthesized oligo fragments is too small to be used in gene synthesis, flanking sequences are placed at both ends of the synthesized oligo fragments to selectively amplify desired sequences, and then the amplified sequences are utilized in gene synthesis (Kosuri S et al. *Nat Biotechnol.* vol. 28(12), pp. 1295-9 (2010, Nov. 28)). However, since the oligo fragments synthesized by the microarray method have a higher error rate than a conventional oligo synthesized in a column, there is a difficulty in screening a sequence of the gene synthesized without an error.

The second attempt combined recently-developed next generation sequencing technology to the gene synthesis technology. Recently, many types of next generation sequencing methods (Illumina, Ion Torrent, 454, PACBIO, etc.) enable analysis of a large number of nucleic acid fragments at one time, but have not been applied to identify a base sequence of a gene for longer than a length which is able to be sequenced due to short sequencing length (Illumina: 300 base pairs, Ion Torrent: 200 base pairs, 454: 500 base pairs) or a high sequencing error rate (PACBIO: 15%). To solve such a labor-intensive process, research on applying a retrieved oligo fragment synthesized without an error or a DNA fragment to subsequent gene synthesis, after a base sequence is analyzed by next generation sequencing for synthesized oligo fragments or assembled DNA fragments prior to synthesis of a final gene, was presented [Kim, et al. *Nucleic Acids Res.* vol. 40(18), e140 (2012.10); Schwartz et al. *Nature Methods*, vol. 9(9), pp. 913-5(2012.09)]. However, when a DNA library is amplified, a PCR bias phenomenon occurs such that, instead of each of the sequences present in the library being uniformly amplified, specific sequences are excessively amplified, compared with other sequences. For this reason, it is impossible to retrieve all of the oligo fragments designed and synthesized at one time through a single process of DNA microarray synthesis and a single process of next generation sequencing, and repetition of DNA microarray synthesis and next generation sequencing is required until all oligo fragments are obtained.

SUMMARY OF THE INVENTION

The present invention is directed to providing a method for stably synthesizing a gene without an error using microarray nucleic acid synthesis technology and next generation sequencing technology.

In one aspect, the present invention provides a method for synthesizing a gene, comprising:

dividing a target nucleic acid sequence into base sequence sections of a predetermined length, forming a tiling oligonucleotide set in which each base sequence section is overlapped 3 to 100 times, each oligonucleotide of the tiling oligonucleotide set being designed by an over-overlapping method to overlap 66.7% to 99% of the total length of one another, and include 1 to 33.3% of the base sequence of an adjacent base sequence section, and designing an oligonucleotide fragment by placing flanking sequences including the same or different Type IIS restriction enzyme recognition sequences at both ends of each oligonucleotide of the tiling oligonucleotide set;

synthesizing and amplifying the oligonucleotide fragment using a DNA microarray and retrieving the oligonucleotide synthesized without an error by next generation sequencing (NGS); and eliminating the flanking sequences at both ends of the error-free oligonucleotide, sequentially mixing and assembling tiling oligonucleotide sets from which the flanking sequences are eliminated according to an adjoining sequence, or mixing and assembling the tiling oligonucleotide sets at one time.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a schematic diagram illustrating a traditional oligo designing method for gene synthesis and an oligo designing method using an over-overlapping method of the present invention;

FIG. 2 is a distribution diagram of oligos retrieved after next generation sequencing for oligos in 4× and 10× tiling designs by an over-overlapping method of the present invention;

FIG. 3 illustrates results of amplifying oligos synthesized without an error after being retrieved by over-overlapping and next generation sequencing of the present invention; and FIG. 4 illustrates results of synthesizing a gene using oligos synthesized without an error after being retrieved by over-overlapping and next generation sequencing of the present invention.

DETAILED DESCRIPTION OF EXEMPLARY EMBODIMENTS

The term "nucleotide" used herein is DNA or RNA present in a single-stranded or double-stranded form, and may include an analog thereof.

The term "amplification reaction" used herein refers to a reaction of amplifying a target nucleic acid sequence, and may be performed by polymerase chain reaction (PCR). PCR includes reverse transcription PCR (RT-PCR), multiplex PCR, real-time PCR, assembly PCR, fusion PCR, and ligase chain reaction (LCR), but the present invention is not limited thereto.

The term "primer" used herein refers to an oligonucleotide, which is single-stranded, may include a ribonucleotide, and preferably, a deoxyribonucleotide. The primer is hybridized or annealed to one part of a template, thereby forming a double-stranded structure. The primer may be hybridized or annealed to a flanking sequence of the present invention. The annealing refers to apposition of an oligonucleotide or a nucleic acid to a template nucleic acid, and the apposition refers to formation of a nucleic acid molecule complementary to a template nucleic acid or a part thereof by polymerizing nucleotides using a polymerase. The hybridization refers to formation of a duplex structure by pairing two single-stranded nucleic acids with complementary base sequences. The primer may serve as a starting point of synthesis under conditions for inducing the synthesis of an elongated product of the primer complementary to a template.

The term "flanking sequence" used herein refers to a sequence present at an end of an oligonucleotide, which may serve as a priming position for amplifying the amount of the oligonucleotide and may be used as an annealing position of a primer set during amplification, and the flanking sequence may be present at an end of a restriction enzyme recognition sequence or may include a restriction enzyme recognition sequence.

The term "complementary" used herein refers to having complementarity to an extent such that selective hybridization to the above-described nucleotide sequence is enabled under specific hybridization or annealing conditions.

The term "assembly of oligonucleotides" used herein refers to aligning and merging nucleic acid fragments using complementary base sequences for linkage thereof to form longer nucleic acid fragments.

Hereinafter, a configuration of the present invention will be described in detail.

The present invention relates to a method for synthesizing a gene, which includes: dividing a target nucleic acid sequence into base sequence sections of a predetermined length, forming a tiling oligonucleotide set in which each base sequence section is overlapped 3 to 100 times, each oligonucleotide of the tiling oligonucleotide set being designed by over-overlapping method to overlap 66.7% to 99% of the total length of one another, and include 1 to 33.3% of the base sequence of an adjacent base sequence section, and designing an oligonucleotide fragment by placing flanking sequences including the same or different Type IIS restriction enzyme recognition sequences at both ends of each oligonucleotide of the tiling oligonucleotide set; synthesizing and amplifying the oligonucleotide fragment using a DNA microarray and retrieving the oligonucleotide synthesized without an error by next generation sequencing (NGS); and eliminating the flanking sequences at both ends of the error-free oligonucleotide, sequentially mixing and assembling tiling oligonucleotide sets from which the flanking sequences are eliminated according to an adjoining sequence, or mixing and assembling the tiling oligonucleotide sets at one time.

Conventionally, an oligo fragment was designed for a designed oligo to be fully overlapped or partially overlapped by adjacent oligos present at both ends, and the method for synthesizing a gene of the present invention is to design an oligo by an over-overlapping method to have overlapping parts between adjacent oligos placed at both ends of the designed oligo.

Also, the oligo designed by the over-overlapping method is synthesized using a DNA microarray, an oligo synthesized without an error is identified and retrieved by next-generation sequencing and then assembled, thereby enabling simultaneous synthesis of a gene.

The process of designing an oligo fragment using the over-overlapping method will be described in detail with reference to FIG. 1.

The over-overlapping method used in the present invention may use 3× to 100× tiling designs. For example, when 4× or 10× tiling designs is used, for the 4× tiling design, a gene region to be synthesized is designed to be overlapped four times, and for the 10×tiling design, a gene region to be synthesized is designed to be overlapped 10 times. The term "tiling oligonucleotide set" or "tiling oligo set" used herein is used interchangeably. In the 4× tiling design, the tiling oligo set comprises four types of oligos, and in the 10×tiling design, the tiling oligo set comprises 10 types of oligos. Each oligo of the tiling oligo set is designed by an over-overlapping method, and for example, when a target nucleic acid sequence is divided into a base sequence section of a predetermined length (length: 100 bp), the 4× tiling design is 100 nt in length. The length of the first oligo is 100 nt, the second oligo is designed to overlap 75 nt of the first oligo, the third oligo overlaps 50 nt of the first oligo and 75 nt of the second oligo, the fourth oligo overlaps 25 nt of the first oligo, 50 nt of the second oligo, and 75 nt of the third oligo. Here, the second to fourth oligos include a region partially overlapping the base sequence of an adjacent base sequence section. That is, the second oligo has a sequence corresponding to 75 nt of the first oligo, and corresponding to 25 nt of the base sequence of an adjacent base sequence section. The third oligo has a sequence corresponding to 50 nt of the first oligo, and corresponding to 50 nt of the base sequence of an adjacent base sequence section. The fourth oligo has a sequence corresponding to 25 nt of the first oligo, and corresponding to 75 nt of the base sequence of an adjacent base sequence section.

In short, oligos of the tiling oligo set may have the same length as the divided base sequence section, overlap 66.7% to 99% of the total length of one another, and include 1 to 33.3% of the base sequence of an adjacent base sequence section.

Also, in the target nucleic acid sequence, a total number of the oligos used for synthesis may be calculated by Equation 1.

Total number of oligos={(Length of target nucleic acid sequence to be synthesized−Length of fragment (or base sequence section))/(Length of oligo/$n$)}+1     [Equation 1]

In this equation, n is the number of overlapping oligos.

Accordingly, for the 3× tiling design, when a target nucleic acid sequence is 3550 bp, and a fragment length is 100 bp, an oligo length is the same as the fragment length, and since n is 3, when n is substituted to Equation 1, the 3× tiling design consists of 104.5 (approximately 105) oligos.

The 4× tiling design consists of 139 oligos, the 10×tiling design consists of 346 oligos, and the 100×tiling design consists of 3451 oligos.

In the method for synthesizing a gene of the present invention, the target nucleic acid sequence is divided into base sequence sections of a predetermined length to design the tiling oligonucleotide set, and may be expressed as a fragment or gene region. The base sequence sections may be sorted into those with a length of 100 to 1000 bp, but may be suitably sorted according to the length of the target nucleic acid sequence. Thus, the present invention is not particularly limited.

Since the base sequence section is designed to have the same length as the oligo, the length of the oligo may also be in the above-described range.

Meanwhile, each oligo of the tiling oligo set is designed to include a flanking sequence which includes the same or different Type IIS restriction enzyme recognition sequences at both ends and is used as a priming position for amplification after oligo synthesis. The restriction enzyme recognition sequence enables the assembly of an error-free oligo by simultaneously cutting off the flanking sequences placed at the ends.

The flanking sequence may be 20 to 50 bp, or 20 to 30 bp in length, and the length of the restriction enzyme recognition sequence may be changed according to a type of a restriction enzyme.

The restriction enzyme recognition sequence may be a Type IIS restriction enzyme, which may be, for example, EarI, BsaI, BsmBI, BtsI or AarI. In further detail, the restriction enzyme recognition sequence may be a BsaI type IIS recognition sequence.

The target nucleic acid sequence may be a base sequence with a size of a gene or genome. An oligo may be synthesized based on a target nucleic acid sequence to be synthesized using a DNA microarray.

In the method for synthesizing a gene of the present invention, the oligo fragment may be an oligo for a DNA microarray. As a method for synthesizing an oligo on the microarray, an inkjet printing method, a photolithography array method, or an electrochemical array method may be used, but the present invention is not limited thereto. The synthesis of the oligo may be performed by a conventional oligo synthesis method.

The oligo fragment may be amplified using a primer for a complementary flanking sequence from the flanking sequences placed at both ends, which serve as priming positions. The amplification may use a conventionally known amplification reaction, which may be PCR.

Next generation sequencing is performed to check if errors are generated at the amplified oligo fragments.

Here, for the next generation sequencing, adaptor sequences may be placed at both ends of the amplified product.

Linking of the adaptor sequences may be performed by PCR assembly or by ligation, but the present invention is not limited thereto. In an exemplary embodiment of the present invention, the adaptor sequence may be a 454 adaptor sequence.

The next generation sequencing may employ conventional technology.

A method for selectively retrieving an error-free oligo from the oligo fragments undergoing the next generation sequencing may include amplifying the synthesized oligonucleotide, placing a barcode sequence with a length of 15 to 20 nt, designed with any one among A, T, G or C between an oligonucleotide sequence and an adaptor sequence placed at both ends of an amplified product and retrieving a desired oligonucleotide through selective amplification by PCR in this region used as a priming position [Kim, et al. *Nucleic Acids Res.* vol. 40(18), e140 (2012.10); Schwartz et al. *Nature methods*, vol. 9(9), pp. 913-5 (2012, September)] or directly and selectively retrieving a desired oligonucleotide by a physical method [Matzas, et al. *Nature biotechnology*, vol. 28(12), pp. 1291-4 (2010, December)].

Although error-free oligos with respect to all of the synthesized sequence are not retrieved by a single process of next generation sequencing reaction, a partially-overlapping region is present between oligos adjacent to an unretrieved oligo, and thus gene synthesis can be stably performed.

The retrieved error-free oligos are amplified using the flanking sequences placed at both ends. The flanking sequences are digested from the amplified oligos with a restriction enzyme, and the oligos are assembled, thereby synthesizing an error-free gene.

The error-free oligos may be assembled by sequentially mixing the tiling oligo sets from which the flanking sequences present at both ends are eliminated according to an adjoining sequence, or simultaneously mixing the tiling oligo sets.

The assembly may employ any one of Gibson assembly, assembly PCR, fusion PCR and LCR, but the present invention is not limited thereto.

A size of the assembled gene (or DNA) may be 1000 to 10,000 bp, preferably, 2,000 to 7,000 bp, and more preferably, 3,000 to 5,000 bp.

The method for synthesizing a gene of the present invention may further include cloning the assembled gene in a desired expression vector, and verifying a base sequence of the synthesized gene.

Technology for cloning the assembled gene may use a known genetic engineering method without limitation.

Hereinafter, the present invention will be described in detail with reference to examples. However, the following examples are merely to explain the present invention, and the scope of the present invention is not particularly limited to the following examples.

EXAMPLE 1

Design and Synthesis of Oligo Fragments

A desired target nucleic acid sequence was Cas9-clustered regulatory interspaced short palindromic repeats (CRISPR; 3,550 bp), and synthesized, targeting 81 different species-derived genes. In detail, for a 4× tiling design, a nucleic acid sequence set forth in SEQ ID NO:1 was used, and for a 10×tiling design, a nucleic acid sequence set forth in SEQ ID NO:2 was used.

Oligo fragments were designed as shown in FIG. 1. In the 4× tiling design, to synthesize the desired target nucleic acid sequence (3,550 bp), a total of 139 tiling oligos were designed. Each of the oligos designed as described above was designed to overlap 75 bp of an immediately adjacent oligo, 50 bp of a second adjacent oligo, and 25 bp of a third adjacent oligo. Accordingly, the oligo fragment is formed in a structure of a target nucleic acid sequence of 100 bp, and a flanking sequence of 20 bp and a BsaI Type IIS restriction enzyme recognition sequence of 6 bp, placed at both ends of the target nucleic acid sequence, and thereby has a sequence of a total of 152 bp (SEQ ID NOs: 3 to 141).

For the 10× tiling design, a total of 346 tiling oligos were designed, and each of the oligos was designed to overlap 90 bp of an immediately adjacent oligo, 80 bp of a second adjacent oligo, and 70 bp of a third adjacent oligo (SEQ ID NOs: 142 to 487). Accordingly, like the 4× tiling design, the oligo fragment is formed in a structure of a the target nucleic acid sequence of 100 bp, and a flanking sequence of 20 bp and a BsaI Type IIS restriction enzyme recognition sequence of 6 bp present at both ends of the target nucleic acid sequence, and thereby has a sequence of a total of 152 bp (SEQ ID NOs: 142 to 487).

The oligo fragment designed as described above was synthesized using an electrochemical array.

EXAMPLE 2

Amplification of Oligo Fragment

The synthesized oligos were amplified by PCR with a pair of flanking primers with respect to the flanking sequences present at both ends of the oligo. The PCR was performed by initial denaturation at 98° C. for 3 minutes, and 20 cycles of reaction at 98° C. for 30 seconds, 58° C. for 30 seconds, and 72° C. for 30 seconds, and final elongation at 72° C. for 10 minutes. A reaction solution was prepared by adding 25 μl of a KAPA library amplification kit (Master mix), 16 μl of distilled water, 4 μl of a 10 μM forward primer, 4 μl of a 10 μM reverse primer, and 1 μl of an oligo pool as a template, and adjusted to a total volume of 50 μl. The amplified oligonucleotides were identified and separated through electrophoresis on a 1.5% agarose gel, and a DNA band of 152 bp was cut out and purified using a Qiagen mini elute gel purification kit.

EXAMPLE 3

Error Verification and Amplification of Oligo Fragment by Next Generation Sequencing Errors and coverage of the assembled type were verified by linking a 454 adaptor sequence to the amplified product purified in Example 2 through 454 sequencing. First, a primer including flanking sequences placed at both ends of the oligo fragment, an N20 sequence enabling to be used as a barcode later, and a 454 adaptor sequence was prepared. The 454 adaptor sequence was simply linked by amplifying the oligo fragment using the primer. A reaction solution was prepared by adding 25 μl of a KAPA library amplification kit master mix, 15 μl of distilled water, 4 μl of a 10 μM forward primer, 4 μl of a 10 μM reverse primer, and 2 μl of an oligo fragment for a total volume of 50 μl. The amplified oligo fragment was identified and isolated by electrophoresis on a 1.5% agarose gel, and a DNA band of 252 bp, to which 50 bp each of a 454 adaptor and a barcode sequence were linked to both ends, was cut off, and purified using a Qiagen mini elute gel purification kit. Thus, a product to which the 454 adaptor sequences were linked to both ends of the oligo fragment was able to be obtained. The product was analyzed by 454 sequencing.

FIG. 2 illustrates probability of assembly of a synthesized target nucleic acid sequence by aligning sequences of oligos synthesized without an error, obtained from the results of next generation sequencing, to the synthesized target nucleic acid sequence.

FIG. 3 illustrates results of amplification of retrieved error-free oligos.

For a 4× tiling design, a total of 12,247 oligos were designed and synthesized by an electrochemical array on a DNA microarray, and then oligos synthesized without an error with respect to 5,299 sequences were identified by next generation sequencing. However, there was no synthesizable gene among the 81 genes.

6948 sequences designed in a 4× tiling form, which were not obtained through the first microarray synthesis, and 3460 sequences designed in a 10× tiling form with respect to 10 genes were synthesized by an electrochemical array, and distribution of error-free oligos was confirmed by next generation sequencing.

As a result, in the sequences designed in the 4× tiling design, only 28 genes of the 81 genes were able to be synthesized despite two cycles of oligo synthesis and selection of error-free oligos, and in the remaining 53 sequences, there were parts that had not been secured yet.

However, for the 10× tiling design, oligos synthesized without an error to 2562 sequences were able to be secured, and a total of 10 genes were able to be synthesized using these oligos.

EXAMPLE 4

Cutting Off(Remove??) Flanking Sequences of Amplified Error-Free Oligo Fragment Using Restriction Enzyme 1 μg of an error-free oligo fragment retrieved in Example 3 was used in digestion with a restriction enzyme. As a BsaI restriction enzyme, a product manufactured by New England Biolabs was used. A reaction solution was prepared by adding 2 μl of a restriction enzyme, 2 μl of a CutSmart buffer, 1 to 10 μl (1 μg or more) of each oligo fragment, and distilled water, and adjusted to have the total volume of 20 Afterward, the solution was incubated for 3 hours at 37° C., electrophoresis was performed on a 3% agarose gel to identify and separate an amplified oligo fragment, a DNA band of 112 bp in which the flanking sequences at both ends were eliminated was cut off, and purified using a Qiagen mini elute gel purification kit.

EXAMPLE 5

Assembly of Cut-Off Oligo Fragment

Using the cut-off oligo fragments obtained in Example 4, an experiment of mixing and simultaneously assembling adjacent oligo fragments was performed. A process of assembling a gene was performed by assembly PCR.

The assembly PCR was performed by initial denaturation at 98° C. for 3 minutes, 10 cycles of reaction at 98° C. for 30 seconds, at 50° C. for 30 seconds, and at 72° C. for 30 seconds, and final elongation at 72° C. for 10 minutes. Here, a process of reducing a temperature from 98° C. to 50° C. was performed by decreasing a temperature by 0.1° C. per second. A reaction solution was prepared by adding 25 μl of a KAPA library amplification kit master mix and 25 μl of an oligo mixture as a template for a total volume of 50 μl.

The target synthesized sequence assembled as described above was amplified using a primer sequence placed at the end of the sequence.

The amplified PCR was performed by initial denaturation at 98° C. for 3 minutes, at 98° C. for 30 seconds, at 58° C. for 30 seconds, and at 72° C. for 30 seconds whenever the length of the synthesized sequence was over 500 bp. Reactions (e.g.: 1,200 bp: 90 sec, 3,550 bp: 240 sec) were repeated 15 cycles, and final elongation was performed at 72° C. for 10 minutes. Each reaction solution was prepared by adding 25 μl of a KAPA library amplification kit master mix, 16 μl of distilled water, 2 μl of a 10 μM forward primer, 2 μl of a 10 μM reverse primer, and 1 μl of an oligo pool as a template for a total volume to 50 μl.

FIG. 4 illustrates a gene assembled using error-free oligos, showing that a target nucleic acid sequence is successfully synthesized.

EXAMPLE 6

Computer Simulation

Computer simulation was performed to indirectly confirm how efficient gene synthesis using high-density designed oligos was, compared to when a gene was synthesized using oligos designed by a traditional method (2x tiling design).

To this end, a process of the experiment was assumed to go through the following steps:
1) Obtaining of oligos designed to synthesize a gene by DNA microarray synthesis
2) Base sequence analysis for the obtained oligos by next generation sequencing
3) Retrieval of oligos synthesized without an error using pulse laser system
4) Performing of gene synthesis
In the above process, gene synthesis efficiency was determined by a type of the oligo synthesized without an error in the base sequence analysis. Accordingly, the present inventors simulated the number of oligos synthesized without an error, which can be secured by next generation sequencing.

The simulation was performed by the following processes:
1) It was assumed that a length of the gene to be synthesized was 4000 bp, and flanking sequences were placed at both ends of a 100 bp sequence for gene synthesis.
2) It was assumed that an average error rate of the synthesized oligo was 100 bp/error, and the results secured by next generation sequencing were 70,000.
3) From the oligos designed for gene synthesis, 10,000 sequences were retrieved by allowing overlapping, using a random function.
4) Gene synthesis efficiency was calculated by analyzing the oligos retrieved as described above.
5) To increase reliability of such a result, the simulation was repeated 500 times.

A first condition for simulation is the change in gene library synthesis efficiency according to oligo density when the same number (10,000) of DNA sequences was analyzed by next generation sequencing.

The number of oligos designed to synthesize gene libraries were assumed to be 10,000, and when the oligos were designed under 2x, 4x, 5x, and 10x tiling conditions, gene library synthesis efficiencies were compared.

In the conventional 2x tiling design, a total of 126 genes were able to be designed to overlap 50 bp of adjacent oligos, using 10,000 oligos. In the 4x, 5x and 10x tiling designs, genes were designed to respectively overlap 75 bp, 80 bp and 90 bp of adjacent oligos. Also, 63, 51 and 25 genes were able to be designed using 10,000 oligos.

When gene synthesis efficiency for the tiling design was simulated, in the 2x tiling design, the number of assemblable genes was 0 (0%), and it was confirmed that, in the 4x, 5x and 10x tiling designs, on average, 25.7 (40.72%), 40.8 (79.99%) and 24.99 (99.96%) of genes could be respectively synthesized.

A second condition for simulation is the change in gene library synthesis efficiency according to oligo density and an error rate of the synthesized oligo, when the same number of genes is synthesized.

The number of genes to be synthesized under this condition was set to 20, and the error rate of the synthesized oligo was set from 40 to 120 bp/error. In addition, like the first simulation, when oligos were designed under 2x, 4x, 5x and 10x tiling conditions, synthesis efficiencies were calculated.

As the result of the simulation, in the 2x tiling design, even under the condition of 120 bp/error, which is a relatively low error rate, on average, the synthesis efficiency was approximately 2.5 (12.33%). However, in the 4x and 5x tiling, it was confirmed that the gene library synthesis efficiency was 90% or more at 75 and 61 bp/error, respectively. In the 10x tiling, it was confirmed that a gene library can be stably synthesized even at an error rate of 50 bp/error.

According to the results of a series of simulations, it was confirmed that, as the density of the oligo capable of being used in gene synthesis is increased, the gene library synthesis efficiency is increased.

TABLE 1

| Error rate | 2x | 4x | 5x | 10x |
|---|---|---|---|---|
| 40 | 0 | 8.73 | 19.64 | 29.77 |
| 43 | 0 | 20.23 | 39.58 | 56.3 |
| 46 | 0.03 | 35.52 | 57.7 | 76.42 |

TABLE 1-continued

| Error rate | 2× | 4× | 5× | 10× |
|---|---|---|---|---|
| 49 | 0.06 | 49.6 | 71.36 | 87.26 |
| 52 | 0.08 | 59.78 | 80.47 | 93.17 |
| 55 | 0.25 | 68.99 | 86.42 | 96.76 |
| 58 | 0.57 | 75.4 | 89.82 | 98.1 |
| 61 | 0.87 | 80.02 | 92.27 | 98.89 |
| 64 | 1.14 | 83.51 | 94.58 | 99.39 |
| 67 | 1.58 | 86.22 | 95.24 | 99.66 |
| 70 | 2.21 | 88.57 | 96.66 | 99.7 |
| 75 | 2.91 | 91.05 | 97.77 | 99.89 |
| 80 | 4.05 | 93.22 | 98.16 | 99.89 |
| 85 | 5.09 | 94.63 | 99.05 | 99.98 |
| 90 | 6.03 | 95.69 | 98.91 | 99.94 |
| 100 | 8 | 96.33 | 99.42 | 100 |
| 110 | 10.85 | 97.47 | 99.53 | 100 |
| 120 | 12.33 | 97.71 | 99.68 | 100 |

The present invention can provide technology capable of synthesizing an oligo by a single microarray process by designing oligos for synthesizing a gene to excessively overlap one another, retrieving error-free oligos by next generation sequencing, and stably synthesizing an error-free gene.

It would be understood by those of ordinary skill in the art that the above descriptions of the present invention are exemplary, and the exemplary embodiments disclosed herein can be easily modified into other specific forms without changing the technical spirit or essential features of the present invention. Therefore, it should be interpreted that the exemplary embodiments described above are exemplary in all aspects, and are not limitative.

What is claimed is:

1. A method for synthesizing a gene, comprising:
dividing a target nucleic acid sequence into base sequence sections of a predetermined length, forming a tiling oligonucleotide set in which each base sequence section is overlapped 3 to 100 times, each oligonucleotide of the tiling oligonucleotide set being designed by an over-overlapping method to overlap 66.7% to 99% of the total length of one another, and include 1 to 33.3% of a base sequence of an adjacent base sequence section, and designing an oligonucleotide fragment by placing flanking sequences including the same or different Type IIS restriction enzyme recognition sequences at both ends of each oligonucleotide of the tiling oligonucleotide set;
synthesizing and amplifying the oligonucleotide fragment using a DNA microarray and retrieving the oligonucleotide synthesized without an error by next generation sequencing (NGS); and
eliminating the flanking sequences at both ends of the error-free oligonucleotide, sequentially mixing and assembling adjacent tiling oligonucleotide sets from which the flanking sequences are eliminated, or mixing and assembling the tiling oligonucleotide sets at one time.

2. The method for claim 1, wherein the target nucleic acid sequence is a gene-or genome-sized base sequence.

3. The method for claim 1, wherein the flanking sequence at both ends of each oligonucleotide of the tiling oligonucleotide set has a length of 20 to 50 bp.

4. The method for claim 1, wherein the oligonucleotide synthesized without an error is subject to next generation sequencing to check if there is an error after the synthesized oligonucleotide is amplified and adaptor sequences are placed at both ends of an amplified product.

5. The method for claim 1, wherein the retrieving of the oligonucleotide synthesized without an error includes amplifying the synthesized oligonucleotide, placing a barcode sequence with a length of 15 to 20nt, designed with any one among A, T, G or C, between an oligonucleotide sequence and an adaptor sequence placed at the both ends of an amplified product, and retrieving a desired oligonucleotide through selective amplification by PCR in this region used as a priming position, or directly and selectively retrieving a desired oligonucleotide by a physical method.

6. The method for claim 1, wherein the gene assembly employs any one of Gibson assembly, assembly PCR, fusion PCR or ligase chain reaction (LCR).

7. The method for claim 1, further comprising:
verifying if a gene is synthesized by cloning the resulting product obtained from assembling tiling oligonucleotide sets in an expression vector.

* * * * *

SEQUENCE LISTING

```
<160> NUMBER OF SEQ ID NOS: 487

<210> SEQ ID NO 1
<211> LENGTH: 3550
<212> TYPE: DNA
<213> ORGANISM: Artificial Sequence
<220> FEATURE:
<223> OTHER INFORMATION: Cas theta - CRISPR(clustered regulatory
      interspaced short palindromic repeats)

<400> SEQUENCE: 1
agctcctggg caacgtgctg gttattgtgc tgtctcatca ttttggcaaa gaattcgcgg      60
ccgccaccat ggggggtct gaggtgggaa cagtaccagt gacctggcgc ttgggggttg     120
atgtcgggga gagaagcata gggcttgcag ccgtctccta tgaggaagac aagcccaaag    180
aaatcctcgc tgccgtgagc tggatccacg acggcggcgt cggggacgag agaagcggtg    240
ccagccggct ggctcttaga ggtatggccc gaagggcacg gagactgcgg agatttagac    300
gagcgagact gcgcgatctg gatatgctgc tgagcgaact gggctggacc cccttgcccg    360
ataagaacgt gagtcccgtt gatgcctggt tggctaggaa aaggcttgca gaggagtacg    420
tggtagacga gactgaaagg cgccggctcc tgggatatgc cgtcagccat atggcccgac    480
atcgcggctg gcgaaatccc tggacgacga tcaaggatct taagaacttg ccacagccca    540
gcgactcatg ggagaggact cgcgaaagcc tcgaggcccg gtattccgtc tctctggagc    600
ctggcaccgt cgggcagtgg gctggatatc tcctgcagag ggcgccaggg atccgcctga    660
atcccactca acagagcgcc ggccgaagag ccgagctgag taacgccaca gccttcgaaa    720
cgcgcctcag gcaggaagac gtgctttggg aattgagatg tattgcggat gtgcaagggt    780
tgccagagga tgtggtttct aacgtgatag acgctgtatt ctgccaaaag cgcccgagcg    840
tacccgccga gcggattggc cgcgatccac tggacccgag tcagctgcgg gcgagcaggg    900
cctgtctgga gttccaggaa tatagaattg tggccgcagt cgctaatctg agaattcgcg    960
acggatcagg aagcaggcct ctgtcactcg aggaacgcaa cgcggtaatc gaggcgcttc   1020
tcgcccagac ggagcgctct ctgacctggt ccgacatcgc gctggagata ctgaagctcc   1080
ctaatgagag tgacctgact tccgtcccag aagaagacgg cccgagctct ctcgcctatt   1140
cacagtttgc cccccttcgac gaaacgtcag ctcgcatcgc tgagtttatt gccaaaaacc   1200
gccgcaaaat tcccacattc gcccagtggt ggcaggaaca agacaggacg agtagatccg   1260
acctcgtggc cgccctggcg gataatagca tcgcgggaga agaggagcaa gagttgctcg   1320
```

| | |
|---|---|
| ttcatctccc cgatgcggag ctcgaagcct tggaggggct cgccctgccc tctggaaggg | 1380 |
| tcgcgtatag tcggctgacc ctgtctggcc tcacgagagt tatgagagac gatggggtag | 1440 |
| atgtccacaa cgctcggaaa acatgttttg gggtggatga caactggcgg ccgccactgc | 1500 |
| ccgcgctcca tgaggcaacc ggtcaccccg ttgtggaccg gaacttggct attctgagga | 1560 |
| aatttctttc ctcagcgact atgagatggg ggcctcctca atcaatagtc gttgaactgg | 1620 |
| caagggggc atctgaatcc cgcgaaagac aggccgaaga agaggcagcg cggcgcgccc | 1680 |
| accgcaaggc caacgatcgc atcagggcag agctgcgcgc ttccggcctg tccgatcctt | 1740 |
| ctcccgcaga cttggtcagg gcccgactcc ttgaactgta cgactgtcac tgtatgtact | 1800 |
| gcggtgcacc catctcctgg gagaacagcg aactggacca tatcgtgcct cgcactgatg | 1860 |
| gggggtagcaa tagacacgag aacctggcta tcacgtgtgg tgcatgtaat aaggagaaag | 1920 |
| gaaggaggcc ttttgcctca tgggctgaga cttctaaccg ggtccagctc cgggatgtta | 1980 |
| ttgaccgggt ccagaagctg aaatacagcg gcaacatgta ctggaccagg gacgaattct | 2040 |
| ccaggtataa aaagtctgtc gtagcccgct tgaagcgcag gacctccgat cctgaagtca | 2100 |
| ttcagagtat cgagtctaca gggtacgccg ccgtggccct gcgcgatcga ctgctgtcat | 2160 |
| acggggagaa aaatggtgtc gcccaagtgg ctgtatttcg aggggagtg accgcagaag | 2220 |
| cccgagatg gttggacatt agtattgagc gactgttctc acgggtggcc attttcgctc | 2280 |
| agagtaccag cacgaagcgg ctggatcgca gacatcacgc tgtagacgcg gtggtactga | 2340 |
| cgacccttac tcccggcgtg gctaaaacac tggctgatgc ccggtccagg cgagtgtccg | 2400 |
| ccgagttttg gaggcgtcct tctgacgtga atcgacactc cactgaagag ccacagtcac | 2460 |
| cagcctatag acagtggaag gagtcatgta gcgggttggg ggatctcctg atctcaaccg | 2520 |
| ccgcacgaga tagtatagcc gtggcagctc ctctccggct tcggcccacc ggcgccttc | 2580 |
| atgaggagac tctccgcgcc tttagcgagc acactgtcgg ggcagcctgg aagggcgccg | 2640 |
| agcttcgccg aatcgttgag ccagaggtgt acgcagcttt cctggccctg accgatcctg | 2700 |
| ggggcagatt cctcaaggtt agtccaagcg aagacgttct gccagccgac gagaaccggc | 2760 |
| acatcgtgct cagcgatcgg gtgctgggcc ctagggaccg cgttaagctg ttccccgatg | 2820 |
| atcgggggtc catacgagtc aggggggggg ccgcctatat tgcgtcattc catcacgcaa | 2880 |
| gggtgtttag atggggttct tctcattccc catcctttgc actgctgcgc gtcagtctgg | 2940 |
| ccgatctggc cgtggcgggc ctgctgcggg atggggttga tgtgttcact gctgagctcc | 3000 |
| ccccttggac accagcgtgg agatacgcaa gcattgccct ggtgaaagcc gtggaatccg | 3060 |
| gcgatgccaa acaagtgggc tggctggtgc ccggagacga gctcgatttc ggcccagagg | 3120 |
| gggtaaccac tgctgctggc gacttgtcaa tgtttctgaa atatttcccg gagaggcact | 3180 |
| gggtagtgac agggtttgag gatgacaaac gcattaacct gaaacctgca tttctgtctg | 3240 |
| ccgaacaggc cgaggttctc cgcacagaga ggtctgaccg gcctgatact ctgaccgaag | 3300 |
| ccggcgagat tctcgcccag tttttccctc gctgttggcg ggctaccgtt gcgaaggtgc | 3360 |
| tctgtcaccc aggcctgacc gtgatccggc gcacggctct ggggcaacct cgatggcgcc | 3420 |
| ggggccatct gccatatagt tggcgaccct ggagcgccga cccttggagc ggcggaaccc | 3480 |
| ctagcagggc tgaccccaag aagaagagga aggtgaggtc cggcggcgga gagggcagag | 3540 |
| gaagtcttct | 3550 |

<210> SEQ ID NO 2

<211> LENGTH: 3550
<212> TYPE: DNA
<213> ORGANISM: Artificial Sequence
<220> FEATURE:
<223> OTHER INFORMATION: Cas theta - CRISPR(clustered regulatory
      interspaced shor palindromic repeats)_target gene for 10x disign

<400> SEQUENCE: 2

| | |
|---|---|
| agctcctggg caacgtgctg gttattgtgc tgtctcatca ttttggcaaa gaattcgcgg | 60 |
| ccgccaccat gggggggttca gaggtcggta ccgtgccggt aacctggcgg ctcggcgtgg | 120 |
| acgtggggga aagatcaatc gggcttgctg ccgtgtcata tgaagaggac aagcctaagg | 180 |
| aaatcttggc tgcagtgtcc tggatccatg atgggggggg tggcgatgaa cggtccgggg | 240 |
| caagtcgact tgccctccga ggcatggcaa gaagagcccg aaggctgcgc cggtttagga | 300 |
| gagcccgcct ccgcgacctg gacatgttgc tgagtgagtt gggatggacc cccctccctg | 360 |
| acaaaaacgt ctcaccagtt gatgcctggc tggcacgcaa aagactggcc gaggaatatg | 420 |
| tggtggatga aactgagagg cgaagactgc tgggctacgc cgtgtctcat atggcccggc | 480 |
| accgagggtg gcgcaatcca tggactacga ttaaggacct gaaaaatctg ccacagccct | 540 |
| cagactcatg ggagcggact agagagtcac tggaagccag gtatagcgtg tctctggagc | 600 |
| ccggcactgt cgggcaatgg gcaggctatc ttctgcagag agcaccgggc ataagactta | 660 |
| atcccacaca acagtccgcc ggtcgaaggg ccgagttgag taacgcaaca gcctttgaga | 720 |
| caagactgcg acaagaagac gtcctttggg aactgagatg catcgccgat gtgcaagggt | 780 |
| tgcccgagga cgtcgttagc aacgttatag acgcagtgtt ttgccagaaa cggccctccg | 840 |
| taccagcgga aagaatcggc agagatccgc tggaccccag ccagcttcgc gctagcagag | 900 |
| cctgtctgga gtttcaagag tatcggattg tggcagccgt cgcgaatctg agaattagag | 960 |
| atggcagcgg tagtcggcca ctgtctttgg aggagcggaa tgccgttata gaggctctgc | 1020 |
| ttgcgcagac cgaaaggtct ttgacgtgga gcgacattgc gctggaaatt ctgaaactgc | 1080 |
| ctaacgaatc cgacctgacc tctgtcccgg aggaagacgg gcctagctcc ctggcctact | 1140 |
| ctcaatttgc tccgttcgat gagacttcag cccgaatcgc ggaattcatt gcaaaaaacc | 1200 |
| ggcgcaagat ccccacccttt gctcagtggt ggcaagagca agatcggaca agccgcagtg | 1260 |
| acctggtggc tgctctggca gataactcaa tcgctggcga ggaagaacag gagctgcttg | 1320 |
| tccacctgcc ggacgctgag ctcgaggccc ttgaagggct cgccttgcct agcggccggg | 1380 |
| tggcctactc ccgcctgacg ctgtccggac ttaccagggt gatgagagac gatggagtgg | 1440 |
| acgttcacaa cgctcgcaag acttgctttg gagttgacga caactggcgc ccccgctgc | 1500 |
| ctgccctgca cgaagctacc ggacatcccg tggtcgatcg gaatttggcg atcctgcgga | 1560 |
| agtttctctc atccgctacc atgaggtggg gaccacctca atctatcgtg gtggagctgg | 1620 |
| cccggggcgc cagcgagtct cgagagcgac aggccgagga ggaagccgcc agaagagccc | 1680 |
| atcggaaagc caacgatcga ataagagccg agctgcgggc atccggactc agcgatccta | 1740 |
| gccctgctga ccttgtccgc gcaagactgc tggaactgta tgactgccac tgcatgtatt | 1800 |
| gtggggcacc tataagctgg gagaactctg aactggacca catcgtccca cggactgatg | 1860 |
| gcggatcaaa tcgccacgag aatctggcca ttacttgcgg cgcatgtaac aaggagaaag | 1920 |
| gtcgacggcc gtttgcgagt tgggccgaga cgtcaaatag ggtgcagctg agggatgtca | 1980 |
| tcgatcgcgt gcagaaactc aaatactcag gaaaatatga ttggaccaga gacgaattta | 2040 |
| gcagatacaa aaagtctgtg gtagctagac tcaagcgaag gacgtcagac cccgaggtca | 2100 |

```
tccagagtat tgagagtacc ggctatgccg cagtggcgct ccgagacaga ctgctgagct    2160
acggcgagaa aaacggggtg gctcaggtcg cagtctttcg cggaggcgtt acagctgaag    2220
cgagacgctg gcttgatata tccatagaga ggctgttttc tagggtggcc attttttgcgc   2280 agtccactag cacaaagagg ctcgacagac gacatcatgc cgtggatgct gtggttctga    2340
caacgctcac acctggtgtt gcgaagactt tggctgatgc gcgcagcaga cgagttagcg    2400
ccgagttctg gcggaggcct agcgacgtca accgacacag cactgaggag ccgcagagcc    2460
cggcctacag gcaatggaag gaatcttgtt ctggtctggg cgacttgctc atttccactg    2520
ctgcacgaga ttccattgca gtagctgcac ccttgaggct ccggccgact ggagcactgc    2580
acgaagaaac ccttagggcc ttcagtgaac acacggtcgg ggcagcctgg aaaggcgcag    2640
agctgcgcag gattgtggaa cccgaagtat acgccgcctt tctggctttg accgaccctg    2700
gcggccgctt cctgaaagtg tcaccttcag aagatgtgct gcccgcggac gaaaacagac    2760
atatcgtgct gtcagataga gtcctggggc cacgggacag agtgaagctg ttcccagacg    2820
accggggaag tataagggtg cgaggggtg cggcgtatat tgctagcttc caccacgctc     2880
gcgtgtttag gtggggaagc tctcacagcc cctcatttgc cctgctgcgc gtcagtcttg    2940
cagatcttgc ggtagccgga ctgttgaggg atggggtgga cgtcttcact gccgaactcc    3000
ctccttggac acctgcctgg aggtatgcgt caatcgctct ggtcaaagcg gtcgagagtg    3060
gcgatgctaa acaggttggc tggttggtcc ctggcgacga gctggacttc gggcctgaag    3120
gggtcaccac agcggcgggc gacctcagta tgttcttgaa atattttcca gagcgccact    3180
gggttgttac aggatttgaa gacgataaga gaatcaacct taagcccgcc ttcctctctg    3240
ctgaacaggc agaggtgctg cgcaccgagc gcagtgaccg gccggacacc ctgaccgagg    3300
ctggagagat actcgcccaa ttttttcccc gctgttggag agcaaccgtc gccaaggtgc    3360
tctgtcaccc gggactgacg gttattagaa gaacagccct tggccagcca aggtggcgaa    3420
ggggtcacct gccatatagc tggcgtccct ggtcagccga cccatggagc ggtggaaccc    3480
caagcagggc tgaccccaag aagaagagga aggtgaggtc cggcggcgga gagggcagag    3540
gaagtcttct                                                           3550

<210> SEQ ID NO 3
<211> LENGTH: 152
<212> TYPE: DNA
<213> ORGANISM: Artificial Sequence
<220> FEATURE:
<223> OTHER INFORMATION: target_4X_oligo_001

<400> SEQUENCE: 3
gaatcctagt acaagtggcc ggtctcagct cctgggcaac gtgctggtta ttgtgctgtc    60
tcatcatttt ggcaaagaat tcgcggccgc caccatgggg gggtctgagg tgggaacagt    120
accagtgaga ccgacatcca atccggacga ta                                  152

<210> SEQ ID NO 4
<211> LENGTH: 152
<212> TYPE: DNA
<213> ORGANISM: Artificial Sequence
<220> FEATURE:
<223> OTHER INFORMATION: target_4X_oligo_002

<400> SEQUENCE: 4
gaatcctagt acaagtggcc ggtctctgtg ctgtctcatc attttggcaa agaattcgcg    60
gccgccacca tggggggggtc tgaggtggga acagtaccag tgacctggcg cttgggggtt    120
```
gatgtcgaga ccgacatcca atccggacga ta                                     152

<210> SEQ ID NO 5
<211> LENGTH: 152
<212> TYPE: DNA
<213> ORGANISM: Artificial Sequence
<220> FEATURE:
<223> OTHER INFORMATION: target_4X_oligo_003

<400> SEQUENCE: 5
gaatcctagt acaagtggcc ggtctcgaat tcgcggccgc caccatgggg gggtctgagg        60
tgggaacagt accagtgacc tggcgcttgg gggttgatgt cggggagaga agcatagggc       120
ttgcaggaga ccgacatcca atccggacga ta                                     152

<210> SEQ ID NO 6
<211> LENGTH: 152
<212> TYPE: DNA
<213> ORGANISM: Artificial Sequence
<220> FEATURE:
<223> OTHER INFORMATION: target_4X_oligo_004

<400> SEQUENCE: 6
gaatcctagt acaagtggcc ggtctcggtc tgaggtggga acagtaccag tgacctggcg        60
cttgggggtt gatgtcgggg agagaagcat agggcttgca gccgtctcct atgaggaaga       120
caagccgaga ccgacatcca atccggacga ta                                     152

<210> SEQ ID NO 7
<211> LENGTH: 152
<212> TYPE: DNA
<213> ORGANISM: Artificial Sequence
<220> FEATURE:
<223> OTHER INFORMATION: target_4X_oligo_005

<400> SEQUENCE: 7
gaatcctagt acaagtggcc ggtctcgacc tggcgcttgg gggttgatgt cggggagaga        60
agcatagggc ttgcagccgt ctcctatgag gaagacaagc ccaaagaaat cctcgctgcc       120
gtgagcgaga ccgacatcca atccggacga ta                                     152

<210> SEQ ID NO 8
<211> LENGTH: 152
<212> TYPE: DNA
<213> ORGANISM: Artificial Sequence
<220> FEATURE:
<223> OTHER INFORMATION: target_4X_oligo_006

<400> SEQUENCE: 8
gaatcctagt acaagtggcc ggtctcgggg agagaagcat agggcttgca gccgtctcct        60
atgaggaaga caagcccaaa gaaatcctcg ctgccgtgag ctggatccac gacggcggcg       120
tcgggggaga ccgacatcca atccggacga ta                                     152

<210> SEQ ID NO 9
<211> LENGTH: 152
<212> TYPE: DNA
<213> ORGANISM: Artificial Sequence
<220> FEATURE:
<223> OTHER INFORMATION: target_4X_oligo_007

<400> SEQUENCE: 9
gaatcctagt acaagtggcc ggtctcccgt ctcctatgag gaagacaagc ccaaagaaat        60
cctcgctgcc gtgagctgga tccacgacgg cggcgtcggg gacgagagaa gcggtgccag    120
ccggctgaga ccgacatcca atccggacga ta    152

<210> SEQ ID NO 10
<211> LENGTH: 152
<212> TYPE: DNA
<213> ORGANISM: Artificial Sequence
<220> FEATURE:
<223> OTHER INFORMATION: target_4X_oligo_008

<400> SEQUENCE: 10
gaatcctagt acaagtggcc ggtctccaaa gaaatcctcg ctgccgtgag ctggatccac    60
gacggcggcg tcgggacga gagaagcggt gccagccggc tggctcttag aggtatggcc    120
cgaagggaga ccgacatcca atccggacga ta    152

<210> SEQ ID NO 11
<211> LENGTH: 152
<212> TYPE: DNA
<213> ORGANISM: Artificial Sequence
<220> FEATURE:
<223> OTHER INFORMATION: target_4X_oligo_009

<400> SEQUENCE: 11
gaatcctagt acaagtggcc ggtctctgga tccacgacgg cggcgtcggg gacgagagaa    60
gcggtgccag ccggctggct cttagaggta tggcccgaag ggcacggaga ctgcggagat    120
ttagacgaga ccgacatcca atccggacga ta    152

<210> SEQ ID NO 12
<211> LENGTH: 152
<212> TYPE: DNA
<213> ORGANISM: Artificial Sequence
<220> FEATURE:
<223> OTHER INFORMATION: target_4X_oligo_010

<400> SEQUENCE: 12
gaatcctagt acaagtggcc ggtctcacga gagaagcggt gccagccggc tggctcttag    60
aggtatggcc cgaagggcac ggagactgcg gagatttaga cgagcgagac tgcgcgatct    120
ggatatgaga ccgacatcca atccggacga ta    152

<210> SEQ ID NO 13
<211> LENGTH: 152
<212> TYPE: DNA
<213> ORGANISM: Artificial Sequence
<220> FEATURE:
<223> OTHER INFORMATION: target_4X_oligo_011

<400> SEQUENCE: 13
gaatcctagt acaagtggcc ggtctcggct cttagaggta tggcccgaag ggcacggaga    60
ctgcggagat ttagacgagc gagactgcgc gatctggata tgctgctgag cgaactgggc    120
tggaccgaga ccgacatcca atccggacga ta    152

<210> SEQ ID NO 14
<211> LENGTH: 152
<212> TYPE: DNA
<213> ORGANISM: Artificial Sequence
<220> FEATURE:
<223> OTHER INFORMATION: target_4X_oligo_012

<400> SEQUENCE: 14
gaatcctagt acaagtggcc ggtctcgcac ggagactgcg gagatttaga cgagcgagac    60
tgcgcgatct ggatatgctg ctgagcgaac tgggctggac ccccttgccc gataagaacg      120
tgagtcgaga ccgacatcca atccggacga ta                                   152

<210> SEQ ID NO 15
<211> LENGTH: 152
<212> TYPE: DNA
<213> ORGANISM: Artificial Sequence
<220> FEATURE:
<223> OTHER INFORMATION: target_4X_oligo_013

<400> SEQUENCE: 15
gaatcctagt acaagtggcc ggtctcgagc gagactgcgc gatctggata tgctgctgag      60
cgaactgggc tggaccccct gcccgataa gaacgtgagt cccgttgatg cctggttggc      120
taggaagaga ccgacatcca atccggacga ta                                   152

<210> SEQ ID NO 16
<211> LENGTH: 152
<212> TYPE: DNA
<213> ORGANISM: Artificial Sequence
<220> FEATURE:
<223> OTHER INFORMATION: target_4X_oligo_014

<400> SEQUENCE: 16
gaatcctagt acaagtggcc ggtctcgctg ctgagcgaac tgggctggac ccccttgccc      60
gataagaacg tgagtcccgt tgatgcctgg ttggctagga aaaggcttgc agaggagtac      120
gtggtagaga ccgacatcca atccggacga ta                                   152

<210> SEQ ID NO 17
<211> LENGTH: 152
<212> TYPE: DNA
<213> ORGANISM: Artificial Sequence
<220> FEATURE:
<223> OTHER INFORMATION: target_4X_oligo_015

<400> SEQUENCE: 17
gaatcctagt acaagtggcc ggtctcccct tgcccgataa gaacgtgagt cccgttgatg      60
cctggttggc taggaaaagg cttgcagagg agtacgtggt agacgagact gaaaggcgcc      120
ggctccgaga ccgacatcca atccggacga ta                                   152

<210> SEQ ID NO 18
<211> LENGTH: 152
<212> TYPE: DNA
<213> ORGANISM: Artificial Sequence
<220> FEATURE:
<223> OTHER INFORMATION: target_4X_oligo_016

<400> SEQUENCE: 18
gaatcctagt acaagtggcc ggtctcccgt tgatgcctgg ttggctagga aaaggcttgc      60
agaggagtac gtggtagacg agactgaaag gcgccggctc ctgggatatg ccgtcagcca      120
tatggcgaga ccgacatcca atccggacga ta                                   152

<210> SEQ ID NO 19
<211> LENGTH: 152
<212> TYPE: DNA
<213> ORGANISM: Artificial Sequence
<220> FEATURE:
<223> OTHER INFORMATION: target_4X_oligo_017

<400> SEQUENCE: 19

```
gaatcctagt acaagtggcc ggtctcaagg cttgcagagg agtacgtggt agacgagact    60
gaaaggcgcc ggctcctggg atatgccgtc agccatatgg cccgacatcg cggctggcga   120
aatcccgaga ccgacatcca atccggacga ta                                 152
```

<210> SEQ ID NO 20
<211> LENGTH: 152
<212> TYPE: DNA
<213> ORGANISM: Artificial Sequence
<220> FEATURE:
<223> OTHER INFORMATION: target_4X_oligo_018

<400> SEQUENCE: 20

```
gaatcctagt acaagtggcc ggtctcgacg agactgaaag gcgccggctc ctgggatatg    60
ccgtcagcca tatggcccga catcgcggct ggcgaaatcc ctggacgacg atcaaggatc   120
ttaagagaga ccgacatcca atccggacga ta                                 152
```

<210> SEQ ID NO 21
<211> LENGTH: 152
<212> TYPE: DNA
<213> ORGANISM: Artificial Sequence
<220> FEATURE:
<223> OTHER INFORMATION: target_4X_oligo_019

<400> SEQUENCE: 21

```
gaatcctagt acaagtggcc ggtctctggg atatgccgtc agccatatgg cccgacatcg    60
cggctggcga atccctggac gacgatcaag gatcttaag aacttgccac agcccagcga   120
ctcatggaga ccgacatcca atccggacga ta                                 152
```

<210> SEQ ID NO 22
<211> LENGTH: 152
<212> TYPE: DNA
<213> ORGANISM: Artificial Sequence
<220> FEATURE:
<223> OTHER INFORMATION: target_4X_oligo_020

<400> SEQUENCE: 22

```
gaatcctagt acaagtggcc ggtctcccga catcgcggct ggcgaaatcc ctggacgacg    60
atcaaggatc ttaagaactt gccacagccc agcgactcat gggagaggac tcgcgaaagc   120
ctcgaggaga ccgacatcca atccggacga ta                                 152
```

<210> SEQ ID NO 23
<211> LENGTH: 152
<212> TYPE: DNA
<213> ORGANISM: Artificial Sequence
<220> FEATURE:
<223> OTHER INFORMATION: target_4X_oligo_021

<400> SEQUENCE: 23

```
gaatcctagt acaagtggcc ggtctctgga cgacgatcaa ggatcttaag aacttgccac    60
agcccagcga ctcatgggag aggactcgcg aaagcctcga ggcccggtat tccgtctctc   120
tggagcgaga ccgacatcca atccggacga ta                                 152
```

<210> SEQ ID NO 24
<211> LENGTH: 152
<212> TYPE: DNA
<213> ORGANISM: Artificial Sequence
<220> FEATURE:
<223> OTHER INFORMATION: target_4X_oligo_022

<400> SEQUENCE: 24

```
gaatcctagt acaagtggcc ggtctcactt gccacagccc agcgactcat gggagaggac    60
tcgcgaaagc ctcgaggccc ggtattccgt ctctctggag cctggcaccg tcgggcagtg   120
ggctgggaga ccgacatcca atccggacga ta                                 152
```

<210> SEQ ID NO 25
<211> LENGTH: 152
<212> TYPE: DNA
<213> ORGANISM: Artificial Sequence
<220> FEATURE:
<223> OTHER INFORMATION: target_4X_oligo_023

<400> SEQUENCE: 25

```
gaatcctagt acaagtggcc ggtctcggag aggactcgcg aaagcctcga ggcccggtat    60
tccgtctctc tggagcctgg caccgtcggg cagtgggctg gatatctcct gcagagggcg   120
ccaggggaga ccgacatcca atccggacga ta                                 152
```

<210> SEQ ID NO 26
<211> LENGTH: 152
<212> TYPE: DNA
<213> ORGANISM: Artificial Sequence
<220> FEATURE:
<223> OTHER INFORMATION: target_4X_oligo_024

<400> SEQUENCE: 26

```
gaatcctagt acaagtggcc ggtctcgccc ggtattccgt ctctctggag cctggcaccg    60
tcgggcagtg ggctggatat ctcctgcaga gggcgccagg gatccgcctg aatcccactc   120
aacagagaga ccgacatcca atccggacga ta                                 152
```

<210> SEQ ID NO 27
<211> LENGTH: 152
<212> TYPE: DNA
<213> ORGANISM: Artificial Sequence
<220> FEATURE:
<223> OTHER INFORMATION: target_4X_oligo_025

<400> SEQUENCE: 27

```
gaatcctagt acaagtggcc ggtctcctgg caccgtcggg cagtgggctg gatatctcct    60
gcagagggcg ccagggatcc gcctgaatcc cactcaacag agcgccggcc gaagagccga   120
gctgaggaga ccgacatcca atccggacga ta                                 152
```

<210> SEQ ID NO 28
<211> LENGTH: 152
<212> TYPE: DNA
<213> ORGANISM: Artificial Sequence
<220> FEATURE:
<223> OTHER INFORMATION: target_4X_oligo_026

<400> SEQUENCE: 28

```
gaatcctagt acaagtggcc ggtctcatat ctcctgcaga gggcgccagg gatccgcctg    60
aatcccactc aacagagcgc cggccgaaga gccgagctga gtaacgccac agccttcgaa   120
acgcgcgaga ccgacatcca atccggacga ta                                 152
```

<210> SEQ ID NO 29
<211> LENGTH: 152
<212> TYPE: DNA
<213> ORGANISM: Artificial Sequence
<220> FEATURE:
<223> OTHER INFORMATION: target_4X_oligo_027

<400> SEQUENCE: 29
gaatcctagt acaagtggcc ggtctcatcc gcctgaatcc cactcaacag agcgccggcc       60
gaagagccga gctgagtaac gccacagcct tcgaaacgcg cctcaggcag gaagacgtgc      120
tttggggaga ccgacatcca atccggacga ta                                   152

<210> SEQ ID NO 30
<211> LENGTH: 152
<212> TYPE: DNA
<213> ORGANISM: Artificial Sequence
<220> FEATURE:
<223> OTHER INFORMATION: target_4X_oligo_028

<400> SEQUENCE: 30
gaatcctagt acaagtggcc ggtctcgcgc cggccgaaga gccgagctga gtaacgccac       60
agccttcgaa acgcgcctca ggcaggaaga cgtgctttgg gaattgagat gtattgcgga      120
tgtgcagaga ccgacatcca atccggacga ta                                   152

<210> SEQ ID NO 31
<211> LENGTH: 152
<212> TYPE: DNA
<213> ORGANISM: Artificial Sequence
<220> FEATURE:
<223> OTHER INFORMATION: target_4X_oligo_029

<400> SEQUENCE: 31
gaatcctagt acaagtggcc ggtctctaac gccacagcct tcgaaacgcg cctcaggcag       60
gaagacgtgc tttgggaatt gagatgtatt gcggatgtgc aagggttgcc agaggatgtg      120
gtttctgaga ccgacatcca atccggacga ta                                   152

<210> SEQ ID NO 32
<211> LENGTH: 152
<212> TYPE: DNA
<213> ORGANISM: Artificial Sequence
<220> FEATURE:
<223> OTHER INFORMATION: target_4X_oligo_030

<400> SEQUENCE: 32
gaatcctagt acaagtggcc ggtctcctca ggcaggaaga cgtgctttgg gaattgagat       60
gtattgcgga tgtgcaaggg ttgccagagg atgtggtttc taacgtgata dacgctgtat      120
tctgccgaga ccgacatcca atccggacga ta                                   152

<210> SEQ ID NO 33
<211> LENGTH: 152
<212> TYPE: DNA
<213> ORGANISM: Artificial Sequence
<220> FEATURE:
<223> OTHER INFORMATION: target_4X_oligo_031

<400> SEQUENCE: 33
gaatcctagt acaagtggcc ggtctcaatt gagatgtatt gcggatgtgc aagggttgcc       60
agaggatgtg gtttctaacg tgatagacgc tgtattctgc caaaagcgcc cgagcgtacc      120
cgccgagaga ccgacatcca atccggacga ta                                   152

<210> SEQ ID NO 34
<211> LENGTH: 152
<212> TYPE: DNA
<213> ORGANISM: Artificial Sequence
<220> FEATURE:
<223> OTHER INFORMATION: target_4X_oligo_032

<400> SEQUENCE: 34
gaatcctagt acaagtggcc ggtctcaggg ttgccagagg atgtggtttc taacgtgata        60
gacgctgtat tctgccaaaa gcgcccgagc gtacccgccg agcggattgg ccgcgatcca       120
ctggacgaga ccgacatcca atccggacga ta                                     152

<210> SEQ ID NO 35
<211> LENGTH: 152
<212> TYPE: DNA
<213> ORGANISM: Artificial Sequence
<220> FEATURE:
<223> OTHER INFORMATION: target_4X_oligo_033

<400> SEQUENCE: 35
gaatcctagt acaagtggcc ggtctcaacg tgatagacgc tgtattctgc caaaagcgcc        60
cgagcgtacc cgccgagcgg attggccgcg atccactgga cccgagtcag ctgcgggcga       120
gcagggagaa ccgacatcca atccggacga ta                                     152

<210> SEQ ID NO 36
<211> LENGTH: 152
<212> TYPE: DNA
<213> ORGANISM: Artificial Sequence
<220> FEATURE:
<223> OTHER INFORMATION: target_4X_oligo_034

<400> SEQUENCE: 36
gaatcctagt acaagtggcc ggtctcaaaa gcgcccgagc gtaccgccg agcggattgg         60 ccgcgatcca ctggacccga gtcagctgcg ggcgagcagg gcctgtctgg agttccagga      120
atataggaga ccgacatcca atccggacga ta                                     152

<210> SEQ ID NO 37
<211> LENGTH: 152
<212> TYPE: DNA
<213> ORGANISM: Artificial Sequence
<220> FEATURE:
<223> OTHER INFORMATION: target_4X_oligo_035

<400> SEQUENCE: 37
gaatcctagt acaagtggcc ggtctcgcgg attggccgcg atccactgga cccgagtcag        60
ctgcgggcga gcagggcctg tctggagttc caggaatata gaattgtggc cgcagtcgct       120
aatctggaga ccgacatcca atccggacga ta                                     152

<210> SEQ ID NO 38
<211> LENGTH: 152
<212> TYPE: DNA
<213> ORGANISM: Artificial Sequence
<220> FEATURE:
<223> OTHER INFORMATION: target_4X_oligo_036

<400> SEQUENCE: 38
gaatcctagt acaagtggcc ggtctcccga gtcagctgcg ggcgagcagg gcctgtctgg        60
agttccagga atatagaatt gtggccgcag tcgctaatct gagaattcgc gacggatcag       120
gaagcagaga ccgacatcca atccggacga ta                                     152

<210> SEQ ID NO 39
<211> LENGTH: 152
<212> TYPE: DNA
<213> ORGANISM: Artificial Sequence
<220> FEATURE:

<223> OTHER INFORMATION: target_4X_oligo_037

<400> SEQUENCE: 39
gaatcctagt acaagtggcc ggtctccctg tctggagttc caggaatata gaattgtggc      60
cgcagtcgct aatctgagaa ttcgcgacgg atcaggaagc aggcctctgt cactcgagga     120
acgcaagaga ccgacatcca atccggacga ta                                   152

<210> SEQ ID NO 40
<211> LENGTH: 152
<212> TYPE: DNA
<213> ORGANISM: Artificial Sequence
<220> FEATURE:
<223> OTHER INFORMATION: target_4X_oligo_038

<400> SEQUENCE: 40
gaatcctagt acaagtggcc ggtctcaatt gtggccgcag tcgctaatct gagaattcgc      60
gacggatcag gaagcaggcc tctgtcactc gaggaacgca acgcggtaat cgaggcgctt     120
ctcgccgaga ccgacatcca atccggacga ta                                   152

<210> SEQ ID NO 41
<211> LENGTH: 152
<212> TYPE: DNA
<213> ORGANISM: Artificial Sequence
<220> FEATURE:
<223> OTHER INFORMATION: target_4X_oligo_039

<400> SEQUENCE: 41
gaatcctagt acaagtggcc ggtctcagaa ttcgcgacgg atcaggaagc aggcctctgt      60
cactcgagga acgcaacgcg gtaatcgagg cgcttctcgc ccagacggag cgctctctga     120
cctggtgaga ccgacatcca atccggacga ta                                   152

<210> SEQ ID NO 42
<211> LENGTH: 152
<212> TYPE: DNA
<213> ORGANISM: Artificial Sequence
<220> FEATURE:
<223> OTHER INFORMATION: target_4X_oligo_040

<400> SEQUENCE: 42
gaatcctagt acaagtggcc ggtctcggcc tctgtcactc gaggaacgca acgcggtaat      60
cgaggcgctt ctcgcccaga cggagcgctc tctgacctgg tccgacatcg cgctggagat     120
actgaagaga ccgacatcca atccggacga ta                                   152

<210> SEQ ID NO 43
<211> LENGTH: 152
<212> TYPE: DNA
<213> ORGANISM: Artificial Sequence
<220> FEATURE:
<223> OTHER INFORMATION: target_4X_oligo_041

<400> SEQUENCE: 43
gaatcctagt acaagtggcc ggtctccgcg gtaatcgagg cgcttctcgc ccagacggag      60
cgctctctga cctggtccga catcgcgctg gagatactga agctccctaa tgagagtgac     120
ctgactgaga ccgacatcca atccggacga ta                                   152

<210> SEQ ID NO 44
<211> LENGTH: 152
<212> TYPE: DNA
<213> ORGANISM: Artificial Sequence
<220> FEATURE:
<223> OTHER INFORMATION: target_4X_oligo_042

<400> SEQUENCE: 44
gaatcctagt acaagtggcc ggtctccaga cggagcgctc tctgacctgg tccgacatcg    60
cgctggagat actgaagctc cctaatgaga gtgacctgac ttccgtccca gaagaagacg   120
gcccgagaga ccgacatcca atccggacga ta                                 152

<210> SEQ ID NO 45
<211> LENGTH: 152
<212> TYPE: DNA
<213> ORGANISM: Artificial Sequence
<220> FEATURE:
<223> OTHER INFORMATION: target_4X_oligo_043

<400> SEQUENCE: 45
gaatcctagt acaagtggcc ggtctcccga catcgcgctg gagatactga agctccctaa    60
tgagagtgac ctgacttccg tcccagaaga agacggcccg agctctctcg cctattcaca   120
gtttgcgaga ccgacatcca atccggacga ta                                 152

<210> SEQ ID NO 46
<211> LENGTH: 152
<212> TYPE: DNA
<213> ORGANISM: Artificial Sequence
<220> FEATURE:
<223> OTHER INFORMATION: target_4X_oligo_044

<400> SEQUENCE: 46
gaatcctagt acaagtggcc ggtctcgctc cctaatgaga gtgacctgac ttccgtccca    60
gaagaagacg gcccgagctc tctcgcctat tcacagtttg ccccttcga cgaaacgtca   120 gctcgcgaga ccgacatcca atccggacga ta                                 152

<210> SEQ ID NO 47
<211> LENGTH: 152
<212> TYPE: DNA
<213> ORGANISM: Artificial Sequence
<220> FEATURE:
<223> OTHER INFORMATION: target_4X_oligo_045

<400> SEQUENCE: 47
gaatcctagt acaagtggcc ggtctctccg tcccagaaga agacggcccg agctctctcg    60
cctattcaca gtttgccccc ttcgacgaaa cgtcagctcg catcgctgag tttattgcca   120
aaaaccgaga ccgacatcca atccggacga ta                                 152

<210> SEQ ID NO 48
<211> LENGTH: 152
<212> TYPE: DNA
<213> ORGANISM: Artificial Sequence
<220> FEATURE:
<223> OTHER INFORMATION: target_4X_oligo_046

<400> SEQUENCE: 48
gaatcctagt acaagtggcc ggtctcgctc tctcgcctat tcacagtttg ccccttcga    60 cgaaacgtca gctcgcatcg ctgagtttat tgccaaaaac cgccgcaaaa ttcccacatt   120
cgcccagaga ccgacatcca atccggacga ta                                 152

<210> SEQ ID NO 49
<211> LENGTH: 152
<212> TYPE: DNA

<213> ORGANISM: Artificial Sequence
<220> FEATURE:
<223> OTHER INFORMATION: target_4X_oligo_047

<400> SEQUENCE: 49

```
gaatcctagt acaagtggcc ggtctccccc ttcgacgaaa cgtcagctcg catcgctgag    60
tttattgcca aaaccgccg caaaattccc acattcgccc agtggtggca ggaacaagac   120
aggacggaga ccgacatcca atccggacga ta                                152
```

<210> SEQ ID NO 50
<211> LENGTH: 152
<212> TYPE: DNA
<213> ORGANISM: Artificial Sequence
<220> FEATURE:
<223> OTHER INFORMATION: target_4X_oligo_048

<400> SEQUENCE: 50

```
gaatcctagt acaagtggcc ggtctcatcg ctgagtttat tgccaaaaac cgccgcaaaa    60
ttcccacatt cgcccagtgg tggcaggaac aagacaggac gagtagatcc gacctcgtgg   120
ccgcccgaga ccgacatcca atccggacga ta                                152
```

<210> SEQ ID NO 51
<211> LENGTH: 152
<212> TYPE: DNA
<213> ORGANISM: Artificial Sequence
<220> FEATURE:
<223> OTHER INFORMATION: target_4X_oligo_049

<400> SEQUENCE: 51

```
gaatcctagt acaagtggcc ggtctcgccg caaaattccc acattcgccc agtggtggca    60
ggaacaagac aggacgagta gatccgacct cgtggccgcc ctggcggata atagcatcgc   120
gggagagaga ccgacatcca atccggacga ta                                152
```

<210> SEQ ID NO 52
<211> LENGTH: 152
<212> TYPE: DNA
<213> ORGANISM: Artificial Sequence
<220> FEATURE:
<223> OTHER INFORMATION: target_4X_oligo_050

<400> SEQUENCE: 52

```
gaatcctagt acaagtggcc ggtctcgtgg tggcaggaac aagacaggac gagtagatcc    60
gacctcgtgg ccgccctggc ggataatagc atcgcgggag aagaggagca agagttgctc   120
gttcatgaga ccgacatcca atccggacga ta                                152
```

<210> SEQ ID NO 53
<211> LENGTH: 152
<212> TYPE: DNA
<213> ORGANISM: Artificial Sequence
<220> FEATURE:
<223> OTHER INFORMATION: target_4X_oligo_051

<400> SEQUENCE: 53

```
gaatcctagt acaagtggcc ggtctcagta gatccgacct cgtggccgcc ctggcggata    60
atagcatcgc gggagaagag gagcaagagt tgctcgttca tctccccgat gcggagctcg   120
aagcctgaga ccgacatcca atccggacga ta                                152
```

<210> SEQ ID NO 54
<211> LENGTH: 152

```
<212> TYPE: DNA
<213> ORGANISM: Artificial Sequence
<220> FEATURE:
<223> OTHER INFORMATION: target_4X_oligo_052

<400> SEQUENCE: 54
gaatcctagt acaagtggcc ggtctctggc ggataatagc atcgcgggag aagaggagca    60
agagttgctc gttcatctcc ccgatgcgga gctcgaagcc ttggagggggc tcgccctgcc   120 ctctgggaga ccgacatcca atccggacga ta                                  152

<210> SEQ ID NO 55
<211> LENGTH: 152
<212> TYPE: DNA
<213> ORGANISM: Artificial Sequence
<220> FEATURE:
<223> OTHER INFORMATION: target_4X_oligo_053

<400> SEQUENCE: 55
gaatcctagt acaagtggcc ggtctcagag gagcaagagt tgctcgttca tctccccgat    60
gcggagctcg aagccttgga ggggctcgcc ctgccctctg gaagggtcgc gtatagtcgg   120
ctgaccgaga ccgacatcca atccggacga ta                                  152

<210> SEQ ID NO 56
<211> LENGTH: 152
<212> TYPE: DNA
<213> ORGANISM: Artificial Sequence
<220> FEATURE:
<223> OTHER INFORMATION: target_4X_oligo_054

<400> SEQUENCE: 56
gaatcctagt acaagtggcc ggtctcctcc ccgatgcgga gctcgaagcc ttggaggggc    60
tcgccctgcc ctctggaagg gtcgcgtata gtcggctgac cctgtctggc ctcacgagag   120
ttatgagaga ccgacatcca atccggacga ta                                  152

<210> SEQ ID NO 57
<211> LENGTH: 152
<212> TYPE: DNA
<213> ORGANISM: Artificial Sequence
<220> FEATURE:
<223> OTHER INFORMATION: target_4X_oligo_055

<400> SEQUENCE: 57
gaatcctagt acaagtggcc ggtctctgga ggggctcgcc ctgccctctg gaagggtcgc    60
gtatagtcgg ctgaccctgt ctggcctcac gagagttatg agagacgatg gggtagatgt   120
ccacaagaga ccgacatcca atccggacga ta                                  152

<210> SEQ ID NO 58
<211> LENGTH: 152
<212> TYPE: DNA
<213> ORGANISM: Artificial Sequence
<220> FEATURE:
<223> OTHER INFORMATION: target_4X_oligo_056

<400> SEQUENCE: 58
gaatcctagt acaagtggcc ggtctcaagg gtcgcgtata gtcggctgac cctgtctggc    60
ctcacgagag ttatgagaga cgatggggta gatgtccaca acgctcggaa aacatgtttt   120
ggggtggaga ccgacatcca atccggacga ta                                  152

<210> SEQ ID NO 59
```

```
<211> LENGTH: 152
<212> TYPE: DNA
<213> ORGANISM: Artificial Sequence
<220> FEATURE:
<223> OTHER INFORMATION: target_4X_oligo_057

<400> SEQUENCE: 59
gaatcctagt acaagtggcc ggtctcctgt ctggcctcac gagagttatg agagacgatg      60
gggtagatgt ccacaacgct cggaaaacat gttttggggt ggatgacaac tggcggccgc     120
cactgcgaga ccgacatcca atccggacga ta                                   152

<210> SEQ ID NO 60
<211> LENGTH: 152
<212> TYPE: DNA
<213> ORGANISM: Artificial Sequence
<220> FEATURE:
<223> OTHER INFORMATION: target_4X_oligo_058

<400> SEQUENCE: 60
gaatcctagt acaagtggcc ggtctcgaga cgatgggta gatgtccaca acgctcggaa       60
aacatgtttt ggggtggatg acaactggcg ccgccactg cccgcgctcc atgaggcaac     120
cggtcagaga ccgacatcca atccggacga ta                                   152

<210> SEQ ID NO 61
<211> LENGTH: 152
<212> TYPE: DNA
<213> ORGANISM: Artificial Sequence
<220> FEATURE:
<223> OTHER INFORMATION: target_4X_oligo_059

<400> SEQUENCE: 61
gaatcctagt acaagtggcc ggtctccgct cggaaaacat gttttggggt ggatgacaac      60
tggcggccgc cactgcccgc gctccatgag gcaaccggtc accccgttgt ggaccggaac    120
ttggctgaga ccgacatcca atccggacga ta                                   152

<210> SEQ ID NO 62
<211> LENGTH: 152
<212> TYPE: DNA
<213> ORGANISM: Artificial Sequence
<220> FEATURE:
<223> OTHER INFORMATION: target_4X_oligo_060

<400> SEQUENCE: 62
gaatcctagt acaagtggcc ggtctcgatg acaactggcg ccgccactg cccgcgctcc       60 atgaggcaac cggtcacccc gttgtggacc ggaacttggc tattctgagg aaatttcttt    120
cctcaggaga ccgacatcca atccggacga ta                                   152

<210> SEQ ID NO 63
<211> LENGTH: 152
<212> TYPE: DNA
<213> ORGANISM: Artificial Sequence
<220> FEATURE:
<223> OTHER INFORMATION: target_4X_oligo_061

<400> SEQUENCE: 63
gaatcctagt acaagtggcc ggtctcccgc gctccatgag gcaaccggtc accccgttgt      60
ggaccggaac ttggctattc tgaggaaatt tctttcctca gcgactatga gatgggggcc    120
tcctcagaga ccgacatcca atccggacga ta                                   152
```

```
<210> SEQ ID NO 64
<211> LENGTH: 152
<212> TYPE: DNA
<213> ORGANISM: Artificial Sequence
<220> FEATURE:
<223> OTHER INFORMATION: target_4X_oligo_062

<400> SEQUENCE: 64
gaatcctagt acaagtggcc ggtctccccc gttgtggacc ggaacttggc tattctgagg      60
aaatttcttt cctcagcgac tatgagatgg gggcctcctc aatcaatagt cgttgaactg     120
gcaagggaga ccgacatcca atccggacga ta                                   152

<210> SEQ ID NO 65
<211> LENGTH: 152
<212> TYPE: DNA
<213> ORGANISM: Artificial Sequence
<220> FEATURE:
<223> OTHER INFORMATION: target_4X_oligo_063

<400> SEQUENCE: 65
gaatcctagt acaagtggcc ggtctcattc tgaggaaatt tctttcctca gcgactatga      60
gatgggggcc tcctcaatca atagtcgttg aactggcaag ggggcatct gaatcccgcg     120 aaagacgaga ccgacatcca atccggacga ta                                   152

<210> SEQ ID NO 66
<211> LENGTH: 152
<212> TYPE: DNA
<213> ORGANISM: Artificial Sequence
<220> FEATURE:
<223> OTHER INFORMATION: target_4X_oligo_064

<400> SEQUENCE: 66
gaatcctagt acaagtggcc ggtctccgac tatgagatgg gggcctcctc aatcaatagt      60
cgttgaactg gcaagggggg catctgaatc ccgcgaaaga caggccgaag aagaggcagc     120
gcggcggaga ccgacatcca atccggacga ta                                   152

<210> SEQ ID NO 67
<211> LENGTH: 152
<212> TYPE: DNA
<213> ORGANISM: Artificial Sequence
<220> FEATURE:
<223> OTHER INFORMATION: target_4X_oligo_065

<400> SEQUENCE: 67
gaatcctagt acaagtggcc ggtctcatca atagtcgttg aactggcaag ggggcatct      60 gaatcccgcg aaagacaggc cgaagaagag gcagcgcggc gcgcccaccg caaggccaac    120
gatcgcgaga ccgacatcca atccggacga ta                                   152

<210> SEQ ID NO 68
<211> LENGTH: 152
<212> TYPE: DNA
<213> ORGANISM: Artificial Sequence
<220> FEATURE:
<223> OTHER INFORMATION: target_4X_oligo_066

<400> SEQUENCE: 68
gaatcctagt acaagtggcc ggtctcgggg catctgaatc ccgcgaaaga caggccgaag      60
aagaggcagc gcggcgcgcc caccgcaagg ccaacgatcg catcagggca gagctgcgcg     120
cttccggaga ccgacatcca atccggacga ta                                   152
```

<210> SEQ ID NO 69
<211> LENGTH: 152
<212> TYPE: DNA
<213> ORGANISM: Artificial Sequence
<220> FEATURE:
<223> OTHER INFORMATION: target_4X_oligo_067

<400> SEQUENCE: 69
gaatcctagt acaagtggcc ggtctcaggc cgaagaagag gcagcgcggc gcgcccaccg    60
caaggccaac gatcgcatca gggcagagct gcgcgcttcc ggcctgtccg atccttctcc   120
cgcagagaga ccgacatcca atccggacga ta                                 152

<210> SEQ ID NO 70
<211> LENGTH: 152
<212> TYPE: DNA
<213> ORGANISM: Artificial Sequence
<220> FEATURE:
<223> OTHER INFORMATION: target_4X_oligo_068

<400> SEQUENCE: 70
gaatcctagt acaagtggcc ggtctccgcc caccgcaagg ccaacgatcg catcagggca    60
gagctgcgcg cttccggcct gtccgatcct tctcccgcag acttggtcag ggcccgactc   120
cttgaagaga ccgacatcca atccggacga ta                                 152

<210> SEQ ID NO 71
<211> LENGTH: 152
<212> TYPE: DNA
<213> ORGANISM: Artificial Sequence
<220> FEATURE:
<223> OTHER INFORMATION: target_4X_oligo_069

<400> SEQUENCE: 71
gaatcctagt acaagtggcc ggtctcatca gggcagagct gcgcgcttcc ggcctgtccg    60
atccttctcc cgcagacttg gtcagggccc gactccttga actgtacgac tgtcactgta   120
tgtactgaga ccgacatcca atccggacga ta                                 152

<210> SEQ ID NO 72
<211> LENGTH: 152
<212> TYPE: DNA
<213> ORGANISM: Artificial Sequence
<220> FEATURE:
<223> OTHER INFORMATION: target_4X_oligo_070

<400> SEQUENCE: 72
gaatcctagt acaagtggcc ggtctcgcct gtccgatcct tctcccgcag acttggtcag    60
ggcccgactc cttgaactgt acgactgtca ctgtatgtac tgcggtgcac ccatctcctg   120
ggagaagaga ccgacatcca atccggacga ta                                 152

<210> SEQ ID NO 73
<211> LENGTH: 152
<212> TYPE: DNA
<213> ORGANISM: Artificial Sequence
<220> FEATURE:
<223> OTHER INFORMATION: target_4X_oligo_071

<400> SEQUENCE: 73
gaatcctagt acaagtggcc ggtctccttg gtcagggccc gactccttga actgtacgac    60
tgtcactgta tgtactgcgg tgcacccatc tcctgggaga acagcgaact ggaccatatc   120
gtgcctgaga ccgacatcca atccggacga ta                                 152

<210> SEQ ID NO 74
<211> LENGTH: 152
<212> TYPE: DNA
<213> ORGANISM: Artificial Sequence
<220> FEATURE:
<223> OTHER INFORMATION: target_4X_oligo_072

<400> SEQUENCE: 74
gaatcctagt acaagtggcc ggtctcctgt acgactgtca ctgtatgtac tgcggtgcac    60
ccatctcctg ggagaacagc gaactggacc atatcgtgcc tcgcactgat ggggggtagca   120 atagacgaga ccgacatcca atccggacga ta                                  152

<210> SEQ ID NO 75
<211> LENGTH: 152
<212> TYPE: DNA
<213> ORGANISM: Artificial Sequence
<220> FEATURE:
<223> OTHER INFORMATION: target_4X_oligo_073

<400> SEQUENCE: 75
gaatcctagt acaagtggcc ggtctcgcgg tgcacccatc tcctgggaga acagcgaact    60
ggaccatatc gtgcctcgca ctgatggggg tagcaataga cacgagaacc tggctatcac   120
gtgtgggaga ccgacatcca atccggacga ta                                  152

<210> SEQ ID NO 76
<211> LENGTH: 152
<212> TYPE: DNA
<213> ORGANISM: Artificial Sequence
<220> FEATURE:
<223> OTHER INFORMATION: target_4X_oligo_074

<400> SEQUENCE: 76
gaatcctagt acaagtggcc ggtctccagc gaactggacc atatcgtgcc tcgcactgat    60 ggggggtagca atagacacga gaacctggct atcacgtgtg gtgcatgtaa taaggagaaa   120
ggaagggaga ccgacatcca atccggacga ta                                  152

<210> SEQ ID NO 77
<211> LENGTH: 152
<212> TYPE: DNA
<213> ORGANISM: Artificial Sequence
<220> FEATURE:
<223> OTHER INFORMATION: target_4X_oligo_075

<400> SEQUENCE: 77
gaatcctagt acaagtggcc ggtctccgca ctgatggggg tagcaataga cacgagaacc    60
tggctatcac gtgtggtgca tgtaataagg agaaaggaag gaggcctttt gcctcatggg   120
ctgagagaga ccgacatcca atccggacga ta                                  152

<210> SEQ ID NO 78
<211> LENGTH: 152
<212> TYPE: DNA
<213> ORGANISM: Artificial Sequence
<220> FEATURE:
<223> OTHER INFORMATION: target_4X_oligo_076

<400> SEQUENCE: 78
gaatcctagt acaagtggcc ggtctcacga gaacctggct atcacgtgtg gtgcatgtaa    60
taaggagaaa ggaaggaggc cttttgcctc atgggctgag acttctaacc gggtccagct   120

```
ccgggagaga ccgacatcca atccggacga ta                                 152
```

<210> SEQ ID NO 79
<211> LENGTH: 152
<212> TYPE: DNA
<213> ORGANISM: Artificial Sequence
<220> FEATURE:
<223> OTHER INFORMATION: target_4X_oligo_077

<400> SEQUENCE: 79

```
gaatcctagt acaagtggcc ggtctctgca tgtaataagg agaaaggaag gaggccttt      60 gcctcatggg ctgagacttc taaccgggtc cagctccggg atgttattga ccgggtccag    120
aagctggaga ccgacatcca atccggacga ta                                 152
```

<210> SEQ ID NO 80
<211> LENGTH: 152
<212> TYPE: DNA
<213> ORGANISM: Artificial Sequence
<220> FEATURE:
<223> OTHER INFORMATION: target_4X_oligo_078

<400> SEQUENCE: 80

```
gaatcctagt acaagtggcc ggtctcaggc cttttgcctc atgggctgag acttctaacc     60
gggtccagct ccgggatgtt attgaccggg tccagaagct gaaatacagc ggcaacatgt   120
actggagaga ccgacatcca atccggacga ta                                 152
```

<210> SEQ ID NO 81
<211> LENGTH: 152
<212> TYPE: DNA
<213> ORGANISM: Artificial Sequence
<220> FEATURE:
<223> OTHER INFORMATION: target_4X_oligo_079

<400> SEQUENCE: 81

```
gaatcctagt acaagtggcc ggtctccttc taaccgggtc cagctccggg atgttattga     60
ccgggtccag aagctgaaat acagcggcaa catgtactgg accagggacg aattctccag   120
gtataagaga ccgacatcca atccggacga ta                                 152
```

<210> SEQ ID NO 82
<211> LENGTH: 152
<212> TYPE: DNA
<213> ORGANISM: Artificial Sequence
<220> FEATURE:
<223> OTHER INFORMATION: target_4X_oligo_080

<400> SEQUENCE: 82

```
gaatcctagt acaagtggcc ggtctctgtt attgaccggg tccagaagct gaaatacagc     60
ggcaacatgt actggaccag ggacgaattc tccaggtata aaaagtctgt cgtagcccgc   120
ttgaaggaga ccgacatcca atccggacga ta                                 152
```

<210> SEQ ID NO 83
<211> LENGTH: 152
<212> TYPE: DNA
<213> ORGANISM: Artificial Sequence
<220> FEATURE:
<223> OTHER INFORMATION: target_4X_oligo_081

<400> SEQUENCE: 83

```
gaatcctagt acaagtggcc ggtctcaaat acagcggcaa catgtactgg accagggacg     60
aattctccag gtataaaaag tctgtcgtag cccgcttgaa gcgcaggacc tccgatcctg   120
```
aagtcagaga ccgacatcca atccggacga ta       152

<210> SEQ ID NO 84
<211> LENGTH: 152
<212> TYPE: DNA
<213> ORGANISM: Artificial Sequence
<220> FEATURE:
<223> OTHER INFORMATION: target_4X_oligo_082

<400> SEQUENCE: 84
gaatcctagt acaagtggcc ggtctcccag ggacgaattc tccaggtata aaaagtctgt       60
cgtagcccgc ttgaagcgca ggacctccga tcctgaagtc attcagagta tcgagtctac      120
agggtagaga ccgacatcca atccggacga ta      152

<210> SEQ ID NO 85
<211> LENGTH: 152
<212> TYPE: DNA
<213> ORGANISM: Artificial Sequence
<220> FEATURE:
<223> OTHER INFORMATION: target_4X_oligo_083

<400> SEQUENCE: 85
gaatcctagt acaagtggcc ggtctcaaag tctgtcgtag cccgcttgaa gcgcaggacc       60
tccgatcctg aagtcattca gagtatcgag tctacagggt acgccgccgt ggccctgcgc      120
gatcgagaga ccgacatcca atccggacga ta      152

<210> SEQ ID NO 86
<211> LENGTH: 152
<212> TYPE: DNA
<213> ORGANISM: Artificial Sequence
<220> FEATURE:
<223> OTHER INFORMATION: target_4X_oligo_084

<400> SEQUENCE: 86
gaatcctagt acaagtggcc ggtctccgca ggacctccga tcctgaagtc attcagagta       60
tcgagtctac agggtacgcc gccgtggccc tgcgcgatcg actgctgtca tacggggaga      120
aaaatggaga ccgacatcca atccggacga ta      152

<210> SEQ ID NO 87
<211> LENGTH: 152
<212> TYPE: DNA
<213> ORGANISM: Artificial Sequence
<220> FEATURE:
<223> OTHER INFORMATION: target_4X_oligo_085

<400> SEQUENCE: 87
gaatcctagt acaagtggcc ggtctcttca gagtatcgag tctacagggt acgccgccgt       60
ggccctgcgc gatcgactgc tgtcatacgg ggagaaaaat ggtgtcgccc aagtggctgt      120
atttcggaga ccgacatcca atccggacga ta      152

<210> SEQ ID NO 88
<211> LENGTH: 152
<212> TYPE: DNA
<213> ORGANISM: Artificial Sequence
<220> FEATURE:
<223> OTHER INFORMATION: target_4X_oligo_086

<400> SEQUENCE: 88
gaatcctagt acaagtggcc ggtctccgcc gccgtggccc tgcgcgatcg actgctgtca       60
tacggggaga aaaatggtgt cgcccaagtg gctgtatttc gaggggagt gaccgcagaa    120 gcccgggaga ccgacatcca atccggacga ta    152

<210> SEQ ID NO 89
<211> LENGTH: 152
<212> TYPE: DNA
<213> ORGANISM: Artificial Sequence
<220> FEATURE:
<223> OTHER INFORMATION: target_4X_oligo_087

<400> SEQUENCE: 89
gaatcctagt acaagtggcc ggtctcctgc tgtcatacgg ggagaaaaat ggtgtcgccc    60
aagtggctgt atttcgaggg ggagtgaccg cagaagcccg agatggttg acattagta    120 ttgagcgaga ccgacatcca atccggacga ta    152

<210> SEQ ID NO 90
<211> LENGTH: 152
<212> TYPE: DNA
<213> ORGANISM: Artificial Sequence
<220> FEATURE:
<223> OTHER INFORMATION: target_4X_oligo_088

<400> SEQUENCE: 90
gaatcctagt acaagtggcc ggtctcgtgt cgcccaagtg gctgtatttc gaggggagt    60 gaccgcagaa gcccggagat ggttggacat tagtattgag cgactgttct cacgggtggc    120
cattttgaga ccgacatcca atccggacga ta    152

<210> SEQ ID NO 91
<211> LENGTH: 152
<212> TYPE: DNA
<213> ORGANISM: Artificial Sequence
<220> FEATURE:
<223> OTHER INFORMATION: target_4X_oligo_089

<400> SEQUENCE: 91
gaatcctagt acaagtggcc ggtctcaggg ggagtgaccg cagaagcccg gagatggttg    60
gacattagta ttgagcgact gttctcacgg gtggccattt tcgctcagag taccagcacg    120
aagcgggaga ccgacatcca atccggacga ta    152

<210> SEQ ID NO 92
<211> LENGTH: 152
<212> TYPE: DNA
<213> ORGANISM: Artificial Sequence
<220> FEATURE:
<223> OTHER INFORMATION: target_4X_oligo_090

<400> SEQUENCE: 92
gaatcctagt acaagtggcc ggtctcagat ggttggacat tagtattgag cgactgttct    60
cacgggtggc cattttcgct cagagtacca gcacgaagcg gctggatcgc agacatcacg    120
ctgtaggaga ccgacatcca atccggacga ta    152

<210> SEQ ID NO 93
<211> LENGTH: 152
<212> TYPE: DNA
<213> ORGANISM: Artificial Sequence
<220> FEATURE:
<223> OTHER INFORMATION: target_4X_oligo_091

<400> SEQUENCE: 93
gaatcctagt acaagtggcc ggtctcgact gttctcacgg gtggccattt tcgctcagag    60
taccagcacg aagcggctgg atcgcagaca tcacgctgta gacgcggtgg tactgacgac    120
ccttacgaga ccgacatcca atccggacga ta                                 152

<210> SEQ ID NO 94
<211> LENGTH: 152
<212> TYPE: DNA
<213> ORGANISM: Artificial Sequence
<220> FEATURE:
<223> OTHER INFORMATION: target_4X_oligo_092

<400> SEQUENCE: 94
gaatcctagt acaagtggcc ggtctccgct cagagtacca gcacgaagcg gctggatcgc    60
agacatcacg ctgtagacgc ggtggtactg acgaccctta ctcccggcgt ggctaaaaca   120
ctggctgaga ccgacatcca atccggacga ta                                 152

<210> SEQ ID NO 95
<211> LENGTH: 152
<212> TYPE: DNA
<213> ORGANISM: Artificial Sequence
<220> FEATURE:
<223> OTHER INFORMATION: target_4X_oligo_093

<400> SEQUENCE: 95
gaatcctagt acaagtggcc ggtctcctgg atcgcagaca tcacgctgta gacgcggtgg    60
tactgacgac ccttactccc ggcgtggcta aaacactggc tgatgcccgg tccaggcgag   120
tgtccggaga ccgacatcca atccggacga ta                                 152

<210> SEQ ID NO 96
<211> LENGTH: 152
<212> TYPE: DNA
<213> ORGANISM: Artificial Sequence
<220> FEATURE:
<223> OTHER INFORMATION: target_4X_oligo_094

<400> SEQUENCE: 96
gaatcctagt acaagtggcc ggtctcacgc ggtggtactg acgaccctta ctcccggcgt    60
ggctaaaaca ctggctgatg cccggtccag gcgagtgtcc gccgagtttt ggaggcgtcc   120
ttctgagaga ccgacatcca atccggacga ta                                 152

<210> SEQ ID NO 97
<211> LENGTH: 152
<212> TYPE: DNA
<213> ORGANISM: Artificial Sequence
<220> FEATURE:
<223> OTHER INFORMATION: target_4X_oligo_095

<400> SEQUENCE: 97
gaatcctagt acaagtggcc ggtctctccc ggcgtggcta aaacactggc tgatgcccgg    60
tccaggcgag tgtccgccga gttttggagg cgtccttctg acgtgaatcg acactccact   120
gaagaggaga ccgacatcca atccggacga ta                                 152

<210> SEQ ID NO 98
<211> LENGTH: 152
<212> TYPE: DNA
<213> ORGANISM: Artificial Sequence
<220> FEATURE:
<223> OTHER INFORMATION: target_4X_oligo_096

<400> SEQUENCE: 98

```
gaatcctagt acaagtggcc ggtctcgatg cccggtccag gcgagtgtcc gccgagtttt      60
ggaggcgtcc ttctgacgtg aatcgacact ccactgaaga gccacagtca ccagcctata     120
gacagtgaga ccgacatcca atccggacga ta                                   152

<210> SEQ ID NO 99
<211> LENGTH: 152
<212> TYPE: DNA
<213> ORGANISM: Artificial Sequence
<220> FEATURE:
<223> OTHER INFORMATION: target_4X_oligo_097

<400> SEQUENCE: 99
gaatcctagt acaagtggcc ggtctcccga gttttggagg cgtccttctg acgtgaatcg      60
acactccact gaagagccac agtcaccagc ctatagacag tggaaggagt catgtagcgg     120
gttggggaga ccgacatcca atccggacga ta                                   152

<210> SEQ ID NO 100
<211> LENGTH: 152
<212> TYPE: DNA
<213> ORGANISM: Artificial Sequence
<220> FEATURE:
<223> OTHER INFORMATION: target_4X_oligo_098

<400> SEQUENCE: 100
gaatcctagt acaagtggcc ggtctccgtg aatcgacact ccactgaaga gccacagtca      60
ccagcctata gacagtggaa ggagtcatgt agcgggttgg gggatctcct gatctcaacc     120
gccgcagaga ccgacatcca atccggacga ta                                   152

<210> SEQ ID NO 101
<211> LENGTH: 152
<212> TYPE: DNA
<213> ORGANISM: Artificial Sequence
<220> FEATURE:
<223> OTHER INFORMATION: target_4X_oligo_099

<400> SEQUENCE: 101
gaatcctagt acaagtggcc ggtctcccac agtcaccagc ctatagacag tggaaggagt      60
catgtagcgg gttgggggat ctcctgatct caaccgccgc acgagatagt atagccgtgg     120
cagctcgaga ccgacatcca atccggacga ta                                   152

<210> SEQ ID NO 102
<211> LENGTH: 152
<212> TYPE: DNA
<213> ORGANISM: Artificial Sequence
<220> FEATURE:
<223> OTHER INFORMATION: target_4X_oligo_100

<400> SEQUENCE: 102
gaatcctagt acaagtggcc ggtctcggaa ggagtcatgt agcgggttgg gggatctcct      60
gatctcaacc gccgcacgag atagtatagc cgtggcagct cctctccggc ttcggcccac     120
cggcgcgaga ccgacatcca atccggacga ta                                   152

<210> SEQ ID NO 103
<211> LENGTH: 152
<212> TYPE: DNA
<213> ORGANISM: Artificial Sequence
<220> FEATURE:
<223> OTHER INFORMATION: target_4X_oligo_101

<400> SEQUENCE: 103
```

```
gaatcctagt acaagtggcc ggtctcggat ctcctgatct caaccgccgc acgagatagt    60
atagccgtgg cagctcctct ccggcttcgg cccaccggcg cccttcatga ggagactctc   120
cgcgccgaga ccgacatcca atccggacga ta                                 152

<210> SEQ ID NO 104
<211> LENGTH: 152
<212> TYPE: DNA
<213> ORGANISM: Artificial Sequence
<220> FEATURE:
<223> OTHER INFORMATION: target_4X_oligo_102

<400> SEQUENCE: 104
gaatcctagt acaagtggcc ggtctccgag atagtatagc cgtggcagct cctctccggc    60
ttcggcccac cggcgccctt catgaggaga ctctccgcgc ctttagcgag cacactgtcg   120
gggcaggaga ccgacatcca atccggacga ta                                 152

<210> SEQ ID NO 105
<211> LENGTH: 152
<212> TYPE: DNA
<213> ORGANISM: Artificial Sequence
<220> FEATURE:
<223> OTHER INFORMATION: target_4X_oligo_103

<400> SEQUENCE: 105
gaatcctagt acaagtggcc ggtctcctct ccggcttcgg cccaccggcg cccttcatga    60
ggagactctc cgcgccttta gcgagcacac tgtcggggca gcctggaagg gcgccgagct   120
tcgccggaga ccgacatcca atccggacga ta                                 152

<210> SEQ ID NO 106
<211> LENGTH: 152
<212> TYPE: DNA
<213> ORGANISM: Artificial Sequence
<220> FEATURE:
<223> OTHER INFORMATION: target_4X_oligo_104

<400> SEQUENCE: 106
gaatcctagt acaagtggcc ggtctccctt catgaggaga ctctccgcgc ctttagcgag    60
cacactgtcg gggcagcctg aagggcgcc gagcttcgcc gaatcgttga gccagaggtg    120
tacgcagaga ccgacatcca atccggacga ta                                 152

<210> SEQ ID NO 107
<211> LENGTH: 152
<212> TYPE: DNA
<213> ORGANISM: Artificial Sequence
<220> FEATURE:
<223> OTHER INFORMATION: target_4X_oligo_105

<400> SEQUENCE: 107
gaatcctagt acaagtggcc ggtctcttta gcgagcacac tgtcggggca gcctggaagg    60
gcgccgagct tcgccgaatc gttgagccag aggtgtacgc agctttcctg gccctgaccg   120
atcctggaga ccgacatcca atccggacga ta                                 152

<210> SEQ ID NO 108
<211> LENGTH: 152
<212> TYPE: DNA
<213> ORGANISM: Artificial Sequence
<220> FEATURE:
<223> OTHER INFORMATION: target_4X_oligo_106
```

```
<400> SEQUENCE: 108
gaatcctagt acaagtggcc ggtctccctg aagggcgcc gagcttcgcc gaatcgttga      60
gccagaggtg tacgcagctt cctggccct gaccgatcct gggggcagat tcctcaaggt    120
tagtccgaga ccgacatcca atccggacga ta                                 152

<210> SEQ ID NO 109
<211> LENGTH: 152
<212> TYPE: DNA
<213> ORGANISM: Artificial Sequence
<220> FEATURE:
<223> OTHER INFORMATION: target_4X_oligo_107

<400> SEQUENCE: 109
gaatcctagt acaagtggcc ggtctcaatc gttgagccag aggtgtacgc agctttcctg    60
gccctgaccg atcctggggg cagattcctc aaggttagtc caagcgaaga cgttctgcca   120
gccgacgaga ccgacatcca atccggacga ta                                 152

<210> SEQ ID NO 110
<211> LENGTH: 152
<212> TYPE: DNA
<213> ORGANISM: Artificial Sequence
<220> FEATURE:
<223> OTHER INFORMATION: target_4X_oligo_108

<400> SEQUENCE: 110
gaatcctagt acaagtggcc ggtctcgctt tcctggccct gaccgatcct gggggcagat    60
tcctcaaggt tagtccaagc gaagacgttc tgccagccga cgagaaccgg cacatcgtgc   120
tcagcggaga ccgacatcca atccggacga ta                                 152

<210> SEQ ID NO 111
<211> LENGTH: 152
<212> TYPE: DNA
<213> ORGANISM: Artificial Sequence
<220> FEATURE:
<223> OTHER INFORMATION: target_4X_oligo_109

<400> SEQUENCE: 111
gaatcctagt acaagtggcc ggtctcgggg cagattcctc aaggttagtc caagcgaaga    60
cgttctgcca gccgacgaga accggcacat cgtgctcagc gatcgggtgc tgggccctag   120
ggaccggaga ccgacatcca atccggacga ta                                 152

<210> SEQ ID NO 112
<211> LENGTH: 152
<212> TYPE: DNA
<213> ORGANISM: Artificial Sequence
<220> FEATURE:
<223> OTHER INFORMATION: target_4X_oligo_110

<400> SEQUENCE: 112
gaatcctagt acaagtggcc ggtctcaagc gaagacgttc tgccagccga cgagaaccgg    60
cacatcgtgc tcagcgatcg ggtgctgggc cctagggacc gcgttaagct gttccccgat   120
gatcgggaga ccgacatcca atccggacga ta                                 152

<210> SEQ ID NO 113
<211> LENGTH: 152
<212> TYPE: DNA
<213> ORGANISM: Artificial Sequence
<220> FEATURE:
<223> OTHER INFORMATION: target_4X_oligo_111
```

<400> SEQUENCE: 113
gaatcctagt acaagtggcc ggtctcgaga accggcacat cgtgctcagc gatcgggtgc    60
tgggccctag ggaccgcgtt aagctgttcc ccgatgatcg ggggtccata cgagtcaggg    120 ggggggggaga ccgacatcca atccggacga ta    152

<210> SEQ ID NO 114
<211> LENGTH: 152
<212> TYPE: DNA
<213> ORGANISM: Artificial Sequence
<220> FEATURE:
<223> OTHER INFORMATION: target_4X_oligo_112

<400> SEQUENCE: 114
gaatcctagt acaagtggcc ggtctcatcg ggtgctgggc cctagggacc gcgttaagct    60
gttccccgat gatcggggt ccatacgagt caggggggg gccgcctata ttgcgtcatt     120
ccatcagaga ccgacatcca atccggacga ta    152

<210> SEQ ID NO 115
<211> LENGTH: 152
<212> TYPE: DNA
<213> ORGANISM: Artificial Sequence
<220> FEATURE:
<223> OTHER INFORMATION: target_4X_oligo_113

<400> SEQUENCE: 115
gaatcctagt acaagtggcc ggtctccgtt aagctgttcc ccgatgatcg ggggtccata    60
cgagtcaggg gggggccgc ctatattgcg tcattccatc acgcaagggt gtttagatgg     120
ggttctgaga ccgacatcca atccggacga ta    152

<210> SEQ ID NO 116
<211> LENGTH: 152
<212> TYPE: DNA
<213> ORGANISM: Artificial Sequence
<220> FEATURE:
<223> OTHER INFORMATION: target_4X_oligo_114

<400> SEQUENCE: 116
gaatcctagt acaagtggcc ggtctcgggt ccatacgagt caggggggg gccgcctata     60 ttgcgtcatt ccatcacgca agggtgttta gatggggttc ttctcattcc ccatcctttg    120
cactgcgaga ccgacatcca atccggacga ta    152

<210> SEQ ID NO 117
<211> LENGTH: 152
<212> TYPE: DNA
<213> ORGANISM: Artificial Sequence
<220> FEATURE:
<223> OTHER INFORMATION: target_4X_oligo_115

<400> SEQUENCE: 117
gaatcctagt acaagtggcc ggtctcccgc ctatattgcg tcattccatc acgcaagggt    60
gtttagatgg ggttcttctc attccccatc ctttgcactg ctgcgcgtca gtctggccga    120
tctggcgaga ccgacatcca atccggacga ta    152

<210> SEQ ID NO 118
<211> LENGTH: 152
<212> TYPE: DNA
<213> ORGANISM: Artificial Sequence
<220> FEATURE:

<223> OTHER INFORMATION: target_4X_oligo_116

<400> SEQUENCE: 118
gaatcctagt acaagtggcc ggtctccgca agggtgttta gatggggttc ttctcattcc      60
ccatcctttg cactgctgcg cgtcagtctg gccgatctgg ccgtggcggg cctgctgcgg     120
gatggggaga ccgacatcca atccggacga ta                                    152

<210> SEQ ID NO 119
<211> LENGTH: 152
<212> TYPE: DNA
<213> ORGANISM: Artificial Sequence
<220> FEATURE:
<223> OTHER INFORMATION: target_4X_oligo_117

<400> SEQUENCE: 119
gaatcctagt acaagtggcc ggtctctctc attccccatc ctttgcactg ctgcgcgtca      60
gtctggccga tctggccgtg gcgggcctgc tgcgggatgg ggttgatgtg ttcactgctg     120
agctccgaga ccgacatcca atccggacga ta                                    152

<210> SEQ ID NO 120
<211> LENGTH: 152
<212> TYPE: DNA
<213> ORGANISM: Artificial Sequence
<220> FEATURE:
<223> OTHER INFORMATION: target_4X_oligo_118

<400> SEQUENCE: 120
gaatcctagt acaagtggcc ggtctctgcg cgtcagtctg gccgatctgg ccgtggcggg      60
cctgctgcgg gatggggttg atgtgttcac tgctgagctc ccccccttgga caccagcgtg   120 gagatagaga ccgacatcca atccggacga ta                                    152

<210> SEQ ID NO 121
<211> LENGTH: 152
<212> TYPE: DNA
<213> ORGANISM: Artificial Sequence
<220> FEATURE:
<223> OTHER INFORMATION: target_4X_oligo_119

<400> SEQUENCE: 121
gaatcctagt acaagtggcc ggtctccgtg gcgggcctgc tgcgggatgg ggttgatgtg      60
ttcactgctg agctcccccc ttggacacca gcgtggagat acgcaagcat tgccctggtg     120
aaagccgaga ccgacatcca atccggacga ta                                    152

<210> SEQ ID NO 122
<211> LENGTH: 152
<212> TYPE: DNA
<213> ORGANISM: Artificial Sequence
<220> FEATURE:
<223> OTHER INFORMATION: target_4X_oligo_120

<400> SEQUENCE: 122
gaatcctagt acaagtggcc ggtctcgttg atgtgttcac tgctgagctc ccccccttgga      60 caccagcgtg gagatacgca agcattgccc tggtgaaagc cgtggaatcc ggcgatgcca     120
aacaaggaga ccgacatcca atccggacga ta                                    152

<210> SEQ ID NO 123
<211> LENGTH: 152
<212> TYPE: DNA
<213> ORGANISM: Artificial Sequence

```
<220> FEATURE:
<223> OTHER INFORMATION: target_4X_oligo_121

<400> SEQUENCE: 123
gaatcctagt acaagtggcc ggtctccccc ttggacacca gcgtggagat acgcaagcat      60
tgccctggtg aaagccgtgg aatcggcga tgccaaacaa gtgggctggc tggtgcccgg     120
agacgagaga ccgacatcca atccggacga ta                                  152

<210> SEQ ID NO 124
<211> LENGTH: 152
<212> TYPE: DNA
<213> ORGANISM: Artificial Sequence
<220> FEATURE:
<223> OTHER INFORMATION: target_4X_oligo_122

<400> SEQUENCE: 124
gaatcctagt acaagtggcc ggtctccgca agcattgccc tggtgaaagc cgtggaatcc      60
ggcgatgcca acaagtggg ctggctggtg cccggagacg agctcgattt cggcccagag     120
ggggtagaga ccgacatcca atccggacga ta                                  152

<210> SEQ ID NO 125
<211> LENGTH: 152
<212> TYPE: DNA
<213> ORGANISM: Artificial Sequence
<220> FEATURE:
<223> OTHER INFORMATION: target_4X_oligo_123

<400> SEQUENCE: 125
gaatcctagt acaagtggcc ggtctcgtgg aatccggcga tgccaaacaa gtgggctggc      60
tggtgcccgg agacgagctc gatttcggcc cagaggggt aaccactgct gctggcgact     120
tgtcaagaga ccgacatcca atccggacga ta                                  152

<210> SEQ ID NO 126
<211> LENGTH: 152
<212> TYPE: DNA
<213> ORGANISM: Artificial Sequence
<220> FEATURE:
<223> OTHER INFORMATION: target_4X_oligo_124

<400> SEQUENCE: 126
gaatcctagt acaagtggcc ggtctctggg ctggctggtg cccggagacg agctcgattt      60
cggcccagag ggggtaacca ctgctgctgg cgacttgtca atgtttctga aatatttccc     120
ggagaggaga ccgacatcca atccggacga ta                                  152

<210> SEQ ID NO 127
<211> LENGTH: 152
<212> TYPE: DNA
<213> ORGANISM: Artificial Sequence
<220> FEATURE:
<223> OTHER INFORMATION: target_4X_oligo_125

<400> SEQUENCE: 127
gaatcctagt acaagtggcc ggtctcgctc gatttcggcc cagaggggt aaccactgct      60 gctggcgact tgtcaatgtt tctgaaatat ttcccggaga ggcactgggt agtgacaggg     120
tttgaggaga ccgacatcca atccggacga ta                                  152

<210> SEQ ID NO 128
<211> LENGTH: 152
<212> TYPE: DNA
```

<213> ORGANISM: Artificial Sequence
<220> FEATURE:
<223> OTHER INFORMATION: target_4X_oligo_126

<400> SEQUENCE: 128

```
gaatcctagt acaagtggcc ggtctcacca ctgctgctgg cgacttgtca atgtttctga      60
aatatttccc ggagaggcac tgggtagtga cagggtttga ggatgacaaa cgcattaacc     120
tgaaacgaga ccgacatcca atccggacga ta                                   152
```

<210> SEQ ID NO 129
<211> LENGTH: 152
<212> TYPE: DNA
<213> ORGANISM: Artificial Sequence
<220> FEATURE:
<223> OTHER INFORMATION: target_4X_oligo_127

<400> SEQUENCE: 129

```
gaatcctagt acaagtggcc ggtctctgtt tctgaaatat ttcccggaga ggcactgggt      60
agtgacaggg tttgaggatg acaaacgcat taacctgaaa cctgcatttc tgtctgccga     120
acaggcgaga ccgacatcca atccggacga ta                                   152
```

<210> SEQ ID NO 130
<211> LENGTH: 152
<212> TYPE: DNA
<213> ORGANISM: Artificial Sequence
<220> FEATURE:
<223> OTHER INFORMATION: target_4X_oligo_128

<400> SEQUENCE: 130

```
gaatcctagt acaagtggcc ggtctcgcac tgggtagtga cagggtttga ggatgacaaa      60
cgcattaacc tgaaacctgc atttctgtct gccgaacagg ccgaggttct ccgcacagag     120
aggtctgaga ccgacatcca atccggacga ta                                   152
```

<210> SEQ ID NO 131
<211> LENGTH: 152
<212> TYPE: DNA
<213> ORGANISM: Artificial Sequence
<220> FEATURE:
<223> OTHER INFORMATION: target_4X_oligo_129

<400> SEQUENCE: 131

```
gaatcctagt acaagtggcc ggtctcgatg acaaacgcat taacctgaaa cctgcatttc      60
tgtctgccga acaggccgag gttctccgca cagagaggtc tgaccggcct gatactctga     120
ccgaaggaga ccgacatcca atccggacga ta                                   152
```

<210> SEQ ID NO 132
<211> LENGTH: 152
<212> TYPE: DNA
<213> ORGANISM: Artificial Sequence
<220> FEATURE:
<223> OTHER INFORMATION: target_4X_oligo_130

<400> SEQUENCE: 132

```
gaatcctagt acaagtggcc ggtctcctgc atttctgtct gccgaacagg ccgaggttct      60
ccgcacagag aggtctgacc ggcctgatac tctgaccgaa gccggcgaga ttctcgccca     120
gttttttgaga ccgacatcca atccggacga ta                                  152
```

<210> SEQ ID NO 133
<211> LENGTH: 152

```
<212> TYPE: DNA
<213> ORGANISM: Artificial Sequence
<220> FEATURE:
<223> OTHER INFORMATION: target_4X_oligo_131

<400> SEQUENCE: 133
gaatcctagt acaagtggcc ggtctccgag gttctccgca cagagaggtc tgaccggcct      60
gatactctga ccgaagccgg cgagattctc gcccagtttt tccctcgctg ttggcgggct     120
accgttgaga ccgacatcca atccggacga ta                                   152

<210> SEQ ID NO 134
<211> LENGTH: 152
<212> TYPE: DNA
<213> ORGANISM: Artificial Sequence
<220> FEATURE:
<223> OTHER INFORMATION: target_4X_oligo_132

<400> SEQUENCE: 134
gaatcctagt acaagtggcc ggtctcgacc ggcctgatac tctgaccgaa gccggcgaga      60
ttctcgccca gttttccct cgctgttggc gggctaccgt tgcgaaggtg ctctgtcacc     120
caggccgaga ccgacatcca atccggacga ta                                   152

<210> SEQ ID NO 135
<211> LENGTH: 152
<212> TYPE: DNA
<213> ORGANISM: Artificial Sequence
<220> FEATURE:
<223> OTHER INFORMATION: target_4X_oligo_133

<400> SEQUENCE: 135
gaatcctagt acaagtggcc ggtctcccgg cgagattctc gcccagtttt tccctcgctg      60
ttggcgggct accgttgcga aggtgctctg tcacccaggc ctgaccgtga tccggcgcac    120
ggctctgaga ccgacatcca atccggacga ta                                   152

<210> SEQ ID NO 136
<211> LENGTH: 152
<212> TYPE: DNA
<213> ORGANISM: Artificial Sequence
<220> FEATURE:
<223> OTHER INFORMATION: target_4X_oligo_134

<400> SEQUENCE: 136
gaatcctagt acaagtggcc ggtctcccct cgctgttggc gggctaccgt tgcgaaggtg      60
ctctgtcacc caggcctgac cgtgatccgg cgcacggctc tggggcaacc tcgatggcgc    120
cggggcgaga ccgacatcca atccggacga ta                                   152

<210> SEQ ID NO 137
<211> LENGTH: 152
<212> TYPE: DNA
<213> ORGANISM: Artificial Sequence
<220> FEATURE:
<223> OTHER INFORMATION: target_4X_oligo_135

<400> SEQUENCE: 137
gaatcctagt acaagtggcc ggtctcgcga aggtgctctg tcacccaggc ctgaccgtga      60
tccggcgcac ggctctgggg caacctcgat ggcgccgggg ccatctgcca tatagttggc    120
gaccctgaga ccgacatcca atccggacga ta                                   152

<210> SEQ ID NO 138
```

<211> LENGTH: 152
<212> TYPE: DNA
<213> ORGANISM: Artificial Sequence
<220> FEATURE:
<223> OTHER INFORMATION: target_4X_oligo_136

<400> SEQUENCE: 138
gaatcctagt acaagtggcc ggtctctgac cgtgatccgg cgcacggctc tggggcaacc      60
tcgatggcgc cggggccatc tgccatatag ttggcgaccc tggagcgccg acccttggag     120
cggcgggaga ccgacatcca atccggacga ta                                   152

<210> SEQ ID NO 139
<211> LENGTH: 152
<212> TYPE: DNA
<213> ORGANISM: Artificial Sequence
<220> FEATURE:
<223> OTHER INFORMATION: target_4X_oligo_137

<400> SEQUENCE: 139
gaatcctagt acaagtggcc ggtctcgggg caacctcgat ggcgccgggg ccatctgcca      60
tatagttggc gaccctggag cgccgaccct tggagcggcg aaccctag cagggctgac     120 cccaaggaga ccgacatcca atccggacga ta                                   152

<210> SEQ ID NO 140
<211> LENGTH: 152
<212> TYPE: DNA
<213> ORGANISM: Artificial Sequence
<220> FEATURE:
<223> OTHER INFORMATION: target_4X_oligo_138

<400> SEQUENCE: 140
gaatcctagt acaagtggcc ggtctccatc tgccatatag ttggcgaccc tggagcgccg      60
acccttggag cggcggaacc cctagcaggg ctgaccccaa gaagaagagg aaggtgaggt     120
ccggcggaga ccgacatcca atccggacga ta                                   152

<210> SEQ ID NO 141
<211> LENGTH: 152
<212> TYPE: DNA
<213> ORGANISM: Artificial Sequence
<220> FEATURE:
<223> OTHER INFORMATION: target_4X_oligo_139

<400> SEQUENCE: 141
gaatcctagt acaagtggcc ggtctcggag cgccgaccct tggagcggcg aaccccctag      60
cagggctgac cccaagaaga agaggaaggt gaggtccggc ggcggagagg gcagaggaag     120
tcttctgaga ccgacatcca atccggacga ta                                   152

<210> SEQ ID NO 142
<211> LENGTH: 152
<212> TYPE: DNA
<213> ORGANISM: Artificial Sequence
<220> FEATURE:
<223> OTHER INFORMATION: target_10X_oligo_001

<400> SEQUENCE: 142
gaatcctagt acaagtggcc ggtctcagct cctgggcaac gtgctggtta ttgtgctgtc      60
tcatcatttt ggcaaagaat cgcggccgc caccatgggg ggttcagagg tcggtaccgt     120
gccggtgaga ccgacatcca atccggacga ta                                   152

```
<210> SEQ ID NO 143
<211> LENGTH: 152
<212> TYPE: DNA
<213> ORGANISM: Artificial Sequence
<220> FEATURE:
<223> OTHER INFORMATION: target_10X_oligo_002

<400> SEQUENCE: 143
gaatcctagt acaagtggcc ggtctccaac gtgctggtta ttgtgctgtc tcatcatttt      60
ggcaaagaat tcgcggccgc caccatgggg ggttcagagg tcggtaccgt gccggtaacc     120
tggcgggaga ccgacatcca atccggacga ta                                   152

<210> SEQ ID NO 144
<211> LENGTH: 152
<212> TYPE: DNA
<213> ORGANISM: Artificial Sequence
<220> FEATURE:
<223> OTHER INFORMATION: target_10X_oligo_003

<400> SEQUENCE: 144
gaatcctagt acaagtggcc ggtctcgtta ttgtgctgtc tcatcatttt ggcaaagaat      60
tcgcggccgc caccatgggg ggttcagagg tcggtaccgt gccggtaacc tggcggctcg     120
gcgtgggaga ccgacatcca atccggacga ta                                   152

<210> SEQ ID NO 145
<211> LENGTH: 152
<212> TYPE: DNA
<213> ORGANISM: Artificial Sequence
<220> FEATURE:
<223> OTHER INFORMATION: target_10X_oligo_004

<400> SEQUENCE: 145
gaatcctagt acaagtggcc ggtctctgtc tcatcatttt ggcaaagaat tcgcggccgc      60
caccatgggg ggttcagagg tcggtaccgt gccggtaacc tggcggctcg gcgtggacgt     120
gggggagaga ccgacatcca atccggacga ta                                   152

<210> SEQ ID NO 146
<211> LENGTH: 152
<212> TYPE: DNA
<213> ORGANISM: Artificial Sequence
<220> FEATURE:
<223> OTHER INFORMATION: target_10X_oligo_005

<400> SEQUENCE: 146
gaatcctagt acaagtggcc ggtctctttt ggcaaagaat tcgcggccgc caccatgggg      60
ggttcagagg tcggtaccgt gccggtaacc tggcggctcg gcgtggacgt gggggaaaga     120
tcaatcgaga ccgacatcca atccggacga ta                                   152

<210> SEQ ID NO 147
<211> LENGTH: 152
<212> TYPE: DNA
<213> ORGANISM: Artificial Sequence
<220> FEATURE:
<223> OTHER INFORMATION: target_10X_oligo_006

<400> SEQUENCE: 147
gaatcctagt acaagtggcc ggtctcgaat tcgcggccgc caccatgggg ggttcagagg      60
tcggtaccgt gccggtaacc tggcggctcg gcgtggacgt gggggaaaga tcaatcgggc     120
ttgctggaga ccgacatcca atccggacga ta                                   152
```

<210> SEQ ID NO 148
<211> LENGTH: 152
<212> TYPE: DNA
<213> ORGANISM: Artificial Sequence
<220> FEATURE:
<223> OTHER INFORMATION: target_10X_oligo_007

<400> SEQUENCE: 148
gaatcctagt acaagtggcc ggtctcccgc caccatgggg ggttcagagg tcggtaccgt    60
gccggtaacc tggcggctcg gcgtggacgt gggggaaaga tcaatcgggc ttgctgccgt   120
gtcatagaga ccgacatcca atccggacga ta                                 152

<210> SEQ ID NO 149
<211> LENGTH: 152
<212> TYPE: DNA
<213> ORGANISM: Artificial Sequence
<220> FEATURE:
<223> OTHER INFORMATION: target_10X_oligo_008

<400> SEQUENCE: 149
gaatcctagt acaagtggcc ggtctcgggg ggttcagagg tcggtaccgt gccggtaacc    60
tggcggctcg gcgtggacgt gggggaaaga tcaatcgggc ttgctgccgt gtcatatgaa   120
gaggacgaga ccgacatcca atccggacga ta                                 152

<210> SEQ ID NO 150
<211> LENGTH: 152
<212> TYPE: DNA
<213> ORGANISM: Artificial Sequence
<220> FEATURE:
<223> OTHER INFORMATION: target_10X_oligo_009

<400> SEQUENCE: 150
gaatcctagt acaagtggcc ggtctcgagg tcggtaccgt gccggtaacc tggcggctcg    60
gcgtggacgt gggggaaaga tcaatcgggc ttgctgccgt gtcatatgaa gaggacaagc   120
ctaagggaga ccgacatcca atccggacga ta                                 152

<210> SEQ ID NO 151
<211> LENGTH: 152
<212> TYPE: DNA
<213> ORGANISM: Artificial Sequence
<220> FEATURE:
<223> OTHER INFORMATION: target_10X_oligo_010

<400> SEQUENCE: 151
gaatcctagt acaagtggcc ggtctcccgt gccggtaacc tggcggctcg gcgtggacgt    60
gggggaaaga tcaatcgggc ttgctgccgt gtcatatgaa gaggacaagc ctaaggaaat   120
cttggcgaga ccgacatcca atccggacga ta                                 152

<210> SEQ ID NO 152
<211> LENGTH: 152
<212> TYPE: DNA
<213> ORGANISM: Artificial Sequence
<220> FEATURE:
<223> OTHER INFORMATION: target_10X_oligo_011

<400> SEQUENCE: 152
gaatcctagt acaagtggcc ggtctcaacc tggcggctcg gcgtggacgt gggggaaaga    60
tcaatcgggc ttgctgccgt gtcatatgaa gaggacaagc ctaaggaaat cttggctgca   120
gtgtccgaga ccgacatcca atccggacga ta                                 152

<210> SEQ ID NO 153
<211> LENGTH: 152
<212> TYPE: DNA
<213> ORGANISM: Artificial Sequence
<220> FEATURE:
<223> OTHER INFORMATION: target_10X_oligo_012

<400> SEQUENCE: 153
gaatcctagt acaagtggcc ggtctcctcg gcgtggacgt gggggaaaga tcaatcgggc    60
ttgctgccgt gtcatatgaa gaggacaagc ctaaggaaat cttggctgca gtgtcctgga   120
tccatggaga ccgacatcca atccggacga ta                                 152

<210> SEQ ID NO 154
<211> LENGTH: 152
<212> TYPE: DNA
<213> ORGANISM: Artificial Sequence
<220> FEATURE:
<223> OTHER INFORMATION: target_10X_oligo_013

<400> SEQUENCE: 154
gaatcctagt acaagtggcc ggtctcacgt gggggaaaga tcaatcgggc ttgctgccgt    60
gtcatatgaa gaggacaagc ctaaggaaat cttggctgca gtgtcctgga tccatgatgg   120
gggggtgaga ccgacatcca atccggacga ta                                 152

<210> SEQ ID NO 155
<211> LENGTH: 152
<212> TYPE: DNA
<213> ORGANISM: Artificial Sequence
<220> FEATURE:
<223> OTHER INFORMATION: target_10X_oligo_014

<400> SEQUENCE: 155
gaatcctagt acaagtggcc ggtctcaaga tcaatcgggc ttgctgccgt gtcatatgaa    60
gaggacaagc ctaaggaaat cttggctgca gtgtcctgga tccatgatgg gggggttggc   120
gatgaagaga ccgacatcca atccggacga ta                                 152

<210> SEQ ID NO 156
<211> LENGTH: 152
<212> TYPE: DNA
<213> ORGANISM: Artificial Sequence
<220> FEATURE:
<223> OTHER INFORMATION: target_10X_oligo_015

<400> SEQUENCE: 156
gaatcctagt acaagtggcc ggtctcgggc ttgctgccgt gtcatatgaa gaggacaagc    60
ctaaggaaat cttggctgca gtgtcctgga tccatgatgg gggggttggc gatgaacggt   120
ccgggggaga ccgacatcca atccggacga ta                                 152

<210> SEQ ID NO 157
<211> LENGTH: 152
<212> TYPE: DNA
<213> ORGANISM: Artificial Sequence
<220> FEATURE:
<223> OTHER INFORMATION: target_10X_oligo_016

<400> SEQUENCE: 157
gaatcctagt acaagtggcc ggtctcccgt gtcatatgaa gaggacaagc ctaaggaaat    60
cttggctgca gtgtcctgga tccatgatgg gggggttggc gatgaacggt ccggggcaag   120
tcgactgaga ccgacatcca atccggacga ta      152

<210> SEQ ID NO 158
<211> LENGTH: 152
<212> TYPE: DNA
<213> ORGANISM: Artificial Sequence
<220> FEATURE:
<223> OTHER INFORMATION: target_10X_oligo_017

<400> SEQUENCE: 158
gaatcctagt acaagtggcc ggtctctgaa gaggacaagc taaggaaat cttggctgca      60 gtgtcctgga tccatgatgg gggggttggc gatgaacggt ccggggcaag tcgacttgcc      120
ctccgagaga ccgacatcca atccggacga ta      152

<210> SEQ ID NO 159
<211> LENGTH: 152
<212> TYPE: DNA
<213> ORGANISM: Artificial Sequence
<220> FEATURE:
<223> OTHER INFORMATION: target_10X_oligo_018

<400> SEQUENCE: 159
gaatcctagt acaagtggcc ggtctcaagc taaggaaat cttggctgca gtgtcctgga      60
tccatgatgg gggggttggc gatgaacggt ccggggcaag tcgacttgcc ctccgaggca      120
tggcaagaga ccgacatcca atccggacga ta      152

<210> SEQ ID NO 160
<211> LENGTH: 152
<212> TYPE: DNA
<213> ORGANISM: Artificial Sequence
<220> FEATURE:
<223> OTHER INFORMATION: target_10X_oligo_019

<400> SEQUENCE: 160
gaatcctagt acaagtggcc ggtctcaaat cttggctgca gtgtcctgga tccatgatgg      60
gggggttggc gatgaacggt ccggggcaag tcgacttgcc ctccgaggca tggcaagaag      120
agcccggaga ccgacatcca atccggacga ta      152

<210> SEQ ID NO 161
<211> LENGTH: 152
<212> TYPE: DNA
<213> ORGANISM: Artificial Sequence
<220> FEATURE:
<223> OTHER INFORMATION: target_10X_oligo_020

<400> SEQUENCE: 161
gaatcctagt acaagtggcc ggtctctgca gtgtcctgga tccatgatgg gggggttggc      60
gatgaacggt ccggggcaag tcgacttgcc ctccgaggca tggcaagaag agcccgaagg      120
ctgcgcgaga ccgacatcca atccggacga ta      152

<210> SEQ ID NO 162
<211> LENGTH: 152
<212> TYPE: DNA
<213> ORGANISM: Artificial Sequence
<220> FEATURE:
<223> OTHER INFORMATION: target_10X_oligo_021

<400> SEQUENCE: 162
gaatcctagt acaagtggcc ggtctctgga tccatgatgg gggggttggc gatgaacggt      60
ccggggcaag tcgacttgcc ctccgaggca tggcaagaag agcccgaagg ctgcgccggt      120
ttaggagaga ccgacatcca atccggacga ta                                       152

<210> SEQ ID NO 163
<211> LENGTH: 152
<212> TYPE: DNA
<213> ORGANISM: Artificial Sequence
<220> FEATURE:
<223> OTHER INFORMATION: target_10X_oligo_022

<400> SEQUENCE: 163
gaatcctagt acaagtggcc ggtctcatgg ggggttggc gatgaacggt ccggggcaag          60
tcgacttgcc ctccgaggca tggcaagaag agcccgaagg ctgcgccggt ttaggagagc        120
ccgcctgaga ccgacatcca atccggacga ta                                      152

<210> SEQ ID NO 164
<211> LENGTH: 152
<212> TYPE: DNA
<213> ORGANISM: Artificial Sequence
<220> FEATURE:
<223> OTHER INFORMATION: target_10X_oligo_023

<400> SEQUENCE: 164
gaatcctagt acaagtggcc ggtctctggc gatgaacggt ccggggcaag tcgacttgcc          60
ctccgaggca tggcaagaag agcccgaagg ctgcgccggt ttaggagagc ccgcctccgc        120
gacctggaga ccgacatcca atccggacga ta                                      152

<210> SEQ ID NO 165
<211> LENGTH: 152
<212> TYPE: DNA
<213> ORGANISM: Artificial Sequence
<220> FEATURE:
<223> OTHER INFORMATION: target_10X_oligo_024

<400> SEQUENCE: 165
gaatcctagt acaagtggcc ggtctccggt ccggggcaag tcgacttgcc ctccgaggca          60
tggcaagaag agcccgaagg ctgcgccggt ttaggagagc ccgcctccgc gacctggaca        120
tgttgcgaga ccgacatcca atccggacga ta                                      152

<210> SEQ ID NO 166
<211> LENGTH: 152
<212> TYPE: DNA
<213> ORGANISM: Artificial Sequence
<220> FEATURE:
<223> OTHER INFORMATION: target_10X_oligo_025

<400> SEQUENCE: 166
gaatcctagt acaagtggcc ggtctccaag tcgacttgcc ctccgaggca tggcaagaag          60
agcccgaagg ctgcgccggt ttaggagagc ccgcctccgc gacctggaca tgttgctgag        120
tgagttgaga ccgacatcca atccggacga ta                                      152

<210> SEQ ID NO 167
<211> LENGTH: 152
<212> TYPE: DNA
<213> ORGANISM: Artificial Sequence
<220> FEATURE:
<223> OTHER INFORMATION: target_10X_oligo_026

<400> SEQUENCE: 167
gaatcctagt acaagtggcc ggtctctgcc ctccgaggca tggcaagaag agcccgaagg          60

| | |
|---|---|
| ctgcgccggt ttaggagagc ccgcctccgc gacctggaca tgttgctgag tgagttggga | 120 |
| tggaccgaga ccgacatcca atccggacga ta | 152 |

<210> SEQ ID NO 168
<211> LENGTH: 152
<212> TYPE: DNA
<213> ORGANISM: Artificial Sequence
<220> FEATURE:
<223> OTHER INFORMATION: target_10X_oligo_027

<400> SEQUENCE: 168

| | |
|---|---|
| gaatcctagt acaagtggcc ggtctcggca tggcaagaag agcccgaagg ctgcgccggt | 60 |
| ttaggagagc ccgcctccgc gacctggaca tgttgctgag tgagttggga tggaccccccc | 120 |
| tccctggaga ccgacatcca atccggacga ta | 152 |

<210> SEQ ID NO 169
<211> LENGTH: 152
<212> TYPE: DNA
<213> ORGANISM: Artificial Sequence
<220> FEATURE:
<223> OTHER INFORMATION: target_10X_oligo_028

<400> SEQUENCE: 169

| | |
|---|---|
| gaatcctagt acaagtggcc ggtctcgaag agcccgaagg ctgcgccggt ttaggagagc | 60 |
| ccgcctccgc gacctggaca tgttgctgag tgagttggga tggaccccccc tccctgacaa | 120 |
| aaacgtgaga ccgacatcca atccggacga ta | 152 |

<210> SEQ ID NO 170
<211> LENGTH: 152
<212> TYPE: DNA
<213> ORGANISM: Artificial Sequence
<220> FEATURE:
<223> OTHER INFORMATION: target_10X_oligo_029

<400> SEQUENCE: 170

| | |
|---|---|
| gaatcctagt acaagtggcc ggtctcaagg ctgcgccggt ttaggagagc ccgcctccgc | 60 |
| gacctggaca tgttgctgag tgagttggga tggaccccccc tccctgacaa aaacgtctca | 120 |
| ccagttgaga ccgacatcca atccggacga ta | 152 |

<210> SEQ ID NO 171
<211> LENGTH: 152
<212> TYPE: DNA
<213> ORGANISM: Artificial Sequence
<220> FEATURE:
<223> OTHER INFORMATION: target_10X_oligo_030

<400> SEQUENCE: 171

| | |
|---|---|
| gaatcctagt acaagtggcc ggtctccggt ttaggagagc ccgcctccgc gacctggaca | 60 |
| tgttgctgag tgagttggga tggaccccccc tccctgacaa aaacgtctca ccagttgatg | 120 |
| cctggcgaga ccgacatcca atccggacga ta | 152 |

<210> SEQ ID NO 172
<211> LENGTH: 152
<212> TYPE: DNA
<213> ORGANISM: Artificial Sequence
<220> FEATURE:
<223> OTHER INFORMATION: target_10X_oligo_031

<400> SEQUENCE: 172

| | |
|---|---|
| gaatcctagt acaagtggcc ggtctcgagc ccgcctccgc gacctggaca tgttgctgag | 60 | tgagttggga tggaccccccc tccctgacaa aaacgtctca ccagttgatg cctggctggc    120 acgcaagaga ccgacatcca atccggacga ta                                  152

<210> SEQ ID NO 173
<211> LENGTH: 152
<212> TYPE: DNA
<213> ORGANISM: Artificial Sequence
<220> FEATURE:
<223> OTHER INFORMATION: target_10X_oligo_032

<400> SEQUENCE: 173
gaatcctagt acaagtggcc ggtctcccgc gacctggaca tgttgctgag tgagttggga    60
tggacccccc tccctgacaa aaacgtctca ccagttgatg cctggctggc acgcaaaaga    120
ctggccgaga ccgacatcca atccggacga ta                                  152

<210> SEQ ID NO 174
<211> LENGTH: 152
<212> TYPE: DNA
<213> ORGANISM: Artificial Sequence
<220> FEATURE:
<223> OTHER INFORMATION: target_10X_oligo_033

<400> SEQUENCE: 174
gaatcctagt acaagtggcc ggtctcgaca tgttgctgag tgagttggga tggacccccc    60
tccctgacaa aaacgtctca ccagttgatg cctggctggc acgcaaaaga ctggccgagg    120
aatatggaga ccgacatcca atccggacga ta                                  152

<210> SEQ ID NO 175
<211> LENGTH: 152
<212> TYPE: DNA
<213> ORGANISM: Artificial Sequence
<220> FEATURE:
<223> OTHER INFORMATION: target_10X_oligo_034

<400> SEQUENCE: 175
gaatcctagt acaagtggcc ggtctctgag tgagttggga tggacccccc tccctgacaa    60
aaacgtctca ccagttgatg cctggctggc acgcaaaaga ctggccgagg aatatgtggt    120
ggatgagaga ccgacatcca atccggacga ta                                  152

<210> SEQ ID NO 176
<211> LENGTH: 152
<212> TYPE: DNA
<213> ORGANISM: Artificial Sequence
<220> FEATURE:
<223> OTHER INFORMATION: target_10X_oligo_035

<400> SEQUENCE: 176
gaatcctagt acaagtggcc ggtctcggga tggacccccc tccctgacaa aaacgtctca    60
ccagttgatg cctggctggc acgcaaaaga ctggccgagg aatatgtggt ggatgaaact    120
gagagggaga ccgacatcca atccggacga ta                                  152

<210> SEQ ID NO 177
<211> LENGTH: 152
<212> TYPE: DNA
<213> ORGANISM: Artificial Sequence
<220> FEATURE:
<223> OTHER INFORMATION: target_10X_oligo_036

<400> SEQUENCE: 177

```
gaatcctagt acaagtggcc ggtctccccc tccctgacaa aaacgtctca ccagttgatg      60
cctggctggc acgcaaaaga ctggccgagg aatatgtggt ggatgaaact gagaggcgaa     120
gactgcgaga ccgacatcca atccggacga ta                                   152
```

```
<210> SEQ ID NO 178
<211> LENGTH: 152
<212> TYPE: DNA
<213> ORGANISM: Artificial Sequence
<220> FEATURE:
<223> OTHER INFORMATION: target_10X_oligo_037

<400> SEQUENCE: 178
```

```
gaatcctagt acaagtggcc ggtctcacaa aaacgtctca ccagttgatg cctggctggc      60
acgcaaaaga ctggccgagg aatatgtggt ggatgaaact gagaggcgaa gactgctggg     120
ctacgcgaga ccgacatcca atccggacga ta                                   152
```

```
<210> SEQ ID NO 179
<211> LENGTH: 152
<212> TYPE: DNA
<213> ORGANISM: Artificial Sequence
<220> FEATURE:
<223> OTHER INFORMATION: target_10X_oligo_038

<400> SEQUENCE: 179
```

```
gaatcctagt acaagtggcc ggtctcctca ccagttgatg cctggctggc acgcaaaaga      60
ctggccgagg aatatgtggt ggatgaaact gagaggcgaa gactgctggg ctacgccgtg     120
tctcatgaga ccgacatcca atccggacga ta                                   152
```

```
<210> SEQ ID NO 180
<211> LENGTH: 152
<212> TYPE: DNA
<213> ORGANISM: Artificial Sequence
<220> FEATURE:
<223> OTHER INFORMATION: target_10X_oligo_039

<400> SEQUENCE: 180
```

```
gaatcctagt acaagtggcc ggtctcgatg cctggctggc acgcaaaaga ctggccgagg      60
aatatgtggt ggatgaaact gagaggcgaa gactgctggg ctacgccgtg tctcatatgg     120
cccggcgaga ccgacatcca atccggacga ta                                   152
```

```
<210> SEQ ID NO 181
<211> LENGTH: 152
<212> TYPE: DNA
<213> ORGANISM: Artificial Sequence
<220> FEATURE:
<223> OTHER INFORMATION: target_10X_oligo_040

<400> SEQUENCE: 181
```

```
gaatcctagt acaagtggcc ggtctctggc acgcaaaaga ctggccgagg aatatgtggt      60
ggatgaaact gagaggcgaa gactgctggg ctacgccgtg tctcatatgg cccggcaccg     120
agggtggaga ccgacatcca atccggacga ta                                   152
```

```
<210> SEQ ID NO 182
<211> LENGTH: 152
<212> TYPE: DNA
<213> ORGANISM: Artificial Sequence
<220> FEATURE:
<223> OTHER INFORMATION: target_10X_oligo_041

<400> SEQUENCE: 182
```
gaatcctagt acaagtggcc ggtctcaaga ctggccgagg aatatgtggt ggatgaaact      60
gagaggcgaa gactgctggg ctacgccgtg tctcatatgg cccggcaccg agggtggcgc     120
aatccagaga ccgacatcca atccggacga ta                                   152

<210> SEQ ID NO 183
<211> LENGTH: 152
<212> TYPE: DNA
<213> ORGANISM: Artificial Sequence
<220> FEATURE:
<223> OTHER INFORMATION: target_10X_oligo_042

<400> SEQUENCE: 183
gaatcctagt acaagtggcc ggtctcgagg aatatgtggt ggatgaaact gagaggcgaa      60
gactgctggg ctacgccgtg tctcatatgg cccggcaccg agggtggcgc aatccatgga     120
ctacgagaga ccgacatcca atccggacga ta                                   152

<210> SEQ ID NO 184
<211> LENGTH: 152
<212> TYPE: DNA
<213> ORGANISM: Artificial Sequence
<220> FEATURE:
<223> OTHER INFORMATION: target_10X_oligo_043

<400> SEQUENCE: 184
gaatcctagt acaagtggcc ggtctctggt ggatgaaact gagaggcgaa gactgctggg      60
ctacgccgtg tctcatatgg cccggcaccg agggtggcgc aatccatgga ctacgattaa     120
ggacctgaga ccgacatcca atccggacga ta                                   152

<210> SEQ ID NO 185
<211> LENGTH: 152
<212> TYPE: DNA
<213> ORGANISM: Artificial Sequence
<220> FEATURE:
<223> OTHER INFORMATION: target_10X_oligo_044

<400> SEQUENCE: 185
gaatcctagt acaagtggcc ggtctcaact gagaggcgaa gactgctggg ctacgccgtg      60
tctcatatgg cccggcaccg agggtggcgc aatccatgga ctacgattaa ggacctgaaa     120
aatctggaga ccgacatcca atccggacga ta                                   152

<210> SEQ ID NO 186
<211> LENGTH: 152
<212> TYPE: DNA
<213> ORGANISM: Artificial Sequence
<220> FEATURE:
<223> OTHER INFORMATION: target_10X_oligo_045

<400> SEQUENCE: 186
gaatcctagt acaagtggcc ggtctccgaa gactgctggg ctacgccgtg tctcatatgg      60
cccggcaccg agggtggcgc aatccatgga ctacgattaa ggacctgaaa aatctgccac     120
agccctgaga ccgacatcca atccggacga ta                                   152

<210> SEQ ID NO 187
<211> LENGTH: 152
<212> TYPE: DNA
<213> ORGANISM: Artificial Sequence
<220> FEATURE:
<223> OTHER INFORMATION: target_10X_oligo_046

```
<400> SEQUENCE: 187
gaatcctagt acaagtggcc ggtctctggg ctacgccgtg tctcatatgg cccggcaccg       60
agggtggcgc aatccatgga ctacgattaa ggacctgaaa aatctgccac agccctcaga      120
ctcatggaga ccgacatcca atccggacga ta                                    152

<210> SEQ ID NO 188
<211> LENGTH: 152
<212> TYPE: DNA
<213> ORGANISM: Artificial Sequence
<220> FEATURE:
<223> OTHER INFORMATION: target_10X_oligo_047

<400> SEQUENCE: 188
gaatcctagt acaagtggcc ggtctccgtg tctcatatgg cccggcaccg agggtggcgc       60
aatccatgga ctacgattaa ggacctgaaa aatctgccac agccctcaga ctcatgggag      120
cggactgaga ccgacatcca atccggacga ta                                    152

<210> SEQ ID NO 189
<211> LENGTH: 152
<212> TYPE: DNA
<213> ORGANISM: Artificial Sequence
<220> FEATURE:
<223> OTHER INFORMATION: target_10X_oligo_048

<400> SEQUENCE: 189
gaatcctagt acaagtggcc ggtctcatgg cccggcaccg agggtggcgc aatccatgga       60
ctacgattaa ggacctgaaa aatctgccac agccctcaga ctcatgggag cggactagag      120
agtcacgaga ccgacatcca atccggacga ta                                    152

<210> SEQ ID NO 190
<211> LENGTH: 152
<212> TYPE: DNA
<213> ORGANISM: Artificial Sequence
<220> FEATURE:
<223> OTHER INFORMATION: target_10X_oligo_049

<400> SEQUENCE: 190
gaatcctagt acaagtggcc ggtctcaccg agggtggcgc aatccatgga ctacgattaa       60
ggacctgaaa aatctgccac agccctcaga ctcatgggag cggactagag agtcactgga      120
agccaggaga ccgacatcca atccggacga ta                                    152

<210> SEQ ID NO 191
<211> LENGTH: 152
<212> TYPE: DNA
<213> ORGANISM: Artificial Sequence
<220> FEATURE:
<223> OTHER INFORMATION: target_10X_oligo_050

<400> SEQUENCE: 191
gaatcctagt acaagtggcc ggtctcgcgc aatccatgga ctacgattaa ggacctgaaa       60
aatctgccac agccctcaga ctcatgggag cggactagag agtcactgga agccaggtat      120
agcgtggaga ccgacatcca atccggacga ta                                    152

<210> SEQ ID NO 192
<211> LENGTH: 152
<212> TYPE: DNA
<213> ORGANISM: Artificial Sequence
<220> FEATURE:
<223> OTHER INFORMATION: target_10X_oligo_051
```

<400> SEQUENCE: 192
gaatcctagt acaagtggcc ggtctctgga ctacgattaa ggacctgaaa aatctgccac      60
agccctcaga ctcatgggag cggactagag agtcactgga agccaggtat agcgtgtctc     120
tggagcgaga ccgacatcca atccggacga ta                                   152

<210> SEQ ID NO 193
<211> LENGTH: 152
<212> TYPE: DNA
<213> ORGANISM: Artificial Sequence
<220> FEATURE:
<223> OTHER INFORMATION: target_10X_oligo_052

<400> SEQUENCE: 193
gaatcctagt acaagtggcc ggtctcttaa ggacctgaaa aatctgccac agccctcaga      60
ctcatgggag cggactagag agtcactgga agccaggtat agcgtgtctc tggagcccgg    120
cactgtgaga ccgacatcca atccggacga ta                                   152

<210> SEQ ID NO 194
<211> LENGTH: 152
<212> TYPE: DNA
<213> ORGANISM: Artificial Sequence
<220> FEATURE:
<223> OTHER INFORMATION: target_10X_oligo_053

<400> SEQUENCE: 194
gaatcctagt acaagtggcc ggtctcgaaa aatctgccac agccctcaga ctcatgggag      60
cggactagag agtcactgga agccaggtat agcgtgtctc tggagcccgg cactgtcggg    120
caatgggaga ccgacatcca atccggacga ta                                   152

<210> SEQ ID NO 195
<211> LENGTH: 152
<212> TYPE: DNA
<213> ORGANISM: Artificial Sequence
<220> FEATURE:
<223> OTHER INFORMATION: target_10X_oligo_054

<400> SEQUENCE: 195
gaatcctagt acaagtggcc ggtctcccac agccctcaga ctcatgggag cggactagag      60
agtcactgga agccaggtat agcgtgtctc tggagcccgg cactgtcggg caatgggcag    120
gctatcgaga ccgacatcca atccggacga ta                                   152

<210> SEQ ID NO 196
<211> LENGTH: 152
<212> TYPE: DNA
<213> ORGANISM: Artificial Sequence
<220> FEATURE:
<223> OTHER INFORMATION: target_10X_oligo_055

<400> SEQUENCE: 196
gaatcctagt acaagtggcc ggtctccaga ctcatgggag cggactagag agtcactgga      60
agccaggtat agcgtgtctc tggagcccgg cactgtcggg caatgggcag gctatcttct    120
gcagaggaga ccgacatcca atccggacga ta                                   152

<210> SEQ ID NO 197
<211> LENGTH: 152
<212> TYPE: DNA
<213> ORGANISM: Artificial Sequence
<220> FEATURE:

<223> OTHER INFORMATION: target_10X_oligo_056

<400> SEQUENCE: 197
gaatcctagt acaagtggcc ggtctcggag cggactagag agtcactgga agccaggtat    60
agcgtgtctc tggagcccgg cactgtcggg caatgggcag gctatcttct gcagagagca   120
ccgggcgaga ccgacatcca atccggacga ta                                 152

<210> SEQ ID NO 198
<211> LENGTH: 152
<212> TYPE: DNA
<213> ORGANISM: Artificial Sequence
<220> FEATURE:
<223> OTHER INFORMATION: target_10X_oligo_057

<400> SEQUENCE: 198
gaatcctagt acaagtggcc ggtctcagag agtcactgga agccaggtat agcgtgtctc    60
tggagcccgg cactgtcggg caatgggcag gctatcttct gcagagagca ccgggcataa   120
gacttagaga ccgacatcca atccggacga ta                                 152

<210> SEQ ID NO 199
<211> LENGTH: 152
<212> TYPE: DNA
<213> ORGANISM: Artificial Sequence
<220> FEATURE:
<223> OTHER INFORMATION: target_10X_oligo_058

<400> SEQUENCE: 199
gaatcctagt acaagtggcc ggtctctgga agccaggtat agcgtgtctc tggagcccgg    60
cactgtcggg caatgggcag gctatcttct gcagagagca ccgggcataa gacttaatcc   120
cacacagaga ccgacatcca atccggacga ta                                 152

<210> SEQ ID NO 200
<211> LENGTH: 152
<212> TYPE: DNA
<213> ORGANISM: Artificial Sequence
<220> FEATURE:
<223> OTHER INFORMATION: target_10X_oligo_059

<400> SEQUENCE: 200
gaatcctagt acaagtggcc ggtctcgtat agcgtgtctc tggagcccgg cactgtcggg    60
caatgggcag gctatcttct gcagagagca ccgggcataa gacttaatcc cacacaacag   120
tccgccgaga ccgacatcca atccggacga ta                                 152

<210> SEQ ID NO 201
<211> LENGTH: 152
<212> TYPE: DNA
<213> ORGANISM: Artificial Sequence
<220> FEATURE:
<223> OTHER INFORMATION: target_10X_oligo_060

<400> SEQUENCE: 201
gaatcctagt acaagtggcc ggtctctctc tggagcccgg cactgtcggg caatgggcag    60
gctatcttct gcagagagca ccgggcataa gacttaatcc cacacaacag tccgccggtc   120 gaagggaga ccgacatcca atccggacga ta                                  152

<210> SEQ ID NO 202
<211> LENGTH: 152
<212> TYPE: DNA
<213> ORGANISM: Artificial Sequence

```
<220> FEATURE:
<223> OTHER INFORMATION: target_10X_oligo_061

<400> SEQUENCE: 202
gaatcctagt acaagtggcc ggtctcccgg cactgtcggg caatgggcag gctatcttct    60
gcagagagca ccgggcataa gacttaatcc cacacaacag tccgccggtc gaagggccga   120
gttgaggaga ccgacatcca atccggacga ta                                 152

<210> SEQ ID NO 203
<211> LENGTH: 152
<212> TYPE: DNA
<213> ORGANISM: Artificial Sequence
<220> FEATURE:
<223> OTHER INFORMATION: target_10X_oligo_062

<400> SEQUENCE: 203
gaatcctagt acaagtggcc ggtctccggg caatgggcag gctatcttct gcagagagca    60
ccgggcataa gacttaatcc cacacaacag tccgccggtc gaagggccga gttgagtaac   120
gcaacagaga ccgacatcca atccggacga ta                                 152

<210> SEQ ID NO 204
<211> LENGTH: 152
<212> TYPE: DNA
<213> ORGANISM: Artificial Sequence
<220> FEATURE:
<223> OTHER INFORMATION: target_10X_oligo_063

<400> SEQUENCE: 204
gaatcctagt acaagtggcc ggtctcgcag gctatcttct gcagagagca ccgggcataa    60
gacttaatcc cacacaacag tccgccggtc gaagggccga gttgagtaac gcaacagcct   120
ttgagagaga ccgacatcca atccggacga ta                                 152

<210> SEQ ID NO 205
<211> LENGTH: 152
<212> TYPE: DNA
<213> ORGANISM: Artificial Sequence
<220> FEATURE:
<223> OTHER INFORMATION: target_10X_oligo_064

<400> SEQUENCE: 205
gaatcctagt acaagtggcc ggtctcttct gcagagagca ccgggcataa gacttaatcc    60
cacacaacag tccgccggtc gaagggccga gttgagtaac gcaacagcct ttgagacaag   120
actgcggaga ccgacatcca atccggacga ta                                 152

<210> SEQ ID NO 206
<211> LENGTH: 152
<212> TYPE: DNA
<213> ORGANISM: Artificial Sequence
<220> FEATURE:
<223> OTHER INFORMATION: target_10X_oligo_065

<400> SEQUENCE: 206
gaatcctagt acaagtggcc ggtctcagca ccgggcataa gacttaatcc cacacaacag    60
tccgccggtc gaagggccga gttgagtaac gcaacagcct ttgagacaag actgcgacaa   120
gaagacgaga ccgacatcca atccggacga ta                                 152

<210> SEQ ID NO 207
<211> LENGTH: 152
<212> TYPE: DNA
```

```
<213> ORGANISM: Artificial Sequence
<220> FEATURE:
<223> OTHER INFORMATION: target_10X_oligo_066

<400> SEQUENCE: 207
gaatcctagt acaagtggcc ggtctcataa gacttaatcc cacacaacag tccgccggtc    60
gaagggccga gttgagtaac gcaacagcct ttgagacaag actgcgacaa gaagacgtcc   120
tttggggaga ccgacatcca atccggacga ta                                 152

<210> SEQ ID NO 208
<211> LENGTH: 152
<212> TYPE: DNA
<213> ORGANISM: Artificial Sequence
<220> FEATURE:
<223> OTHER INFORMATION: target_10X_oligo_067

<400> SEQUENCE: 208
gaatcctagt acaagtggcc ggtctcatcc cacacaacag tccgccggtc gaagggccga    60
gttgagtaac gcaacagcct ttgagacaag actgcgacaa gaagacgtcc tttgggaact   120
gagatggaga ccgacatcca atccggacga ta                                 152

<210> SEQ ID NO 209
<211> LENGTH: 152
<212> TYPE: DNA
<213> ORGANISM: Artificial Sequence
<220> FEATURE:
<223> OTHER INFORMATION: target_10X_oligo_068

<400> SEQUENCE: 209
gaatcctagt acaagtggcc ggtctcacag tccgccggtc gaagggccga gttgagtaac    60
gcaacagcct ttgagacaag actgcgacaa gaagacgtcc tttgggaact gagatgcatc   120
gccgatgaga ccgacatcca atccggacga ta                                 152

<210> SEQ ID NO 210
<211> LENGTH: 152
<212> TYPE: DNA
<213> ORGANISM: Artificial Sequence
<220> FEATURE:
<223> OTHER INFORMATION: target_10X_oligo_069

<400> SEQUENCE: 210
gaatcctagt acaagtggcc ggtctcggtc gaagggccga gttgagtaac gcaacagcct    60
ttgagacaag actgcgacaa gaagacgtcc tttgggaact gagatgcatc gccgatgtgc   120
aagggtgaga ccgacatcca atccggacga ta                                 152

<210> SEQ ID NO 211
<211> LENGTH: 152
<212> TYPE: DNA
<213> ORGANISM: Artificial Sequence
<220> FEATURE:
<223> OTHER INFORMATION: target_10X_oligo_070

<400> SEQUENCE: 211
gaatcctagt acaagtggcc ggtctcccga gttgagtaac gcaacagcct ttgagacaag    60
actgcgacaa gaagacgtcc tttgggaact gagatgcatc gccgatgtgc aagggttgcc   120
cgaggagaga ccgacatcca atccggacga ta                                 152

<210> SEQ ID NO 212
<211> LENGTH: 152
```

```
<212> TYPE: DNA
<213> ORGANISM: Artificial Sequence
<220> FEATURE:
<223> OTHER INFORMATION: target_10X_oligo_071

<400> SEQUENCE: 212
gaatcctagt acaagtggcc ggtctctaac gcaacagcct ttgagacaag actgcgacaa      60
gaagacgtcc tttgggaact gagatgcatc gccgatgtgc aagggttgcc cgaggacgtc     120
gttagcgaga ccgacatcca atccggacga ta                                   152

<210> SEQ ID NO 213
<211> LENGTH: 152
<212> TYPE: DNA
<213> ORGANISM: Artificial Sequence
<220> FEATURE:
<223> OTHER INFORMATION: target_10X_oligo_072

<400> SEQUENCE: 213
gaatcctagt acaagtggcc ggtctcgcct ttgagacaag actgcgacaa gaagacgtcc      60
tttgggaact gagatgcatc gccgatgtgc aagggttgcc cgaggacgtc gttagcaacg     120
ttataggaga ccgacatcca atccggacga ta                                   152

<210> SEQ ID NO 214
<211> LENGTH: 152
<212> TYPE: DNA
<213> ORGANISM: Artificial Sequence
<220> FEATURE:
<223> OTHER INFORMATION: target_10X_oligo_073

<400> SEQUENCE: 214
gaatcctagt acaagtggcc ggtctccaag actgcgacaa gaagacgtcc tttgggaact      60
gagatgcatc gccgatgtgc aagggttgcc cgaggacgtc gttagcaacg ttatagacgc     120
agtgttgaga ccgacatcca atccggacga ta                                   152

<210> SEQ ID NO 215
<211> LENGTH: 152
<212> TYPE: DNA
<213> ORGANISM: Artificial Sequence
<220> FEATURE:
<223> OTHER INFORMATION: target_10X_oligo_074

<400> SEQUENCE: 215
gaatcctagt acaagtggcc ggtctcacaa gaagacgtcc tttgggaact gagatgcatc      60
gccgatgtgc aagggttgcc cgaggacgtc gttagcaacg ttatagacgc agtgttttgc     120
cagaaagaga ccgacatcca atccggacga ta                                   152

<210> SEQ ID NO 216
<211> LENGTH: 152
<212> TYPE: DNA
<213> ORGANISM: Artificial Sequence
<220> FEATURE:
<223> OTHER INFORMATION: target_10X_oligo_075

<400> SEQUENCE: 216
gaatcctagt acaagtggcc ggtctcgtcc tttgggaact gagatgcatc gccgatgtgc      60
aagggttgcc cgaggacgtc gttagcaacg ttatagacgc agtgttttgc cagaaacggc     120
cctccggaga ccgacatcca atccggacga ta                                   152

<210> SEQ ID NO 217
```

```
<211> LENGTH: 152
<212> TYPE: DNA
<213> ORGANISM: Artificial Sequence
<220> FEATURE:
<223> OTHER INFORMATION: target_10X_oligo_076

<400> SEQUENCE: 217
gaatcctagt acaagtggcc ggtctcaact gagatgcatc gccgatgtgc aagggttgcc      60
cgaggacgtc gttagcaacg ttatagacgc agtgttttgc cagaaacggc cctccgtacc     120
agcggagaga ccgacatcca atccggacga ta                                   152

<210> SEQ ID NO 218
<211> LENGTH: 152
<212> TYPE: DNA
<213> ORGANISM: Artificial Sequence
<220> FEATURE:
<223> OTHER INFORMATION: target_10X_oligo_077

<400> SEQUENCE: 218
gaatcctagt acaagtggcc ggtctccatc gccgatgtgc aagggttgcc cgaggacgtc      60
gttagcaacg ttatagacgc agtgttttgc cagaaacggc cctccgtacc agcggaaaga    120
atcggcgaga ccgacatcca atccggacga ta                                   152

<210> SEQ ID NO 219
<211> LENGTH: 152
<212> TYPE: DNA
<213> ORGANISM: Artificial Sequence
<220> FEATURE:
<223> OTHER INFORMATION: target_10X_oligo_078

<400> SEQUENCE: 219
gaatcctagt acaagtggcc ggtctcgtgc aagggttgcc cgaggacgtc gttagcaacg      60
ttatagacgc agtgttttgc cagaaacggc cctccgtacc agcggaaaga atcggcagag    120
atccgcgaga ccgacatcca atccggacga ta                                   152

<210> SEQ ID NO 220
<211> LENGTH: 152
<212> TYPE: DNA
<213> ORGANISM: Artificial Sequence
<220> FEATURE:
<223> OTHER INFORMATION: target_10X_oligo_079

<400> SEQUENCE: 220
gaatcctagt acaagtggcc ggtctctgcc cgaggacgtc gttagcaacg ttatagacgc      60
agtgttttgc cagaaacggc cctccgtacc agcggaaaga atcggcagag atccgctgga    120
ccccaggaga ccgacatcca atccggacga ta                                   152

<210> SEQ ID NO 221
<211> LENGTH: 152
<212> TYPE: DNA
<213> ORGANISM: Artificial Sequence
<220> FEATURE:
<223> OTHER INFORMATION: target_10X_oligo_080

<400> SEQUENCE: 221
gaatcctagt acaagtggcc ggtctccgtc gttagcaacg ttatagacgc agtgttttgc      60
cagaaacggc cctccgtacc agcggaaaga atcggcagag atccgctgga ccccagccag    120
cttcgcgaga ccgacatcca atccggacga ta                                   152
```

```
<210> SEQ ID NO 222
<211> LENGTH: 152
<212> TYPE: DNA
<213> ORGANISM: Artificial Sequence
<220> FEATURE:
<223> OTHER INFORMATION: target_10X_oligo_081

<400> SEQUENCE: 222
gaatcctagt acaagtggcc ggtctcaacg ttatagacgc agtgttttgc cagaaacggc     60
cctccgtacc agcggaaaga atcggcagag atccgctgga ccccagccag cttcgcgcta    120
gcagaggaga ccgacatcca atccggacga ta                                   152

<210> SEQ ID NO 223
<211> LENGTH: 152
<212> TYPE: DNA
<213> ORGANISM: Artificial Sequence
<220> FEATURE:
<223> OTHER INFORMATION: target_10X_oligo_082

<400> SEQUENCE: 223
gaatcctagt acaagtggcc ggtctcacgc agtgttttgc cagaaacggc cctccgtacc     60
agcggaaaga atcggcagag atccgctgga ccccagccag cttcgcgcta gcagagcctg    120
tctggagaga ccgacatcca atccggacga ta                                   152

<210> SEQ ID NO 224
<211> LENGTH: 152
<212> TYPE: DNA
<213> ORGANISM: Artificial Sequence
<220> FEATURE:
<223> OTHER INFORMATION: target_10X_oligo_083

<400> SEQUENCE: 224
gaatcctagt acaagtggcc ggtctcttgc cagaaacggc cctccgtacc agcggaaaga     60
atcggcagag atccgctgga ccccagccag cttcgcgcta gcagagcctg tctggagttt    120
caagaggaga ccgacatcca atccggacga ta                                   152

<210> SEQ ID NO 225
<211> LENGTH: 152
<212> TYPE: DNA
<213> ORGANISM: Artificial Sequence
<220> FEATURE:
<223> OTHER INFORMATION: target_10X_oligo_084

<400> SEQUENCE: 225
gaatcctagt acaagtggcc ggtctccggc cctccgtacc agcggaaaga atcggcagag     60
atccgctgga ccccagccag cttcgcgcta gcagagcctg tctggagttt caagagtatc    120
ggattggaga ccgacatcca atccggacga ta                                   152

<210> SEQ ID NO 226
<211> LENGTH: 152
<212> TYPE: DNA
<213> ORGANISM: Artificial Sequence
<220> FEATURE:
<223> OTHER INFORMATION: target_10X_oligo_085

<400> SEQUENCE: 226
gaatcctagt acaagtggcc ggtctctacc agcggaaaga atcggcagag atccgctgga     60
ccccagccag cttcgcgcta gcagagcctg tctggagttt caagagtatc ggattgtggc    120
agccgtgaga ccgacatcca atccggacga ta                                   152
```

<210> SEQ ID NO 227
<211> LENGTH: 152
<212> TYPE: DNA
<213> ORGANISM: Artificial Sequence
<220> FEATURE:
<223> OTHER INFORMATION: target_10X_oligo_086

<400> SEQUENCE: 227

```
gaatcctagt acaagtggcc ggtctcaaga atcggcagag atccgctgga ccccagccag    60
cttcgcgcta gcagagcctg tctggagttt caagagtatc ggattgtggc agccgtcgcg   120
aatctggaga ccgacatcca atccggacga ta                                 152
```

<210> SEQ ID NO 228
<211> LENGTH: 152
<212> TYPE: DNA
<213> ORGANISM: Artificial Sequence
<220> FEATURE:
<223> OTHER INFORMATION: target_10X_oligo_087

<400> SEQUENCE: 228

```
gaatcctagt acaagtggcc ggtctcagag atccgctgga ccccagccag cttcgcgcta    60
gcagagcctg tctggagttt caagagtatc ggattgtggc agccgtcgcg aatctgagaa   120
ttagaggaga ccgacatcca atccggacga ta                                 152
```

<210> SEQ ID NO 229
<211> LENGTH: 152
<212> TYPE: DNA
<213> ORGANISM: Artificial Sequence
<220> FEATURE:
<223> OTHER INFORMATION: target_10X_oligo_088

<400> SEQUENCE: 229

```
gaatcctagt acaagtggcc ggtctctgga ccccagccag cttcgcgcta gcagagcctg    60
tctggagttt caagagtatc ggattgtggc agccgtcgcg aatctgagaa ttagagatgg   120
cagcgggaga ccgacatcca atccggacga ta                                 152
```

<210> SEQ ID NO 230
<211> LENGTH: 152
<212> TYPE: DNA
<213> ORGANISM: Artificial Sequence
<220> FEATURE:
<223> OTHER INFORMATION: target_10X_oligo_089

<400> SEQUENCE: 230

```
gaatcctagt acaagtggcc ggtctcccag cttcgcgcta gcagagcctg tctggagttt    60
caagagtatc ggattgtggc agccgtcgcg aatctgagaa ttagagatgg cagcggtagt   120
cggccagaga ccgacatcca atccggacga ta                                 152
```

<210> SEQ ID NO 231
<211> LENGTH: 152
<212> TYPE: DNA
<213> ORGANISM: Artificial Sequence
<220> FEATURE:
<223> OTHER INFORMATION: target_10X_oligo_090

<400> SEQUENCE: 231

```
gaatcctagt acaagtggcc ggtctcgcta gcagagcctg tctggagttt caagagtatc    60
ggattgtggc agccgtcgcg aatctgagaa ttagagatgg cagcggtagt cggccactgt   120
ctttgggaga ccgacatcca atccggacga ta                                 152
```

```
<210> SEQ ID NO 232
<211> LENGTH: 152
<212> TYPE: DNA
<213> ORGANISM: Artificial Sequence
<220> FEATURE:
<223> OTHER INFORMATION: target_10X_oligo_091

<400> SEQUENCE: 232
gaatcctagt acaagtggcc ggtctccctg tctggagttt caagagtatc ggattgtggc    60
agccgtcgcg aatctgagaa ttagagatgg cagcggtagt cggccactgt ctttggagga   120
gcggaagaga ccgacatcca atccggacga ta                                 152

<210> SEQ ID NO 233
<211> LENGTH: 152
<212> TYPE: DNA
<213> ORGANISM: Artificial Sequence
<220> FEATURE:
<223> OTHER INFORMATION: target_10X_oligo_092

<400> SEQUENCE: 233
gaatcctagt acaagtggcc ggtctcgttt caagagtatc ggattgtggc agccgtcgcg    60
aatctgagaa ttagagatgg cagcggtagt cggccactgt ctttggagga gcggaatgcc   120
gttatagaga ccgacatcca atccggacga ta                                 152

<210> SEQ ID NO 234
<211> LENGTH: 152
<212> TYPE: DNA
<213> ORGANISM: Artificial Sequence
<220> FEATURE:
<223> OTHER INFORMATION: target_10X_oligo_093

<400> SEQUENCE: 234
gaatcctagt acaagtggcc ggtctctatc ggattgtggc agccgtcgcg aatctgagaa    60
ttagagatgg cagcggtagt cggccactgt ctttggagga gcggaatgcc gttatagagg   120
ctctgcgaga ccgacatcca atccggacga ta                                 152

<210> SEQ ID NO 235
<211> LENGTH: 152
<212> TYPE: DNA
<213> ORGANISM: Artificial Sequence
<220> FEATURE:
<223> OTHER INFORMATION: target_10X_oligo_094

<400> SEQUENCE: 235
gaatcctagt acaagtggcc ggtctctggc agccgtcgcg aatctgagaa ttagagatgg    60
cagcggtagt cggccactgt ctttggagga gcggaatgcc gttatagagg ctctgcttgc   120
gcagacgaga ccgacatcca atccggacga ta                                 152

<210> SEQ ID NO 236
<211> LENGTH: 152
<212> TYPE: DNA
<213> ORGANISM: Artificial Sequence
<220> FEATURE:
<223> OTHER INFORMATION: target_10X_oligo_095

<400> SEQUENCE: 236
gaatcctagt acaagtggcc ggtctccgcg aatctgagaa ttagagatgg cagcggtagt    60
cggccactgt ctttggagga gcggaatgcc gttatagagg ctctgcttgc gcagaccgaa   120
```
aggtctgaga ccgacatcca atccggacga ta                                        152

<210> SEQ ID NO 237
<211> LENGTH: 152
<212> TYPE: DNA
<213> ORGANISM: Artificial Sequence
<220> FEATURE:
<223> OTHER INFORMATION: target_10X_oligo_096

<400> SEQUENCE: 237
gaatcctagt acaagtggcc ggtctcagaa ttagagatgg cagcggtagt cggccactgt          60
ctttggagga gcggaatgcc gttatagagg ctctgcttgc gcagaccgaa aggtctttga         120
cgtggagaga ccgacatcca atccggacga ta                                        152

<210> SEQ ID NO 238
<211> LENGTH: 152
<212> TYPE: DNA
<213> ORGANISM: Artificial Sequence
<220> FEATURE:
<223> OTHER INFORMATION: target_10X_oligo_097

<400> SEQUENCE: 238
gaatcctagt acaagtggcc ggtctcatgg cagcggtagt cggccactgt ctttggagga          60
gcggaatgcc gttatagagg ctctgcttgc gcagaccgaa aggtctttga cgtggagcga         120
cattgcgaga ccgacatcca atccggacga ta                                        152

<210> SEQ ID NO 239
<211> LENGTH: 152
<212> TYPE: DNA
<213> ORGANISM: Artificial Sequence
<220> FEATURE:
<223> OTHER INFORMATION: target_10X_oligo_098

<400> SEQUENCE: 239
gaatcctagt acaagtggcc ggtctctagt cggccactgt ctttggagga gcggaatgcc          60
gttatagagg ctctgcttgc gcagaccgaa aggtctttga cgtggagcga cattgcgctg         120
gaaattgaga ccgacatcca atccggacga ta                                        152

<210> SEQ ID NO 240
<211> LENGTH: 152
<212> TYPE: DNA
<213> ORGANISM: Artificial Sequence
<220> FEATURE:
<223> OTHER INFORMATION: target_10X_oligo_099

<400> SEQUENCE: 240
gaatcctagt acaagtggcc ggtctcctgt ctttggagga gcggaatgcc gttatagagg          60
ctctgcttgc gcagaccgaa aggtctttga cgtggagcga cattgcgctg gaaattctga         120
aactgcgaga ccgacatcca atccggacga ta                                        152

<210> SEQ ID NO 241
<211> LENGTH: 152
<212> TYPE: DNA
<213> ORGANISM: Artificial Sequence
<220> FEATURE:
<223> OTHER INFORMATION: target_10X_oligo_100

<400> SEQUENCE: 241
gaatcctagt acaagtggcc ggtctcagga gcggaatgcc gttatagagg ctctgcttgc          60
gcagaccgaa aggtctttga cgtggagcga cattgcgctg gaaattctga aactgcctaa         120
cgaatcgaga ccgacatcca atccggacga ta                                         152

<210> SEQ ID NO 242
<211> LENGTH: 152
<212> TYPE: DNA
<213> ORGANISM: Artificial Sequence
<220> FEATURE:
<223> OTHER INFORMATION: target_10X_oligo_101

<400> SEQUENCE: 242
gaatcctagt acaagtggcc ggtctctgcc gttatagagg ctctgcttgc gcagaccgaa           60
aggtctttga cgtggagcga cattgcgctg gaaattctga aactgcctaa cgaatccgac          120
ctgaccgaga ccgacatcca atccggacga ta                                        152

<210> SEQ ID NO 243
<211> LENGTH: 152
<212> TYPE: DNA
<213> ORGANISM: Artificial Sequence
<220> FEATURE:
<223> OTHER INFORMATION: target_10X_oligo_102

<400> SEQUENCE: 243
gaatcctagt acaagtggcc ggtctcgagg ctctgcttgc gcagaccgaa aggtctttga           60
cgtggagcga cattgcgctg gaaattctga aactgcctaa cgaatccgac ctgacctctg          120
tcccgggaga ccgacatcca atccggacga ta                                        152

<210> SEQ ID NO 244
<211> LENGTH: 152
<212> TYPE: DNA
<213> ORGANISM: Artificial Sequence
<220> FEATURE:
<223> OTHER INFORMATION: target_10X_oligo_103

<400> SEQUENCE: 244
gaatcctagt acaagtggcc ggtctcttgc gcagaccgaa aggtctttga cgtggagcga           60
cattgcgctg gaaattctga aactgcctaa cgaatccgac ctgacctctg tcccggagga          120
agacgggaga ccgacatcca atccggacga ta                                        152

<210> SEQ ID NO 245
<211> LENGTH: 152
<212> TYPE: DNA
<213> ORGANISM: Artificial Sequence
<220> FEATURE:
<223> OTHER INFORMATION: target_10X_oligo_104

<400> SEQUENCE: 245
gaatcctagt acaagtggcc ggtctccgaa aggtctttga cgtggagcga cattgcgctg           60
gaaattctga aactgcctaa cgaatccgac ctgacctctg tcccggagga agacgggcct          120
agctccgaga ccgacatcca atccggacga ta                                        152

<210> SEQ ID NO 246
<211> LENGTH: 152
<212> TYPE: DNA
<213> ORGANISM: Artificial Sequence
<220> FEATURE:
<223> OTHER INFORMATION: target_10X_oligo_105

<400> SEQUENCE: 246
gaatcctagt acaagtggcc ggtctcttga cgtggagcga cattgcgctg gaaattctga           60

```
aactgcctaa cgaatccgac ctgacctctg tcccggagga agacgggcct agctccctgg    120
cctactgaga ccgacatcca atccggacga ta                                 152
```

<210> SEQ ID NO 247
<211> LENGTH: 152
<212> TYPE: DNA
<213> ORGANISM: Artificial Sequence
<220> FEATURE:
<223> OTHER INFORMATION: target_10X_oligo_106

<400> SEQUENCE: 247

```
gaatcctagt acaagtggcc ggtctcgcga cattgcgctg gaaattctga aactgcctaa    60
cgaatccgac ctgacctctg tcccggagga agacgggcct agctccctgg cctactctca    120
atttgcgaga ccgacatcca atccggacga ta                                 152
```

<210> SEQ ID NO 248
<211> LENGTH: 152
<212> TYPE: DNA
<213> ORGANISM: Artificial Sequence
<220> FEATURE:
<223> OTHER INFORMATION: target_10X_oligo_107

<400> SEQUENCE: 248

```
gaatcctagt acaagtggcc ggtctcgctg gaaattctga aactgcctaa cgaatccgac    60
ctgacctctg tcccggagga agacgggcct agctccctgg cctactctca atttgctccg    120
ttcgatgaga ccgacatcca atccggacga ta                                 152
```

<210> SEQ ID NO 249
<211> LENGTH: 152
<212> TYPE: DNA
<213> ORGANISM: Artificial Sequence
<220> FEATURE:
<223> OTHER INFORMATION: target_10X_oligo_108

<400> SEQUENCE: 249

```
gaatcctagt acaagtggcc ggtctcctga aactgcctaa cgaatccgac ctgacctctg    60
tcccggagga agacgggcct agctccctgg cctactctca atttgctccg ttcgatgaga    120
cttcaggaga ccgacatcca atccggacga ta                                 152
```

<210> SEQ ID NO 250
<211> LENGTH: 152
<212> TYPE: DNA
<213> ORGANISM: Artificial Sequence
<220> FEATURE:
<223> OTHER INFORMATION: target_10X_oligo_109

<400> SEQUENCE: 250

```
gaatcctagt acaagtggcc ggtctcctaa cgaatccgac ctgacctctg tcccggagga    60
agacgggcct agctccctgg cctactctca atttgctccg ttcgatgaga cttcagcccg    120
aatcgcgaga ccgacatcca atccggacga ta                                 152
```

<210> SEQ ID NO 251
<211> LENGTH: 152
<212> TYPE: DNA
<213> ORGANISM: Artificial Sequence
<220> FEATURE:
<223> OTHER INFORMATION: target_10X_oligo_110

<400> SEQUENCE: 251

```
gaatcctagt acaagtggcc ggtctccgac ctgacctctg tcccggagga agacgggcct    60
```
agctccctgg cctactctca atttgctccg ttcgatgaga cttcagcccg aatcgcggaa    120
ttcattgaga ccgacatcca atccggacga ta                                  152

<210> SEQ ID NO 252
<211> LENGTH: 152
<212> TYPE: DNA
<213> ORGANISM: Artificial Sequence
<220> FEATURE:
<223> OTHER INFORMATION: target_10X_oligo_111

<400> SEQUENCE: 252
gaatcctagt acaagtggcc ggtctctctg tcccggagga agacgggcct agctccctgg    60
cctactctca atttgctccg ttcgatgaga cttcagcccg aatcgcggaa ttcattgcaa    120
aaaaccgaga ccgacatcca atccggacga ta                                  152

<210> SEQ ID NO 253
<211> LENGTH: 152
<212> TYPE: DNA
<213> ORGANISM: Artificial Sequence
<220> FEATURE:
<223> OTHER INFORMATION: target_10X_oligo_112

<400> SEQUENCE: 253
gaatcctagt acaagtggcc ggtctcagga agacgggcct agctccctgg cctactctca    60
atttgctccg ttcgatgaga cttcagcccg aatcgcggaa ttcattgcaa aaaaccggcg    120
caagatgaga ccgacatcca atccggacga ta                                  152

<210> SEQ ID NO 254
<211> LENGTH: 152
<212> TYPE: DNA
<213> ORGANISM: Artificial Sequence
<220> FEATURE:
<223> OTHER INFORMATION: target_10X_oligo_113

<400> SEQUENCE: 254
gaatcctagt acaagtggcc ggtctcgcct agctccctgg cctactctca atttgctccg    60
ttcgatgaga cttcagcccg aatcgcggaa ttcattgcaa aaaaccggcg caagatcccc    120
acctttgaga ccgacatcca atccggacga ta                                  152

<210> SEQ ID NO 255
<211> LENGTH: 152
<212> TYPE: DNA
<213> ORGANISM: Artificial Sequence
<220> FEATURE:
<223> OTHER INFORMATION: target_10X_oligo_114

<400> SEQUENCE: 255
gaatcctagt acaagtggcc ggtctcctgg cctactctca atttgctccg ttcgatgaga    60
cttcagcccg aatcgcggaa ttcattgcaa aaaaccggcg caagatcccc acctttgctc    120
agtggtgaga ccgacatcca atccggacga ta                                  152

<210> SEQ ID NO 256
<211> LENGTH: 152
<212> TYPE: DNA
<213> ORGANISM: Artificial Sequence
<220> FEATURE:
<223> OTHER INFORMATION: target_10X_oligo_115

<400> SEQUENCE: 256

```
gaatcctagt acaagtggcc ggtctcctca atttgctccg ttcgatgaga cttcagcccg    60
aatcgcggaa ttcattgcaa aaaaccggcg caagatcccc acctttgctc agtggtggca   120
agagcagaga ccgacatcca atccggacga ta                                 152
```

<210> SEQ ID NO 257
<211> LENGTH: 152
<212> TYPE: DNA
<213> ORGANISM: Artificial Sequence
<220> FEATURE:
<223> OTHER INFORMATION: target_10X_oligo_116

<400> SEQUENCE: 257

```
gaatcctagt acaagtggcc ggtctctccg ttcgatgaga cttcagcccg aatcgcggaa    60
ttcattgcaa aaaccggcg caagatcccc acctttgctc agtggtggca agagcaagat   120
cggacagaga ccgacatcca atccggacga ta                                 152
```

<210> SEQ ID NO 258
<211> LENGTH: 152
<212> TYPE: DNA
<213> ORGANISM: Artificial Sequence
<220> FEATURE:
<223> OTHER INFORMATION: target_10X_oligo_117

<400> SEQUENCE: 258

```
gaatcctagt acaagtggcc ggtctcgaga cttcagcccg aatcgcggaa ttcattgcaa    60
aaaaccggcg caagatcccc acctttgctc agtggtggca agagcaagat cggacaagcc   120
gcagtggaga ccgacatcca atccggacga ta                                 152
```

<210> SEQ ID NO 259
<211> LENGTH: 152
<212> TYPE: DNA
<213> ORGANISM: Artificial Sequence
<220> FEATURE:
<223> OTHER INFORMATION: target_10X_oligo_118

<400> SEQUENCE: 259

```
gaatcctagt acaagtggcc ggtctccccg aatcgcggaa ttcattgcaa aaaaccggcg    60
caagatcccc acctttgctc agtggtggca agagcaagat cggacaagcc gcagtgacct   120
ggtggcgaga ccgacatcca atccggacga ta                                 152
```

<210> SEQ ID NO 260
<211> LENGTH: 152
<212> TYPE: DNA
<213> ORGANISM: Artificial Sequence
<220> FEATURE:
<223> OTHER INFORMATION: target_10X_oligo_119

<400> SEQUENCE: 260

```
gaatcctagt acaagtggcc ggtctcggaa ttcattgcaa aaaaccggcg caagatcccc    60
acctttgctc agtggtggca agagcaagat cggacaagcc gcagtgacct ggtggctgct   120
ctggcagaga ccgacatcca atccggacga ta                                 152
```

<210> SEQ ID NO 261
<211> LENGTH: 152
<212> TYPE: DNA
<213> ORGANISM: Artificial Sequence
<220> FEATURE:
<223> OTHER INFORMATION: target_10X_oligo_120

<400> SEQUENCE: 261

```
gaatcctagt acaagtggcc ggtctcgcaa aaaaccggcg caagatcccc acctttgctc    60
agtggtggca agagcaagat cggacaagcc gcagtgacct ggtggctgct ctggcagata   120
actcaagaga ccgacatcca atccggacga ta                                 152
```

<210> SEQ ID NO 262
<211> LENGTH: 152
<212> TYPE: DNA
<213> ORGANISM: Artificial Sequence
<220> FEATURE:
<223> OTHER INFORMATION: target_10X_oligo_121

<400> SEQUENCE: 262

```
gaatcctagt acaagtggcc ggtctcggcg caagatcccc acctttgctc agtggtggca    60
agagcaagat cggacaagcc gcagtgacct ggtggctgct ctggcagata actcaatcgc   120
tggcgagaga ccgacatcca atccggacga ta                                 152
```

<210> SEQ ID NO 263
<211> LENGTH: 152
<212> TYPE: DNA
<213> ORGANISM: Artificial Sequence
<220> FEATURE:
<223> OTHER INFORMATION: target_10X_oligo_122

<400> SEQUENCE: 263

```
gaatcctagt acaagtggcc ggtctccccc acctttgctc agtggtggca agagcaagat    60
cggacaagcc gcagtgacct ggtggctgct ctggcagata actcaatcgc tggcgaggaa   120
gaacaggaga ccgacatcca atccggacga ta                                 152
```

<210> SEQ ID NO 264
<211> LENGTH: 152
<212> TYPE: DNA
<213> ORGANISM: Artificial Sequence
<220> FEATURE:
<223> OTHER INFORMATION: target_10X_oligo_123

<400> SEQUENCE: 264

```
gaatcctagt acaagtggcc ggtctcgctc agtggtggca agagcaagat cggacaagcc    60
gcagtgacct ggtggctgct ctggcagata actcaatcgc tggcgaggaa gaacaggagc   120
tgcttggaga ccgacatcca atccggacga ta                                 152
```

<210> SEQ ID NO 265
<211> LENGTH: 152
<212> TYPE: DNA
<213> ORGANISM: Artificial Sequence
<220> FEATURE:
<223> OTHER INFORMATION: target_10X_oligo_124

<400> SEQUENCE: 265

```
gaatcctagt acaagtggcc ggtctcggca agagcaagat cggacaagcc gcagtgacct    60
ggtggctgct ctggcagata actcaatcgc tggcgaggaa gaacaggagc tgcttgtcca   120
cctgccgaga ccgacatcca atccggacga ta                                 152
```

<210> SEQ ID NO 266
<211> LENGTH: 152
<212> TYPE: DNA
<213> ORGANISM: Artificial Sequence
<220> FEATURE:
<223> OTHER INFORMATION: target_10X_oligo_125

```
<400> SEQUENCE: 266
gaatcctagt acaagtggcc ggtctcagat cggacaagcc gcagtgacct ggtggctgct      60
ctggcagata actcaatcgc tggcgaggaa gaacaggagc tgcttgtcca cctgccggac     120
gctgaggaga ccgacatcca atccggacga ta                                   152

<210> SEQ ID NO 267
<211> LENGTH: 152
<212> TYPE: DNA
<213> ORGANISM: Artificial Sequence
<220> FEATURE:
<223> OTHER INFORMATION: target_10X_oligo_126

<400> SEQUENCE: 267
gaatcctagt acaagtggcc ggtctcagcc gcagtgacct ggtggctgct ctggcagata      60
actcaatcgc tggcgaggaa gaacaggagc tgcttgtcca cctgccggac gctgagctcg     120
aggcccgaga ccgacatcca atccggacga ta                                   152

<210> SEQ ID NO 268
<211> LENGTH: 152
<212> TYPE: DNA
<213> ORGANISM: Artificial Sequence
<220> FEATURE:
<223> OTHER INFORMATION: target_10X_oligo_127

<400> SEQUENCE: 268
gaatcctagt acaagtggcc ggtctcacct ggtggctgct ctggcagata actcaatcgc      60
tggcgaggaa gaacaggagc tgcttgtcca cctgccggac gctgagctcg aggcccttga     120
agggctgaga ccgacatcca atccggacga ta                                   152

<210> SEQ ID NO 269
<211> LENGTH: 152
<212> TYPE: DNA
<213> ORGANISM: Artificial Sequence
<220> FEATURE:
<223> OTHER INFORMATION: target_10X_oligo_128

<400> SEQUENCE: 269
gaatcctagt acaagtggcc ggtctctgct ctggcagata actcaatcgc tggcgaggaa      60
gaacaggagc tgcttgtcca cctgccggac gctgagctcg aggcccttga agggctcgcc     120
ttgcctgaga ccgacatcca atccggacga ta                                   152

<210> SEQ ID NO 270
<211> LENGTH: 152
<212> TYPE: DNA
<213> ORGANISM: Artificial Sequence
<220> FEATURE:
<223> OTHER INFORMATION: target_10X_oligo_129

<400> SEQUENCE: 270
gaatcctagt acaagtggcc ggtctcgata actcaatcgc tggcgaggaa gaacaggagc      60
tgcttgtcca cctgccggac gctgagctcg aggcccttga agggctcgcc ttgcctagcg     120
gccggggaga ccgacatcca atccggacga ta                                   152

<210> SEQ ID NO 271
<211> LENGTH: 152
<212> TYPE: DNA
<213> ORGANISM: Artificial Sequence
<220> FEATURE:
<223> OTHER INFORMATION: target_10X_oligo_130
```

```
<400> SEQUENCE: 271
gaatcctagt acaagtggcc ggtctctcgc tggcgaggaa gaacaggagc tgcttgtcca      60
cctgccggac gctgagctcg aggcccttga agggctcgcc ttgcctagcg gccgggtggc     120
ctactcgaga ccgacatcca atccggacga ta                                   152

<210> SEQ ID NO 272
<211> LENGTH: 152
<212> TYPE: DNA
<213> ORGANISM: Artificial Sequence
<220> FEATURE:
<223> OTHER INFORMATION: target_10X_oligo_131

<400> SEQUENCE: 272
gaatcctagt acaagtggcc ggtctcggaa gaacaggagc tgcttgtcca cctgccggac      60
gctgagctcg aggcccttga agggctcgcc ttgcctagcg gccgggtggc ctactcccgc     120
ctgacggaga ccgacatcca atccggacga ta                                   152

<210> SEQ ID NO 273
<211> LENGTH: 152
<212> TYPE: DNA
<213> ORGANISM: Artificial Sequence
<220> FEATURE:
<223> OTHER INFORMATION: target_10X_oligo_132

<400> SEQUENCE: 273
gaatcctagt acaagtggcc ggtctcgagc tgcttgtcca cctgccggac gctgagctcg      60
aggcccttga agggctcgcc ttgcctagcg gccgggtggc ctactcccgc ctgacgctgt     120
ccggacgaga ccgacatcca atccggacga ta                                   152

<210> SEQ ID NO 274
<211> LENGTH: 152
<212> TYPE: DNA
<213> ORGANISM: Artificial Sequence
<220> FEATURE:
<223> OTHER INFORMATION: target_10X_oligo_133

<400> SEQUENCE: 274
gaatcctagt acaagtggcc ggtctctcca cctgccggac gctgagctcg aggcccttga      60
agggctcgcc ttgcctagcg gccgggtggc ctactcccgc ctgacgctgt ccggacttac     120
cagggtgaga ccgacatcca atccggacga ta                                   152

<210> SEQ ID NO 275
<211> LENGTH: 152
<212> TYPE: DNA
<213> ORGANISM: Artificial Sequence
<220> FEATURE:
<223> OTHER INFORMATION: target_10X_oligo_134

<400> SEQUENCE: 275
gaatcctagt acaagtggcc ggtctcggac gctgagctcg aggcccttga agggctcgcc      60
ttgcctagcg gccgggtggc ctactcccgc ctgacgctgt ccggacttac cagggtgatg     120
agagacgaga ccgacatcca atccggacga ta                                   152

<210> SEQ ID NO 276
<211> LENGTH: 152
<212> TYPE: DNA
<213> ORGANISM: Artificial Sequence
<220> FEATURE:
```

<223> OTHER INFORMATION: target_10X_oligo_135

<400> SEQUENCE: 276
gaatcctagt acaagtggcc ggtctcctcg aggcccttga agggctcgcc ttgcctagcg        60
gccgggtggc ctactcccgc ctgacgctgt ccggacttac cagggtgatg agagacgatg       120
gagtgggaga ccgacatcca atccggacga ta                                    152

<210> SEQ ID NO 277
<211> LENGTH: 152
<212> TYPE: DNA
<213> ORGANISM: Artificial Sequence
<220> FEATURE:
<223> OTHER INFORMATION: target_10X_oligo_136

<400> SEQUENCE: 277
gaatcctagt acaagtggcc ggtctcttga agggctcgcc ttgcctagcg gccgggtggc        60
ctactcccgc ctgacgctgt ccggacttac cagggtgatg agagacgatg gagtggacgt       120
tcacaagaga ccgacatcca atccggacga ta                                    152

<210> SEQ ID NO 278
<211> LENGTH: 152
<212> TYPE: DNA
<213> ORGANISM: Artificial Sequence
<220> FEATURE:
<223> OTHER INFORMATION: target_10X_oligo_137

<400> SEQUENCE: 278
gaatcctagt acaagtggcc ggtctccgcc ttgcctagcg gccgggtggc ctactcccgc        60
ctgacgctgt ccggacttac cagggtgatg agagacgatg gagtggacgt tcacaacgct       120
cgcaaggaga ccgacatcca atccggacga ta                                    152

<210> SEQ ID NO 279
<211> LENGTH: 152
<212> TYPE: DNA
<213> ORGANISM: Artificial Sequence
<220> FEATURE:
<223> OTHER INFORMATION: target_10X_oligo_138

<400> SEQUENCE: 279
gaatcctagt acaagtggcc ggtctcagcg gccgggtggc ctactcccgc ctgacgctgt        60
ccggacttac cagggtgatg agagacgatg gagtggacgt tcacaacgct cgcaagactt       120
gctttggaga ccgacatcca atccggacga ta                                    152

<210> SEQ ID NO 280
<211> LENGTH: 152
<212> TYPE: DNA
<213> ORGANISM: Artificial Sequence
<220> FEATURE:
<223> OTHER INFORMATION: target_10X_oligo_139

<400> SEQUENCE: 280
gaatcctagt acaagtggcc ggtctctggc ctactcccgc ctgacgctgt ccggacttac        60
cagggtgatg agagacgatg gagtggacgt tcacaacgct cgcaagactt gctttggagt       120
tgacgagaga ccgacatcca atccggacga ta                                    152

<210> SEQ ID NO 281
<211> LENGTH: 152
<212> TYPE: DNA
<213> ORGANISM: Artificial Sequence

```
<220> FEATURE:
<223> OTHER INFORMATION: target_10X_oligo_140

<400> SEQUENCE: 281
gaatcctagt acaagtggcc ggtctcccgc ctgacgctgt ccggacttac cagggtgatg      60
agagacgatg gagtggacgt tcacaacgct cgcaagactt gctttggagt tgacgacaac     120
tggcgcgaga ccgacatcca atccggacga ta                                   152

<210> SEQ ID NO 282
<211> LENGTH: 152
<212> TYPE: DNA
<213> ORGANISM: Artificial Sequence
<220> FEATURE:
<223> OTHER INFORMATION: target_10X_oligo_141

<400> SEQUENCE: 282
gaatcctagt acaagtggcc ggtctcctgt ccggacttac cagggtgatg agagacgatg      60
gagtggacgt tcacaacgct cgcaagactt gctttggagt tgacgacaac tggcgccccc     120
cgctgcgaga ccgacatcca atccggacga ta                                   152

<210> SEQ ID NO 283
<211> LENGTH: 152
<212> TYPE: DNA
<213> ORGANISM: Artificial Sequence
<220> FEATURE:
<223> OTHER INFORMATION: target_10X_oligo_142

<400> SEQUENCE: 283
gaatcctagt acaagtggcc ggtctcttac cagggtgatg agagacgatg gagtggacgt      60
tcacaacgct cgcaagactt gctttggagt tgacgacaac tggcgccccc cgctgcctgc     120
cctgcagaga ccgacatcca atccggacga ta                                   152

<210> SEQ ID NO 284
<211> LENGTH: 152
<212> TYPE: DNA
<213> ORGANISM: Artificial Sequence
<220> FEATURE:
<223> OTHER INFORMATION: target_10X_oligo_143

<400> SEQUENCE: 284
gaatcctagt acaagtggcc ggtctcgatg agagacgatg gagtggacgt tcacaacgct      60
cgcaagactt gctttggagt tgacgacaac tggcgccccc cgctgcctgc cctgcacgaa     120
gctaccgaga ccgacatcca atccggacga ta                                   152

<210> SEQ ID NO 285
<211> LENGTH: 152
<212> TYPE: DNA
<213> ORGANISM: Artificial Sequence
<220> FEATURE:
<223> OTHER INFORMATION: target_10X_oligo_144

<400> SEQUENCE: 285
gaatcctagt acaagtggcc ggtctcgatg gagtggacgt tcacaacgct cgcaagactt      60
gctttggagt tgacgacaac tggcgccccc cgctgcctgc cctgcacgaa gctaccggac     120
atcccggaga ccgacatcca atccggacga ta                                   152

<210> SEQ ID NO 286
<211> LENGTH: 152
<212> TYPE: DNA
```

<213> ORGANISM: Artificial Sequence
<220> FEATURE:
<223> OTHER INFORMATION: target_10X_oligo_145

<400> SEQUENCE: 286

| | |
|---|---|
| gaatcctagt acaagtggcc ggtctcacgt tcacaacgct cgcaagactt gctttggagt | 60 |
| tgacgacaac tggcgccccc cgctgcctgc cctgcacgaa gctaccggac atcccgtggt | 120 |
| cgatcggaga ccgacatcca atccggacga ta | 152 |

<210> SEQ ID NO 287
<211> LENGTH: 152
<212> TYPE: DNA
<213> ORGANISM: Artificial Sequence
<220> FEATURE:
<223> OTHER INFORMATION: target_10X_oligo_146

<400> SEQUENCE: 287

| | |
|---|---|
| gaatcctagt acaagtggcc ggtctccgct cgcaagactt gctttggagt tgacgacaac | 60 |
| tggcgccccc cgctgcctgc cctgcacgaa gctaccggac atcccgtggt cgatcggaat | 120 |
| ttggcggaga ccgacatcca atccggacga ta | 152 |

<210> SEQ ID NO 288
<211> LENGTH: 152
<212> TYPE: DNA
<213> ORGANISM: Artificial Sequence
<220> FEATURE:
<223> OTHER INFORMATION: target_10X_oligo_147

<400> SEQUENCE: 288

| | |
|---|---|
| gaatcctagt acaagtggcc ggtctcactt gctttggagt tgacgacaac tggcgccccc | 60 |
| cgctgcctgc cctgcacgaa gctaccggac atcccgtggt cgatcggaat ttggcgatcc | 120 |
| tgcggagaga ccgacatcca atccggacga ta | 152 |

<210> SEQ ID NO 289
<211> LENGTH: 152
<212> TYPE: DNA
<213> ORGANISM: Artificial Sequence
<220> FEATURE:
<223> OTHER INFORMATION: target_10X_oligo_148

<400> SEQUENCE: 289

| | |
|---|---|
| gaatcctagt acaagtggcc ggtctcgagt tgacgacaac tggcgccccc cgctgcctgc | 60 |
| cctgcacgaa gctaccggac atcccgtggt cgatcggaat ttggcgatcc tgcggaagtt | 120 |
| tctctcgaga ccgacatcca atccggacga ta | 152 |

<210> SEQ ID NO 290
<211> LENGTH: 152
<212> TYPE: DNA
<213> ORGANISM: Artificial Sequence
<220> FEATURE:
<223> OTHER INFORMATION: target_10X_oligo_149

<400> SEQUENCE: 290

| | |
|---|---|
| gaatcctagt acaagtggcc ggtctccaac tggcgccccc cgctgcctgc cctgcacgaa | 60 |
| gctaccggac atcccgtggt cgatcggaat ttggcgatcc tgcggaagtt tctctcatcc | 120 |
| gctaccgaga ccgacatcca atccggacga ta | 152 |

<210> SEQ ID NO 291
<211> LENGTH: 152

```
<212> TYPE: DNA
<213> ORGANISM: Artificial Sequence
<220> FEATURE:
<223> OTHER INFORMATION: target_10X_oligo_150

<400> SEQUENCE: 291
gaatcctagt acaagtggcc ggtctccccc cgctgcctgc cctgcacgaa gctaccggac    60
atcccgtggt cgatcggaat ttggcgatcc tgcggaagtt tctctcatcc gctaccatga   120
ggtggggaga ccgacatcca atccggacga ta                                  152

<210> SEQ ID NO 292
<211> LENGTH: 152
<212> TYPE: DNA
<213> ORGANISM: Artificial Sequence
<220> FEATURE:
<223> OTHER INFORMATION: target_10X_oligo_151

<400> SEQUENCE: 292
gaatcctagt acaagtggcc ggtctcctgc cctgcacgaa gctaccggac atcccgtggt    60
cgatcggaat ttggcgatcc tgcggaagtt tctctcatcc gctaccatga ggtggggacc   120
acctcagaga ccgacatcca atccggacga ta                                  152

<210> SEQ ID NO 293
<211> LENGTH: 152
<212> TYPE: DNA
<213> ORGANISM: Artificial Sequence
<220> FEATURE:
<223> OTHER INFORMATION: target_10X_oligo_152

<400> SEQUENCE: 293
gaatcctagt acaagtggcc ggtctccgaa gctaccggac atcccgtggt cgatcggaat    60
ttggcgatcc tgcggaagtt tctctcatcc gctaccatga ggtggggacc acctcaatct   120
atcgtggaga ccgacatcca atccggacga ta                                  152

<210> SEQ ID NO 294
<211> LENGTH: 152
<212> TYPE: DNA
<213> ORGANISM: Artificial Sequence
<220> FEATURE:
<223> OTHER INFORMATION: target_10X_oligo_153

<400> SEQUENCE: 294
gaatcctagt acaagtggcc ggtctcggac atcccgtggt cgatcggaat ttggcgatcc    60
tgcggaagtt tctctcatcc gctaccatga ggtggggacc acctcaatct atcgtggtgg   120
agctgggaga ccgacatcca atccggacga ta                                  152

<210> SEQ ID NO 295
<211> LENGTH: 152
<212> TYPE: DNA
<213> ORGANISM: Artificial Sequence
<220> FEATURE:
<223> OTHER INFORMATION: target_10X_oligo_154

<400> SEQUENCE: 295
gaatcctagt acaagtggcc ggtctctggt cgatcggaat ttggcgatcc tgcggaagtt    60
tctctcatcc gctaccatga ggtggggacc acctcaatct atcgtggtgg agctggcccg   120
gggcgcgaga ccgacatcca atccggacga ta                                  152

<210> SEQ ID NO 296
```

```
<211> LENGTH: 152
<212> TYPE: DNA
<213> ORGANISM: Artificial Sequence
<220> FEATURE:
<223> OTHER INFORMATION: target_10X_oligo_155

<400> SEQUENCE: 296
gaatcctagt acaagtggcc ggtctcgaat ttggcgatcc tgcggaagtt tctctcatcc    60
gctaccatga ggtggggacc acctcaatct atcgtggtgg agctggcccg gggcgccagc   120
gagtctgaga ccgacatcca atccggacga ta                                 152

<210> SEQ ID NO 297
<211> LENGTH: 152
<212> TYPE: DNA
<213> ORGANISM: Artificial Sequence
<220> FEATURE:
<223> OTHER INFORMATION: target_10X_oligo_156

<400> SEQUENCE: 297
gaatcctagt acaagtggcc ggtctcatcc tgcggaagtt tctctcatcc gctaccatga    60
ggtggggacc acctcaatct atcgtggtgg agctggcccg gggcgccagc gagtctcgag   120
agcgacgaga ccgacatcca atccggacga ta                                 152

<210> SEQ ID NO 298
<211> LENGTH: 152
<212> TYPE: DNA
<213> ORGANISM: Artificial Sequence
<220> FEATURE:
<223> OTHER INFORMATION: target_10X_oligo_157

<400> SEQUENCE: 298
gaatcctagt acaagtggcc ggtctcagtt tctctcatcc gctaccatga ggtggggacc    60
acctcaatct atcgtggtgg agctggcccg gggcgccagc gagtctcgag agcgacaggc   120
cgaggagaga ccgacatcca atccggacga ta                                 152

<210> SEQ ID NO 299
<211> LENGTH: 152
<212> TYPE: DNA
<213> ORGANISM: Artificial Sequence
<220> FEATURE:
<223> OTHER INFORMATION: target_10X_oligo_158

<400> SEQUENCE: 299
gaatcctagt acaagtggcc ggtctcatcc gctaccatga ggtggggacc acctcaatct    60
atcgtggtgg agctggcccg gggcgccagc gagtctcgag agcgacaggc cgaggaggaa   120
gccgccgaga ccgacatcca atccggacga ta                                 152

<210> SEQ ID NO 300
<211> LENGTH: 152
<212> TYPE: DNA
<213> ORGANISM: Artificial Sequence
<220> FEATURE:
<223> OTHER INFORMATION: target_10X_oligo_159

<400> SEQUENCE: 300
gaatcctagt acaagtggcc ggtctcatga ggtggggacc acctcaatct atcgtggtgg    60
agctggcccg gggcgccagc gagtctcgag agcgacaggc cgaggaggaa gccgccagaa   120
gagcccgaga ccgacatcca atccggacga ta                                 152
```

<210> SEQ ID NO 301
<211> LENGTH: 152
<212> TYPE: DNA
<213> ORGANISM: Artificial Sequence
<220> FEATURE:
<223> OTHER INFORMATION: target_10X_oligo_160

<400> SEQUENCE: 301

```
gaatcctagt acaagtggcc ggtctcgacc acctcaatct atcgtggtgg agctggcccg      60
gggcgccagc gagtctcgag agcgacaggc cgaggaggaa gccgccagaa gagcccatcg     120
gaaagcgaga ccgacatcca atccggacga ta                                   152
```

<210> SEQ ID NO 302
<211> LENGTH: 152
<212> TYPE: DNA
<213> ORGANISM: Artificial Sequence
<220> FEATURE:
<223> OTHER INFORMATION: target_10X_oligo_161

<400> SEQUENCE: 302

```
gaatcctagt acaagtggcc ggtctcatct atcgtggtgg agctggcccg gggcgccagc      60
gagtctcgag agcgacaggc cgaggaggaa gccgccagaa gagcccatcg gaaagccaac     120
gatcgagaga ccgacatcca atccggacga ta                                   152
```

<210> SEQ ID NO 303
<211> LENGTH: 152
<212> TYPE: DNA
<213> ORGANISM: Artificial Sequence
<220> FEATURE:
<223> OTHER INFORMATION: target_10X_oligo_162

<400> SEQUENCE: 303

```
gaatcctagt acaagtggcc ggtctcgtgg agctggcccg gggcgccagc gagtctcgag      60
agcgacaggc cgaggaggaa gccgccagaa gagcccatcg gaaagccaac gatcgaataa     120
gagccggaga ccgacatcca atccggacga ta                                   152
```

<210> SEQ ID NO 304
<211> LENGTH: 152
<212> TYPE: DNA
<213> ORGANISM: Artificial Sequence
<220> FEATURE:
<223> OTHER INFORMATION: target_10X_oligo_163

<400> SEQUENCE: 304

```
gaatcctagt acaagtggcc ggtctccccg gggcgccagc gagtctcgag agcgacaggc      60
cgaggaggaa gccgccagaa gagcccatcg gaaagccaac gatcgaataa gagccgagct     120
gcgggcgaga ccgacatcca atccggacga ta                                   152
```

<210> SEQ ID NO 305
<211> LENGTH: 152
<212> TYPE: DNA
<213> ORGANISM: Artificial Sequence
<220> FEATURE:
<223> OTHER INFORMATION: target_10X_oligo_164

<400> SEQUENCE: 305

```
gaatcctagt acaagtggcc ggtctccagc gagtctcgag agcgacaggc cgaggaggaa      60
gccgccagaa gagcccatcg gaaagccaac gatcgaataa gagccgagct gcgggcatcc     120
ggactcgaga ccgacatcca atccggacga ta                                   152
```

<210> SEQ ID NO 306
<211> LENGTH: 152
<212> TYPE: DNA
<213> ORGANISM: Artificial Sequence
<220> FEATURE:
<223> OTHER INFORMATION: target_10X_oligo_165

<400> SEQUENCE: 306
gaatcctagt acaagtggcc ggtctccgag agcgacaggc cgaggaggaa gccgccagaa      60
gagcccatcg gaaagccaac gatcgaataa gagccgagct gcgggcatcc ggactcagcg     120
atcctagaga ccgacatcca atccggacga ta                                   152

<210> SEQ ID NO 307
<211> LENGTH: 152
<212> TYPE: DNA
<213> ORGANISM: Artificial Sequence
<220> FEATURE:
<223> OTHER INFORMATION: target_10X_oligo_166

<400> SEQUENCE: 307
gaatcctagt acaagtggcc ggtctcaggc cgaggaggaa gccgccagaa gagcccatcg      60
gaaagccaac gatcgaataa gagccgagct gcgggcatcc ggactcagcg atcctagccc     120
tgctgagaga ccgacatcca atccggacga ta                                   152

<210> SEQ ID NO 308
<211> LENGTH: 152
<212> TYPE: DNA
<213> ORGANISM: Artificial Sequence
<220> FEATURE:
<223> OTHER INFORMATION: target_10X_oligo_167

<400> SEQUENCE: 308
gaatcctagt acaagtggcc ggtctcggaa gccgccagaa gagcccatcg gaaagccaac      60
gatcgaataa gagccgagct gcgggcatcc ggactcagcg atcctagccc tgctgacctt     120
gtccgcgaga ccgacatcca atccggacga ta                                   152

<210> SEQ ID NO 309
<211> LENGTH: 152
<212> TYPE: DNA
<213> ORGANISM: Artificial Sequence
<220> FEATURE:
<223> OTHER INFORMATION: target_10X_oligo_168

<400> SEQUENCE: 309
gaatcctagt acaagtggcc ggtctcagaa gagcccatcg gaaagccaac gatcgaataa      60
gagccgagct gcgggcatcc ggactcagcg atcctagccc tgctgacctt gtccgcgcaa     120
gactgcgaga ccgacatcca atccggacga ta                                   152

<210> SEQ ID NO 310
<211> LENGTH: 152
<212> TYPE: DNA
<213> ORGANISM: Artificial Sequence
<220> FEATURE:
<223> OTHER INFORMATION: target_10X_oligo_169

<400> SEQUENCE: 310
gaatcctagt acaagtggcc ggtctcatcg gaaagccaac gatcgaataa gagccgagct      60
gcgggcatcc ggactcagcg atcctagccc tgctgacctt gtccgcgcaa gactgctgga     120
actgtagaga ccgacatcca atccggacga ta                                   152

```
<210> SEQ ID NO 311
<211> LENGTH: 152
<212> TYPE: DNA
<213> ORGANISM: Artificial Sequence
<220> FEATURE:
<223> OTHER INFORMATION: target_10X_oligo_170

<400> SEQUENCE: 311
gaatcctagt acaagtggcc ggtctccaac gatcgaataa gagccgagct gcgggcatcc      60
ggactcagcg atcctagccc tgctgacctt gtccgcgcaa gactgctgga actgtatgac     120
tgccacgaga ccgacatcca atccggacga ta                                   152

<210> SEQ ID NO 312
<211> LENGTH: 152
<212> TYPE: DNA
<213> ORGANISM: Artificial Sequence
<220> FEATURE:
<223> OTHER INFORMATION: target_10X_oligo_171

<400> SEQUENCE: 312
gaatcctagt acaagtggcc ggtctcataa gagccgagct gcgggcatcc ggactcagcg      60
atcctagccc tgctgacctt gtccgcgcaa gactgctgga actgtatgac tgccactgca    120
tgtattgaga ccgacatcca atccggacga ta                                   152

<210> SEQ ID NO 313
<211> LENGTH: 152
<212> TYPE: DNA
<213> ORGANISM: Artificial Sequence
<220> FEATURE:
<223> OTHER INFORMATION: target_10X_oligo_172

<400> SEQUENCE: 313
gaatcctagt acaagtggcc ggtctcagct gcgggcatcc ggactcagcg atcctagccc      60
tgctgacctt gtccgcgcaa gactgctgga actgtatgac tgccactgca tgtattgtgg    120
ggcaccgaga ccgacatcca atccggacga ta                                   152

<210> SEQ ID NO 314
<211> LENGTH: 152
<212> TYPE: DNA
<213> ORGANISM: Artificial Sequence
<220> FEATURE:
<223> OTHER INFORMATION: target_10X_oligo_173

<400> SEQUENCE: 314
gaatcctagt acaagtggcc ggtctcatcc ggactcagcg atcctagccc tgctgacctt      60
gtccgcgcaa gactgctgga actgtatgac tgccactgca tgtattgtgg ggcacctata    120
agctgggaga ccgacatcca atccggacga ta                                   152

<210> SEQ ID NO 315
<211> LENGTH: 152
<212> TYPE: DNA
<213> ORGANISM: Artificial Sequence
<220> FEATURE:
<223> OTHER INFORMATION: target_10X_oligo_174

<400> SEQUENCE: 315
gaatcctagt acaagtggcc ggtctcagcg atcctagccc tgctgacctt gtccgcgcaa      60
gactgctgga actgtatgac tgccactgca tgtattgtgg ggcacctata agctgggaga    120
```

```
actctggaga ccgacatcca atccggacga ta                              152

<210> SEQ ID NO 316
<211> LENGTH: 152
<212> TYPE: DNA
<213> ORGANISM: Artificial Sequence
<220> FEATURE:
<223> OTHER INFORMATION: target_10X_oligo_175

<400> SEQUENCE: 316
gaatcctagt acaagtggcc ggtctcgccc tgctgacctt gtccgcgcaa gactgctgga   60
actgtatgac tgccactgca tgtattgtgg ggcacctata agctgggaga actctgaact  120
ggaccagaga ccgacatcca atccggacga ta                              152

<210> SEQ ID NO 317
<211> LENGTH: 152
<212> TYPE: DNA
<213> ORGANISM: Artificial Sequence
<220> FEATURE:
<223> OTHER INFORMATION: target_10X_oligo_176

<400> SEQUENCE: 317
gaatcctagt acaagtggcc ggtctcccctt gtccgcgcaa gactgctgga actgtatgac   60
tgccactgca tgtattgtgg ggcacctata agctgggaga actctgaact ggaccacatc  120
gtcccagaga ccgacatcca atccggacga ta                              152

<210> SEQ ID NO 318
<211> LENGTH: 152
<212> TYPE: DNA
<213> ORGANISM: Artificial Sequence
<220> FEATURE:
<223> OTHER INFORMATION: target_10X_oligo_177

<400> SEQUENCE: 318
gaatcctagt acaagtggcc ggtctcgcaa gactgctgga actgtatgac tgccactgca   60
tgtattgtgg ggcacctata agctgggaga actctgaact ggaccacatc gtcccacgga  120
ctgatggaga ccgacatcca atccggacga ta                              152

<210> SEQ ID NO 319
<211> LENGTH: 152
<212> TYPE: DNA
<213> ORGANISM: Artificial Sequence
<220> FEATURE:
<223> OTHER INFORMATION: target_10X_oligo_178

<400> SEQUENCE: 319
gaatcctagt acaagtggcc ggtctctgga actgtatgac tgccactgca tgtattgtgg   60
ggcacctata agctgggaga actctgaact ggaccacatc gtcccacgga ctgatggcgg  120
atcaaagaga ccgacatcca atccggacga ta                              152

<210> SEQ ID NO 320
<211> LENGTH: 152
<212> TYPE: DNA
<213> ORGANISM: Artificial Sequence
<220> FEATURE:
<223> OTHER INFORMATION: target_10X_oligo_179

<400> SEQUENCE: 320
gaatcctagt acaagtggcc ggtctctgac tgccactgca tgtattgtgg ggcacctata   60
agctgggaga actctgaact ggaccacatc gtcccacgga ctgatggcgg atcaaatcgc  120
```

```
cacgaggaga ccgacatcca atccggacga ta                                  152

<210> SEQ ID NO 321
<211> LENGTH: 152
<212> TYPE: DNA
<213> ORGANISM: Artificial Sequence
<220> FEATURE:
<223> OTHER INFORMATION: target_10X_oligo_180

<400> SEQUENCE: 321
gaatcctagt acaagtggcc ggtctctgca tgtattgtgg ggcacctata agctgggaga    60
actctgaact ggaccacatc gtcccacgga ctgatggcgg atcaaatcgc cacgagaatc   120
tggccagaga ccgacatcca atccggacga ta                                 152

<210> SEQ ID NO 322
<211> LENGTH: 152
<212> TYPE: DNA
<213> ORGANISM: Artificial Sequence
<220> FEATURE:
<223> OTHER INFORMATION: target_10X_oligo_181

<400> SEQUENCE: 322
gaatcctagt acaagtggcc ggtctcgtgg ggcacctata agctgggaga actctgaact    60
ggaccacatc gtcccacgga ctgatggcgg atcaaatcgc cacgagaatc tggccattac   120
ttgcgggaga ccgacatcca atccggacga ta                                 152

<210> SEQ ID NO 323
<211> LENGTH: 152
<212> TYPE: DNA
<213> ORGANISM: Artificial Sequence
<220> FEATURE:
<223> OTHER INFORMATION: target_10X_oligo_182

<400> SEQUENCE: 323
gaatcctagt acaagtggcc ggtctctata agctgggaga actctgaact ggaccacatc    60
gtcccacgga ctgatggcgg atcaaatcgc cacgagaatc tggccattac ttgcggcgca   120
tgtaacgaga ccgacatcca atccggacga ta                                 152

<210> SEQ ID NO 324
<211> LENGTH: 152
<212> TYPE: DNA
<213> ORGANISM: Artificial Sequence
<220> FEATURE:
<223> OTHER INFORMATION: target_10X_oligo_183

<400> SEQUENCE: 324
gaatcctagt acaagtggcc ggtctcgaga actctgaact ggaccacatc gtcccacgga    60
ctgatggcgg atcaaatcgc cacgagaatc tggccattac ttgcggcgca tgtaacaagg   120
agaaaggaga ccgacatcca atccggacga ta                                 152

<210> SEQ ID NO 325
<211> LENGTH: 152
<212> TYPE: DNA
<213> ORGANISM: Artificial Sequence
<220> FEATURE:
<223> OTHER INFORMATION: target_10X_oligo_184

<400> SEQUENCE: 325
gaatcctagt acaagtggcc ggtctcaact ggaccacatc gtcccacgga ctgatggcgg    60
```

```
atcaaatcgc cacgagaatc tggccattac ttgcggcgca tgtaacaagg agaaaggtcg    120
acggccgaga ccgacatcca atccggacga ta                                  152
```

<210> SEQ ID NO 326
<211> LENGTH: 152
<212> TYPE: DNA
<213> ORGANISM: Artificial Sequence
<220> FEATURE:
<223> OTHER INFORMATION: target_10X_oligo_185

<400> SEQUENCE: 326

```
gaatcctagt acaagtggcc ggtctccatc gtcccacgga ctgatggcgg atcaaatcgc    60
cacgagaatc tggccattac ttgcggcgca tgtaacaagg agaaaggtcg acggccgttt    120
gcgagtgaga ccgacatcca atccggacga ta                                  152
```

<210> SEQ ID NO 327
<211> LENGTH: 152
<212> TYPE: DNA
<213> ORGANISM: Artificial Sequence
<220> FEATURE:
<223> OTHER INFORMATION: target_10X_oligo_186

<400> SEQUENCE: 327

```
gaatcctagt acaagtggcc ggtctccgga ctgatggcgg atcaaatcgc cacgagaatc    60
tggccattac ttgcggcgca tgtaacaagg agaaaggtcg acggccgttt gcgagttggg    120
ccgagagaga ccgacatcca atccggacga ta                                  152
```

<210> SEQ ID NO 328
<211> LENGTH: 152
<212> TYPE: DNA
<213> ORGANISM: Artificial Sequence
<220> FEATURE:
<223> OTHER INFORMATION: target_10X_oligo_187

<400> SEQUENCE: 328

```
gaatcctagt acaagtggcc ggtctcgcgg atcaaatcgc cacgagaatc tggccattac    60
ttgcggcgca tgtaacaagg agaaaggtcg acggccgttt gcgagttggg ccgagacgtc    120
aaataggaga ccgacatcca atccggacga ta                                  152
```

<210> SEQ ID NO 329
<211> LENGTH: 152
<212> TYPE: DNA
<213> ORGANISM: Artificial Sequence
<220> FEATURE:
<223> OTHER INFORMATION: target_10X_oligo_188

<400> SEQUENCE: 329

```
gaatcctagt acaagtggcc ggtctctcgc cacgagaatc tggccattac ttgcggcgca    60
tgtaacaagg agaaaggtcg acggccgttt gcgagttggg ccgagacgtc aaataggdtg    120
cagctggaga ccgacatcca atccggacga ta                                  152
```

<210> SEQ ID NO 330
<211> LENGTH: 152
<212> TYPE: DNA
<213> ORGANISM: Artificial Sequence
<220> FEATURE:
<223> OTHER INFORMATION: target_10X_oligo_189

<400> SEQUENCE: 330

```
gaatcctagt acaagtggcc ggtctcaatc tggccattac ttgcggcgca tgtaacaagg    60
```
agaaaggtcg acggccgttt gcgagttggg ccgagacgtc aaatagggtg cagctgaggg    120
atgtcagaga ccgacatcca atccggacga ta    152

<210> SEQ ID NO 331
<211> LENGTH: 152
<212> TYPE: DNA
<213> ORGANISM: Artificial Sequence
<220> FEATURE:
<223> OTHER INFORMATION: target_10X_oligo_190

<400> SEQUENCE: 331
gaatcctagt acaagtggcc ggtctcttac ttgcggcgca tgtaacaagg agaaaggtcg    60
acggccgttt gcgagttggg ccgagacgtc aaatagggtg cagctgaggg atgtcatcga    120
tcgcgtgaga ccgacatcca atccggacga ta    152

<210> SEQ ID NO 332
<211> LENGTH: 152
<212> TYPE: DNA
<213> ORGANISM: Artificial Sequence
<220> FEATURE:
<223> OTHER INFORMATION: target_10X_oligo_191

<400> SEQUENCE: 332
gaatcctagt acaagtggcc ggtctccgca tgtaacaagg agaaaggtcg acggccgttt    60
gcgagttggg ccgagacgtc aaatagggtg cagctgaggg atgtcatcga tcgcgtgcag    120
aaactcgaga ccgacatcca atccggacga ta    152

<210> SEQ ID NO 333
<211> LENGTH: 152
<212> TYPE: DNA
<213> ORGANISM: Artificial Sequence
<220> FEATURE:
<223> OTHER INFORMATION: target_10X_oligo_192

<400> SEQUENCE: 333
gaatcctagt acaagtggcc ggtctcaagg agaaaggtcg acggccgttt gcgagttggg    60
ccgagacgtc aaatagggtg cagctgaggg atgtcatcga tcgcgtgcag aaactcaaat    120
actcaggaga ccgacatcca atccggacga ta    152

<210> SEQ ID NO 334
<211> LENGTH: 152
<212> TYPE: DNA
<213> ORGANISM: Artificial Sequence
<220> FEATURE:
<223> OTHER INFORMATION: target_10X_oligo_193

<400> SEQUENCE: 334
gaatcctagt acaagtggcc ggtctcgtcg acggccgttt gcgagttggg ccgagacgtc    60
aaatagggtg cagctgaggg atgtcatcga tcgcgtgcag aaactcaaat actcaggaaa    120
tatgtagaga ccgacatcca atccggacga ta    152

<210> SEQ ID NO 335
<211> LENGTH: 152
<212> TYPE: DNA
<213> ORGANISM: Artificial Sequence
<220> FEATURE:
<223> OTHER INFORMATION: target_10X_oligo_194

<400> SEQUENCE: 335

```
gaatcctagt acaagtggcc ggtctcgttt gcgagttggg ccgagacgtc aaatagggtg         60
cagctgaggg atgtcatcga tcgcgtgcag aaactcaaat actcaggaaa tatgtattgg        120
accagagaga ccgacatcca atccggacga ta                                      152
```

<210> SEQ ID NO 336
<211> LENGTH: 152
<212> TYPE: DNA
<213> ORGANISM: Artificial Sequence
<220> FEATURE:
<223> OTHER INFORMATION: target_10X_oligo_195

<400> SEQUENCE: 336

```
gaatcctagt acaagtggcc ggtctctggg ccgagacgtc aaatagggtg cagctgaggg         60
atgtcatcga tcgcgtgcag aaactcaaat actcaggaaa tatgtattgg accagagacg        120
aatttagaga ccgacatcca atccggacga ta                                      152
```

<210> SEQ ID NO 337
<211> LENGTH: 152
<212> TYPE: DNA
<213> ORGANISM: Artificial Sequence
<220> FEATURE:
<223> OTHER INFORMATION: target_10X_oligo_196

<400> SEQUENCE: 337

```
gaatcctagt acaagtggcc ggtctccgtc aaatagggtg cagctgaggg atgtcatcga         60
tcgcgtgcag aaactcaaat actcaggaaa tatgtattgg accagagacg aatttagcag        120
atacaagaga ccgacatcca atccggacga ta                                      152
```

<210> SEQ ID NO 338
<211> LENGTH: 152
<212> TYPE: DNA
<213> ORGANISM: Artificial Sequence
<220> FEATURE:
<223> OTHER INFORMATION: target_10X_oligo_197

<400> SEQUENCE: 338

```
gaatcctagt acaagtggcc ggtctcggtg cagctgaggg atgtcatcga tcgcgtgcag         60
aaactcaaat actcaggaaa tatgtattgg accagagacg aatttagcag atacaaaaag        120
tctgtggaga ccgacatcca atccggacga ta                                      152
```

<210> SEQ ID NO 339
<211> LENGTH: 152
<212> TYPE: DNA
<213> ORGANISM: Artificial Sequence
<220> FEATURE:
<223> OTHER INFORMATION: target_10X_oligo_198

<400> SEQUENCE: 339

```
gaatcctagt acaagtggcc ggtctcaggg atgtcatcga tcgcgtgcag aaactcaaat         60
actcaggaaa tatgtattgg accagagacg aatttagcag atacaaaaag tctgtggtag        120
ctagacgaga ccgacatcca atccggacga ta                                      152
```

<210> SEQ ID NO 340
<211> LENGTH: 152
<212> TYPE: DNA
<213> ORGANISM: Artificial Sequence
<220> FEATURE:
<223> OTHER INFORMATION: target_10X_oligo_199

<400> SEQUENCE: 340

```
gaatcctagt acaagtggcc ggtctctcga tcgcgtgcag aaactcaaat actcaggaaa      60
tatgtattgg accagagacg aatttagcag atacaaaaag tctgtggtag ctagactcaa     120
gcgaaggaga ccgacatcca atccggacga ta                                   152
```

<210> SEQ ID NO 341
<211> LENGTH: 152
<212> TYPE: DNA
<213> ORGANISM: Artificial Sequence
<220> FEATURE:
<223> OTHER INFORMATION: target_10X_oligo_200

<400> SEQUENCE: 341

```
gaatcctagt acaagtggcc ggtctcgcag aaactcaaat actcaggaaa tatgtattgg      60
accagagacg aatttagcag atacaaaaag tctgtggtag ctagactcaa gcgaaggacg     120
tcagacgaga ccgacatcca atccggacga ta                                   152
```

<210> SEQ ID NO 342
<211> LENGTH: 152
<212> TYPE: DNA
<213> ORGANISM: Artificial Sequence
<220> FEATURE:
<223> OTHER INFORMATION: target_10X_oligo_201

<400> SEQUENCE: 342

```
gaatcctagt acaagtggcc ggtctcaaat actcaggaaa tatgtattgg accagagacg      60
aatttagcag atacaaaaag tctgtggtag ctagactcaa gcgaaggacg tcagaccccg     120
aggtcagaga ccgacatcca atccggacga ta                                   152
```

<210> SEQ ID NO 343
<211> LENGTH: 152
<212> TYPE: DNA
<213> ORGANISM: Artificial Sequence
<220> FEATURE:
<223> OTHER INFORMATION: target_10X_oligo_202

<400> SEQUENCE: 343

```
gaatcctagt acaagtggcc ggtctcgaaa tatgtattgg accagagacg aatttagcag      60
atacaaaaag tctgtggtag ctagactcaa gcgaaggacg tcagaccccg aggtcatcca     120
gagtatgaga ccgacatcca atccggacga ta                                   152
```

<210> SEQ ID NO 344
<211> LENGTH: 152
<212> TYPE: DNA
<213> ORGANISM: Artificial Sequence
<220> FEATURE:
<223> OTHER INFORMATION: target_10X_oligo_203

<400> SEQUENCE: 344

```
gaatcctagt acaagtggcc ggtctcttgg accagagacg aatttagcag atacaaaaag      60
tctgtggtag ctagactcaa gcgaaggacg tcagaccccg aggtcatcca gagtattgag     120
agtaccgaga ccgacatcca atccggacga ta                                   152
```

<210> SEQ ID NO 345
<211> LENGTH: 152
<212> TYPE: DNA
<213> ORGANISM: Artificial Sequence
<220> FEATURE:
<223> OTHER INFORMATION: target_10X_oligo_204

```
<400> SEQUENCE: 345
gaatcctagt acaagtggcc ggtctcgacg aatttagcag atacaaaaag tctgtggtag    60
ctagactcaa gcgaaggacg tcagaccccg aggtcatcca gagtattgag agtaccggct   120
atgccggaga ccgacatcca atccggacga ta                                 152

<210> SEQ ID NO 346
<211> LENGTH: 152
<212> TYPE: DNA
<213> ORGANISM: Artificial Sequence
<220> FEATURE:
<223> OTHER INFORMATION: target_10X_oligo_205

<400> SEQUENCE: 346
gaatcctagt acaagtggcc ggtctcgcag atacaaaaag tctgtggtag ctagactcaa    60
gcgaaggacg tcagaccccg aggtcatcca gagtattgag agtaccggct atgccgcagt   120
ggcgctgaga ccgacatcca atccggacga ta                                 152

<210> SEQ ID NO 347
<211> LENGTH: 152
<212> TYPE: DNA
<213> ORGANISM: Artificial Sequence
<220> FEATURE:
<223> OTHER INFORMATION: target_10X_oligo_206

<400> SEQUENCE: 347
gaatcctagt acaagtggcc ggtctcaaag tctgtggtag ctagactcaa gcgaaggacg    60
tcagaccccg aggtcatcca gagtattgag agtaccggct atgccgcagt ggcgctccga   120
gacagagaga ccgacatcca atccggacga ta                                 152

<210> SEQ ID NO 348
<211> LENGTH: 152
<212> TYPE: DNA
<213> ORGANISM: Artificial Sequence
<220> FEATURE:
<223> OTHER INFORMATION: target_10X_oligo_207

<400> SEQUENCE: 348
gaatcctagt acaagtggcc ggtctcgtag ctagactcaa gcgaaggacg tcagaccccg    60
aggtcatcca gagtattgag agtaccggct atgccgcagt ggcgctccga gacagactgc   120
tgagctgaga ccgacatcca atccggacga ta                                 152

<210> SEQ ID NO 349
<211> LENGTH: 152
<212> TYPE: DNA
<213> ORGANISM: Artificial Sequence
<220> FEATURE:
<223> OTHER INFORMATION: target_10X_oligo_208

<400> SEQUENCE: 349
gaatcctagt acaagtggcc ggtctctcaa gcgaaggacg tcagaccccg aggtcatcca    60
gagtattgag agtaccggct atgccgcagt ggcgctccga gacagactgc tgagctacgg   120
cgagaagaga ccgacatcca atccggacga ta                                 152

<210> SEQ ID NO 350
<211> LENGTH: 152
<212> TYPE: DNA
<213> ORGANISM: Artificial Sequence
<220> FEATURE:
<223> OTHER INFORMATION: target_10X_oligo_209
```

```
<400> SEQUENCE: 350
gaatcctagt acaagtggcc ggtctcgacg tcagaccccg aggtcatcca gagtattgag      60
agtaccggct atgccgcagt ggcgctccga gacagactgc tgagctacgg cgagaaaaac     120
ggggtggaga ccgacatcca atccggacga ta                                    152

<210> SEQ ID NO 351
<211> LENGTH: 152
<212> TYPE: DNA
<213> ORGANISM: Artificial Sequence
<220> FEATURE:
<223> OTHER INFORMATION: target_10X_oligo_210

<400> SEQUENCE: 351
gaatcctagt acaagtggcc ggtctccccg aggtcatcca gagtattgag agtaccggct      60
atgccgcagt ggcgctccga gacagactgc tgagctacgg cgagaaaaac ggggtggctc     120
aggtcggaga ccgacatcca atccggacga ta                                    152

<210> SEQ ID NO 352
<211> LENGTH: 152
<212> TYPE: DNA
<213> ORGANISM: Artificial Sequence
<220> FEATURE:
<223> OTHER INFORMATION: target_10X_oligo_211

<400> SEQUENCE: 352
gaatcctagt acaagtggcc ggtctctcca gagtattgag agtaccggct atgccgcagt      60
ggcgctccga gacagactgc tgagctacgg cgagaaaaac ggggtggctc aggtcgcagt     120
ctttcggaga ccgacatcca atccggacga ta                                    152

<210> SEQ ID NO 353
<211> LENGTH: 152
<212> TYPE: DNA
<213> ORGANISM: Artificial Sequence
<220> FEATURE:
<223> OTHER INFORMATION: target_10X_oligo_212

<400> SEQUENCE: 353
gaatcctagt acaagtggcc ggtctctgag agtaccggct atgccgcagt ggcgctccga      60
gacagactgc tgagctacgg cgagaaaaac ggggtggctc aggtcgcagt ctttcgcgga     120
ggcgttgaga ccgacatcca atccggacga ta                                    152

<210> SEQ ID NO 354
<211> LENGTH: 152
<212> TYPE: DNA
<213> ORGANISM: Artificial Sequence
<220> FEATURE:
<223> OTHER INFORMATION: target_10X_oligo_213

<400> SEQUENCE: 354
gaatcctagt acaagtggcc ggtctcggct atgccgcagt ggcgctccga gacagactgc      60
tgagctacgg cgagaaaaac ggggtggctc aggtcgcagt ctttcgcgga ggcgttacag     120
ctgaaggaga ccgacatcca atccggacga ta                                    152

<210> SEQ ID NO 355
<211> LENGTH: 152
<212> TYPE: DNA
<213> ORGANISM: Artificial Sequence
<220> FEATURE:
```

<223> OTHER INFORMATION: target_10X_oligo_214

<400> SEQUENCE: 355
gaatcctagt acaagtggcc ggtctccagt ggcgctccga dacagactgc tgagctacgg    60
cgagaaaaac ggggtggctc aggtcgcagt ctttcgcgga ggcgttacag ctgaagcgag   120
acgctggaga ccgacatcca atccggacga ta                                152

<210> SEQ ID NO 356
<211> LENGTH: 152
<212> TYPE: DNA
<213> ORGANISM: Artificial Sequence
<220> FEATURE:
<223> OTHER INFORMATION: target_10X_oligo_215

<400> SEQUENCE: 356
gaatcctagt acaagtggcc ggtctcccga dacagactgc tgagctacgg cgagaaaaac    60
ggggtggctc aggtcgcagt ctttcgcgga ggcgttacag ctgaagcgag acgctggctt   120
gatatagaga ccgacatcca atccggacga ta                                152

<210> SEQ ID NO 357
<211> LENGTH: 152
<212> TYPE: DNA
<213> ORGANISM: Artificial Sequence
<220> FEATURE:
<223> OTHER INFORMATION: target_10X_oligo_216

<400> SEQUENCE: 357
gaatcctagt acaagtggcc ggtctcctgc tgagctacgg cgagaaaaac ggggtggctc    60
aggtcgcagt ctttcgcgga ggcgttacag ctgaagcgag acgctggctt gatatatcca   120
tagagagaga ccgacatcca atccggacga ta                                152

<210> SEQ ID NO 358
<211> LENGTH: 152
<212> TYPE: DNA
<213> ORGANISM: Artificial Sequence
<220> FEATURE:
<223> OTHER INFORMATION: target_10X_oligo_217

<400> SEQUENCE: 358
gaatcctagt acaagtggcc ggtctcacgg cgagaaaaac ggggtggctc aggtcgcagt    60
ctttcgcgga ggcgttacag ctgaagcgag acgctggctt gatatatcca tagagaggct   120
gttttcgaga ccgacatcca atccggacga ta                                152

<210> SEQ ID NO 359
<211> LENGTH: 152
<212> TYPE: DNA
<213> ORGANISM: Artificial Sequence
<220> FEATURE:
<223> OTHER INFORMATION: target_10X_oligo_218

<400> SEQUENCE: 359
gaatcctagt acaagtggcc ggtctcaaac ggggtggctc aggtcgcagt ctttcgcgga    60
ggcgttacag ctgaagcgag acgctggctt gatatatcca tagagaggct gttttctagg   120
gtggccgaga ccgacatcca atccggacga ta                                152

<210> SEQ ID NO 360
<211> LENGTH: 152
<212> TYPE: DNA
<213> ORGANISM: Artificial Sequence
<220> FEATURE:
<223> OTHER INFORMATION: target_10X_oligo_219

<400> SEQUENCE: 360
gaatcctagt acaagtggcc ggtctcgctc aggtcgcagt ctttcgcgga ggcgttacag    60
ctgaagcgag acgctggctt gatatatcca tagagaggct gttttctagg gtggccattt   120
ttgcgcgaga ccgacatcca atccggacga ta                                 152

<210> SEQ ID NO 361
<211> LENGTH: 152
<212> TYPE: DNA
<213> ORGANISM: Artificial Sequence
<220> FEATURE:
<223> OTHER INFORMATION: target_10X_oligo_220

<400> SEQUENCE: 361
gaatcctagt acaagtggcc ggtctccagt ctttcgcgga ggcgttacag ctgaagcgag    60
acgctggctt gatatatcca tagagaggct gttttctagg gtggccattt ttgcgcagtc   120
cactaggaga ccgacatcca atccggacga ta                                 152

<210> SEQ ID NO 362
<211> LENGTH: 152
<212> TYPE: DNA
<213> ORGANISM: Artificial Sequence
<220> FEATURE:
<223> OTHER INFORMATION: target_10X_oligo_221

<400> SEQUENCE: 362
gaatcctagt acaagtggcc ggtctccgga ggcgttacag ctgaagcgag acgctggctt    60
gatatatcca tagagaggct gttttctagg gtggccattt ttgcgcagtc cactagcaca   120
aagagggaga ccgacatcca atccggacga ta                                 152

<210> SEQ ID NO 363
<211> LENGTH: 152
<212> TYPE: DNA
<213> ORGANISM: Artificial Sequence
<220> FEATURE:
<223> OTHER INFORMATION: target_10X_oligo_222

<400> SEQUENCE: 363
gaatcctagt acaagtggcc ggtctcacag ctgaagcgag acgctggctt gatatatcca    60
tagagaggct gttttctagg gtggccattt ttgcgcagtc cactagcaca aagaggctcg   120
acagacgaga ccgacatcca atccggacga ta                                 152

<210> SEQ ID NO 364
<211> LENGTH: 152
<212> TYPE: DNA
<213> ORGANISM: Artificial Sequence
<220> FEATURE:
<223> OTHER INFORMATION: target_10X_oligo_223

<400> SEQUENCE: 364
gaatcctagt acaagtggcc ggtctccgag acgctggctt gatatatcca tagagaggct    60
gttttctagg gtggccattt ttgcgcagtc cactagcaca aagaggctcg acagacgaca   120
tcatgcgaga ccgacatcca atccggacga ta                                 152

<210> SEQ ID NO 365
<211> LENGTH: 152
<212> TYPE: DNA

<213> ORGANISM: Artificial Sequence
<220> FEATURE:
<223> OTHER INFORMATION: target_10X_oligo_224

<400> SEQUENCE: 365
gaatcctagt acaagtggcc ggtctcgctt gatatatcca tagagaggct gttttctagg    60
gtggccattt ttgcgcagtc cactagcaca aagaggctcg acagacgaca tcatgccgtg   120
gatgctgaga ccgacatcca atccggacga ta                                 152

<210> SEQ ID NO 366
<211> LENGTH: 152
<212> TYPE: DNA
<213> ORGANISM: Artificial Sequence
<220> FEATURE:
<223> OTHER INFORMATION: target_10X_oligo_225

<400> SEQUENCE: 366
gaatcctagt acaagtggcc ggtctctcca tagagaggct gttttctagg gtggccattt    60
ttgcgcagtc cactagcaca aagaggctcg acagacgaca tcatgccgtg gatgctgtgg   120
ttctgagaga ccgacatcca atccggacga ta                                 152

<210> SEQ ID NO 367
<211> LENGTH: 152
<212> TYPE: DNA
<213> ORGANISM: Artificial Sequence
<220> FEATURE:
<223> OTHER INFORMATION: target_10X_oligo_226

<400> SEQUENCE: 367
gaatcctagt acaagtggcc ggtctcggct gttttctagg gtggccattt ttgcgcagtc    60
cactagcaca aagaggctcg acagacgaca tcatgccgtg gatgctgtgg ttctgacaac   120
gctcacgaga ccgacatcca atccggacga ta                                 152

<210> SEQ ID NO 368
<211> LENGTH: 152
<212> TYPE: DNA
<213> ORGANISM: Artificial Sequence
<220> FEATURE:
<223> OTHER INFORMATION: target_10X_oligo_227

<400> SEQUENCE: 368
gaatcctagt acaagtggcc ggtctctagg gtggccattt ttgcgcagtc cactagcaca    60
aagaggctcg acagacgaca tcatgccgtg gatgctgtgg ttctgacaac gctcacacct   120
ggtgttgaga ccgacatcca atccggacga ta                                 152

<210> SEQ ID NO 369
<211> LENGTH: 152
<212> TYPE: DNA
<213> ORGANISM: Artificial Sequence
<220> FEATURE:
<223> OTHER INFORMATION: target_10X_oligo_228

<400> SEQUENCE: 369
gaatcctagt acaagtggcc ggtctcattt ttgcgcagtc cactagcaca aagaggctcg    60
acagacgaca tcatgccgtg gatgctgtgg ttctgacaac gctcacacct ggtgttgcga   120
agacttgaga ccgacatcca atccggacga ta                                 152

<210> SEQ ID NO 370
<211> LENGTH: 152

<212> TYPE: DNA
<213> ORGANISM: Artificial Sequence
<220> FEATURE:
<223> OTHER INFORMATION: target_10X_oligo_229

<400> SEQUENCE: 370
gaatcctagt acaagtggcc ggtctcagtc cactagcaca aagaggctcg acagacgaca    60
tcatgccgtg gatgctgtgg ttctgacaac gctcacacct ggtgttgcga agactttggc   120
tgatgcgaga ccgacatcca atccggacga ta                                 152

<210> SEQ ID NO 371
<211> LENGTH: 152
<212> TYPE: DNA
<213> ORGANISM: Artificial Sequence
<220> FEATURE:
<223> OTHER INFORMATION: target_10X_oligo_230

<400> SEQUENCE: 371
gaatcctagt acaagtggcc ggtctccaca aagaggctcg acagacgaca tcatgccgtg    60
gatgctgtgg ttctgacaac gctcacacct ggtgttgcga agactttggc tgatgcgcgc   120
agcagagaga ccgacatcca atccggacga ta                                 152

<210> SEQ ID NO 372
<211> LENGTH: 152
<212> TYPE: DNA
<213> ORGANISM: Artificial Sequence
<220> FEATURE:
<223> OTHER INFORMATION: target_10X_oligo_231

<400> SEQUENCE: 372
gaatcctagt acaagtggcc ggtctcctcg acagacgaca tcatgccgtg gatgctgtgg    60
ttctgacaac gctcacacct ggtgttgcga agactttggc tgatgcgcgc agcagacgag   120
ttagcggaga ccgacatcca atccggacga ta                                 152

<210> SEQ ID NO 373
<211> LENGTH: 152
<212> TYPE: DNA
<213> ORGANISM: Artificial Sequence
<220> FEATURE:
<223> OTHER INFORMATION: target_10X_oligo_232

<400> SEQUENCE: 373
gaatcctagt acaagtggcc ggtctcgaca tcatgccgtg gatgctgtgg ttctgacaac    60
gctcacacct ggtgttgcga agactttggc tgatgcgcgc agcagacgag ttagcgccga   120
gttctggaga ccgacatcca atccggacga ta                                 152

<210> SEQ ID NO 374
<211> LENGTH: 152
<212> TYPE: DNA
<213> ORGANISM: Artificial Sequence
<220> FEATURE:
<223> OTHER INFORMATION: target_10X_oligo_233

<400> SEQUENCE: 374
gaatcctagt acaagtggcc ggtctccgtg gatgctgtgg ttctgacaac gctcacacct    60
ggtgttgcga agactttggc tgatgcgcgc agcagacgag ttagcgccga gttctggcgg   120
aggcctgaga ccgacatcca atccggacga ta                                 152

<210> SEQ ID NO 375

```
<211> LENGTH: 152
<212> TYPE: DNA
<213> ORGANISM: Artificial Sequence
<220> FEATURE:
<223> OTHER INFORMATION: target_10X_oligo_234

<400> SEQUENCE: 375
gaatcctagt acaagtggcc ggtctcgtgg ttctgacaac gctcacacct ggtgttgcga      60
agactttggc tgatgcgcgc agcagacgag ttagcgccga gttctggcgg aggcctagcg     120
acgtcagaga ccgacatcca atccggacga ta                                   152

<210> SEQ ID NO 376
<211> LENGTH: 152
<212> TYPE: DNA
<213> ORGANISM: Artificial Sequence
<220> FEATURE:
<223> OTHER INFORMATION: target_10X_oligo_235

<400> SEQUENCE: 376
gaatcctagt acaagtggcc ggtctccaac gctcacacct ggtgttgcga agactttggc      60
tgatgcgcgc agcagacgag ttagcgccga gttctggcgg aggcctagcg acgtcaaccg     120
acacaggaga ccgacatcca atccggacga ta                                   152

<210> SEQ ID NO 377
<211> LENGTH: 152
<212> TYPE: DNA
<213> ORGANISM: Artificial Sequence
<220> FEATURE:
<223> OTHER INFORMATION: target_10X_oligo_236

<400> SEQUENCE: 377
gaatcctagt acaagtggcc ggtctcacct ggtgttgcga agactttggc tgatgcgcgc      60
agcagacgag ttagcgccga gttctggcgg aggcctagcg acgtcaaccg acacagcact     120
gaggaggaga ccgacatcca atccggacga ta                                   152

<210> SEQ ID NO 378
<211> LENGTH: 152
<212> TYPE: DNA
<213> ORGANISM: Artificial Sequence
<220> FEATURE:
<223> OTHER INFORMATION: target_10X_oligo_237

<400> SEQUENCE: 378
gaatcctagt acaagtggcc ggtctcgcga agactttggc tgatgcgcgc agcagacgag      60
ttagcgccga gttctggcgg aggcctagcg acgtcaaccg acacagcact gaggagccgc     120
agagccgaga ccgacatcca atccggacga ta                                   152

<210> SEQ ID NO 379
<211> LENGTH: 152
<212> TYPE: DNA
<213> ORGANISM: Artificial Sequence
<220> FEATURE:
<223> OTHER INFORMATION: target_10X_oligo_238

<400> SEQUENCE: 379
gaatcctagt acaagtggcc ggtctctggc tgatgcgcgc agcagacgag ttagcgccga      60
gttctggcgg aggcctagcg acgtcaaccg acacagcact gaggagccgc agagcccggc     120
ctacaggaga ccgacatcca atccggacga ta                                   152
```

<210> SEQ ID NO 380
<211> LENGTH: 152
<212> TYPE: DNA
<213> ORGANISM: Artificial Sequence
<220> FEATURE:
<223> OTHER INFORMATION: target_10X_oligo_239

<400> SEQUENCE: 380

```
gaatcctagt acaagtggcc ggtctcgcgc agcagacgag ttagcgccga gttctggcgg      60
aggcctagcg acgtcaaccg acacagcact gaggagccgc agagcccggc ctacaggcaa     120
tggaaggaga ccgacatcca atccggacga ta                                   152
```

<210> SEQ ID NO 381
<211> LENGTH: 152
<212> TYPE: DNA
<213> ORGANISM: Artificial Sequence
<220> FEATURE:
<223> OTHER INFORMATION: target_10X_oligo_240

<400> SEQUENCE: 381

```
gaatcctagt acaagtggcc ggtctccgag ttagcgccga gttctggcgg aggcctagcg      60
acgtcaaccg acacagcact gaggagccgc agagcccggc ctacaggcaa tggaaggaat     120
cttgttgaga ccgacatcca atccggacga ta                                   152
```

<210> SEQ ID NO 382
<211> LENGTH: 152
<212> TYPE: DNA
<213> ORGANISM: Artificial Sequence
<220> FEATURE:
<223> OTHER INFORMATION: target_10X_oligo_241

<400> SEQUENCE: 382

```
gaatcctagt acaagtggcc ggtctcccga gttctggcgg aggcctagcg acgtcaaccg      60
acacagcact gaggagccgc agagcccggc ctacaggcaa tggaaggaat cttgttctgg     120
tctggggaga ccgacatcca atccggacga ta                                   152
```

<210> SEQ ID NO 383
<211> LENGTH: 152
<212> TYPE: DNA
<213> ORGANISM: Artificial Sequence
<220> FEATURE:
<223> OTHER INFORMATION: target_10X_oligo_242

<400> SEQUENCE: 383

```
gaatcctagt acaagtggcc ggtctcgcgg aggcctagcg acgtcaaccg acacagcact      60
gaggagccgc agagcccggc ctacaggcaa tggaaggaat cttgttctgg tctgggcgac     120
ttgctcgaga ccgacatcca atccggacga ta                                   152
```

<210> SEQ ID NO 384
<211> LENGTH: 152
<212> TYPE: DNA
<213> ORGANISM: Artificial Sequence
<220> FEATURE:
<223> OTHER INFORMATION: target_10X_oligo_243

<400> SEQUENCE: 384

```
gaatcctagt acaagtggcc ggtctcagcg acgtcaaccg acacagcact gaggagccgc      60
agagcccggc ctacaggcaa tggaaggaat cttgttctgg tctgggcgac ttgctcattt     120
ccactggaga ccgacatcca atccggacga ta                                   152
```

<210> SEQ ID NO 385
<211> LENGTH: 152
<212> TYPE: DNA
<213> ORGANISM: Artificial Sequence
<220> FEATURE:
<223> OTHER INFORMATION: target_10X_oligo_244

<400> SEQUENCE: 385
gaatcctagt acaagtggcc ggtctcaccg acacagcact gaggagccgc agagcccggc      60
ctacaggcaa tggaaggaat cttgttctgg tctgggcgac ttgctcattt ccactgctgc     120
acgagagaga ccgacatcca atccggacga ta                                  152

<210> SEQ ID NO 386
<211> LENGTH: 152
<212> TYPE: DNA
<213> ORGANISM: Artificial Sequence
<220> FEATURE:
<223> OTHER INFORMATION: target_10X_oligo_245

<400> SEQUENCE: 386
gaatcctagt acaagtggcc ggtctccact gaggagccgc agagcccggc ctacaggcaa      60
tggaaggaat cttgttctgg tctgggcgac ttgctcattt ccactgctgc acgagattcc     120
attgcagaga ccgacatcca atccggacga ta                                  152

<210> SEQ ID NO 387
<211> LENGTH: 152
<212> TYPE: DNA
<213> ORGANISM: Artificial Sequence
<220> FEATURE:
<223> OTHER INFORMATION: target_10X_oligo_246

<400> SEQUENCE: 387
gaatcctagt acaagtggcc ggtctcccgc agagcccggc ctacaggcaa tggaaggaat      60
cttgttctgg tctgggcgac ttgctcattt ccactgctgc acgagattcc attgcagtag     120
ctgcacgaga ccgacatcca atccggacga ta                                  152

<210> SEQ ID NO 388
<211> LENGTH: 152
<212> TYPE: DNA
<213> ORGANISM: Artificial Sequence
<220> FEATURE:
<223> OTHER INFORMATION: target_10X_oligo_247

<400> SEQUENCE: 388
gaatcctagt acaagtggcc ggtctccggc ctacaggcaa tggaaggaat cttgttctgg      60
tctgggcgac ttgctcattt ccactgctgc acgagattcc attgcagtag ctgcaccctt     120
gaggctgaga ccgacatcca atccggacga ta                                  152

<210> SEQ ID NO 389
<211> LENGTH: 152
<212> TYPE: DNA
<213> ORGANISM: Artificial Sequence
<220> FEATURE:
<223> OTHER INFORMATION: target_10X_oligo_248

<400> SEQUENCE: 389
gaatcctagt acaagtggcc ggtctcgcaa tggaaggaat cttgttctgg tctgggcgac      60
ttgctcattt ccactgctgc acgagattcc attgcagtag ctgcaccctt gaggctccgg     120
ccgactgaga ccgacatcca atccggacga ta                                  152

```
<210> SEQ ID NO 390
<211> LENGTH: 152
<212> TYPE: DNA
<213> ORGANISM: Artificial Sequence
<220> FEATURE:
<223> OTHER INFORMATION: target_10X_oligo_249

<400> SEQUENCE: 390
gaatcctagt acaagtggcc ggtctcgaat cttgttctgg tctgggcgac ttgctcattt      60
ccactgctgc acgagattcc attgcagtag ctgcacccett gaggctccgg ccgactggag    120
cactgcgaga ccgacatcca atccggacga ta                                   152

<210> SEQ ID NO 391
<211> LENGTH: 152
<212> TYPE: DNA
<213> ORGANISM: Artificial Sequence
<220> FEATURE:
<223> OTHER INFORMATION: target_10X_oligo_250

<400> SEQUENCE: 391
gaatcctagt acaagtggcc ggtctcctgg tctgggcgac ttgctcattt ccactgctgc      60
acgagattcc attgcagtag ctgcacccett gaggctccgg ccgactggag cactgcacga    120
agaaacgaga ccgacatcca atccggacga ta                                   152

<210> SEQ ID NO 392
<211> LENGTH: 152
<212> TYPE: DNA
<213> ORGANISM: Artificial Sequence
<220> FEATURE:
<223> OTHER INFORMATION: target_10X_oligo_251

<400> SEQUENCE: 392
gaatcctagt acaagtggcc ggtctccgac ttgctcattt ccactgctgc acgagattcc      60
attgcagtag ctgcacccett gaggctccgg ccgactggag cactgcacga agaaaccctt    120
agggccgaga ccgacatcca atccggacga ta                                   152

<210> SEQ ID NO 393
<211> LENGTH: 152
<212> TYPE: DNA
<213> ORGANISM: Artificial Sequence
<220> FEATURE:
<223> OTHER INFORMATION: target_10X_oligo_252

<400> SEQUENCE: 393
gaatcctagt acaagtggcc ggtctcattt ccactgctgc acgagattcc attgcagtag      60 ctgcacccctt gaggctccgg ccgactggag cactgcacga agaaaccctt agggccttca    120
gtgaacgaga ccgacatcca atccggacga ta                                   152

<210> SEQ ID NO 394
<211> LENGTH: 152
<212> TYPE: DNA
<213> ORGANISM: Artificial Sequence
<220> FEATURE:
<223> OTHER INFORMATION: target_10X_oligo_253

<400> SEQUENCE: 394
gaatcctagt acaagtggcc ggtctcctgc acgagattcc attgcagtag ctgcacccctt     60 gaggctccgg ccgactggag cactgcacga agaaaccctt agggccttca gtgaacacac    120
```
ggtcgggaga ccgacatcca atccggacga ta                                      152

<210> SEQ ID NO 395
<211> LENGTH: 152
<212> TYPE: DNA
<213> ORGANISM: Artificial Sequence
<220> FEATURE:
<223> OTHER INFORMATION: target_10X_oligo_254

<400> SEQUENCE: 395
gaatcctagt acaagtggcc ggtctcttcc attgcagtag ctgcacccct gaggctccgg        60
ccgactggag cactgcacga agaaacccct agggccttca gtgaacacac ggtcggggca       120
gcctgggaga ccgacatcca atccggacga ta                                      152

<210> SEQ ID NO 396
<211> LENGTH: 152
<212> TYPE: DNA
<213> ORGANISM: Artificial Sequence
<220> FEATURE:
<223> OTHER INFORMATION: target_10X_oligo_255

<400> SEQUENCE: 396
gaatcctagt acaagtggcc ggtctcgtag ctgcacccct gaggctccgg ccgactggag        60
cactgcacga agaaacccct agggccttca gtgaacacac ggtcggggca gcctggaaag       120
gcgcaggaga ccgacatcca atccggacga ta                                      152

<210> SEQ ID NO 397
<211> LENGTH: 152
<212> TYPE: DNA
<213> ORGANISM: Artificial Sequence
<220> FEATURE:
<223> OTHER INFORMATION: target_10X_oligo_256

<400> SEQUENCE: 397
gaatcctagt acaagtggcc ggtctcccct gaggctccgg ccgactggag cactgcacga        60
agaaacccct agggccttca gtgaacacac ggtcggggca gcctggaaag gcgcagagct       120
gcgcaggaga ccgacatcca atccggacga ta                                      152

<210> SEQ ID NO 398
<211> LENGTH: 152
<212> TYPE: DNA
<213> ORGANISM: Artificial Sequence
<220> FEATURE:
<223> OTHER INFORMATION: target_10X_oligo_257

<400> SEQUENCE: 398
gaatcctagt acaagtggcc ggtctcccgg ccgactggag cactgcacga agaaacccct        60
agggccttca gtgaacacac ggtcggggca gcctggaaag gcgcagagct gcgcaggatt       120
gtggaagaga ccgacatcca atccggacga ta                                      152

<210> SEQ ID NO 399
<211> LENGTH: 152
<212> TYPE: DNA
<213> ORGANISM: Artificial Sequence
<220> FEATURE:
<223> OTHER INFORMATION: target_10X_oligo_258

<400> SEQUENCE: 399
gaatcctagt acaagtggcc ggtctcggag cactgcacga agaaacccct agggccttca        60
gtgaacacac ggtcggggca gcctggaaag gcgcagagct gcgcaggatt gtggaacccg       120

```
aagtatgaga ccgacatcca atccggacga ta                                    152

<210> SEQ ID NO 400
<211> LENGTH: 152
<212> TYPE: DNA
<213> ORGANISM: Artificial Sequence
<220> FEATURE:
<223> OTHER INFORMATION: target_10X_oligo_259

<400> SEQUENCE: 400
gaatcctagt acaagtggcc ggtctcacga agaaaccctt agggccttca gtgaacacac    60
ggtcggggca gcctggaaag gcgcagagct gcgcaggatt gtggaacccg aagtatacgc   120
cgccttgaga ccgacatcca atccggacga ta                                  152

<210> SEQ ID NO 401
<211> LENGTH: 152
<212> TYPE: DNA
<213> ORGANISM: Artificial Sequence
<220> FEATURE:
<223> OTHER INFORMATION: target_10X_oligo_260

<400> SEQUENCE: 401
gaatcctagt acaagtggcc ggtctcccct agggccttca gtgaacacac ggtcggggca    60
gcctggaaag gcgcagagct gcgcaggatt gtggaacccg aagtatacgc cgcctttctg   120
gctttggaga ccgacatcca atccggacga ta                                  152

<210> SEQ ID NO 402
<211> LENGTH: 152
<212> TYPE: DNA
<213> ORGANISM: Artificial Sequence
<220> FEATURE:
<223> OTHER INFORMATION: target_10X_oligo_261

<400> SEQUENCE: 402
gaatcctagt acaagtggcc ggtctcttca gtgaacacac ggtcggggca gcctggaaag    60
gcgcagagct gcgcaggatt gtggaacccg aagtatacgc cgcctttctg gctttgaccg   120
accctggaga ccgacatcca atccggacga ta                                  152

<210> SEQ ID NO 403
<211> LENGTH: 152
<212> TYPE: DNA
<213> ORGANISM: Artificial Sequence
<220> FEATURE:
<223> OTHER INFORMATION: target_10X_oligo_262

<400> SEQUENCE: 403
gaatcctagt acaagtggcc ggtctcacac ggtcggggca gcctggaaag gcgcagagct    60
gcgcaggatt gtggaacccg aagtatacgc cgcctttctg gctttgaccg accctggcgg   120
ccgcttgaga ccgacatcca atccggacga ta                                  152

<210> SEQ ID NO 404
<211> LENGTH: 152
<212> TYPE: DNA
<213> ORGANISM: Artificial Sequence
<220> FEATURE:
<223> OTHER INFORMATION: target_10X_oligo_263

<400> SEQUENCE: 404
gaatcctagt acaagtggcc ggtctcggca gcctggaaag gcgcagagct gcgcaggatt    60
```
gtggaacccg aagtatacgc cgcctttctg gctttgaccg accctggcgg ccgcttcctg    120
aaagtggaga ccgacatcca atccggacga ta    152

<210> SEQ ID NO 405
<211> LENGTH: 152
<212> TYPE: DNA
<213> ORGANISM: Artificial Sequence
<220> FEATURE:
<223> OTHER INFORMATION: target_10X_oligo_264

<400> SEQUENCE: 405
gaatcctagt acaagtggcc ggtctcaaag gcgcagagct gcgcaggatt gtggaacccg    60
aagtatacgc cgcctttctg gctttgaccg accctggcgg ccgcttcctg aaagtgtcac    120
cttcaggaga ccgacatcca atccggacga ta    152

<210> SEQ ID NO 406
<211> LENGTH: 152
<212> TYPE: DNA
<213> ORGANISM: Artificial Sequence
<220> FEATURE:
<223> OTHER INFORMATION: target_10X_oligo_265

<400> SEQUENCE: 406
gaatcctagt acaagtggcc ggtctcagct gcgcaggatt gtggaacccg aagtatacgc    60
cgcctttctg gctttgaccg accctggcgg ccgcttcctg aaagtgtcac cttcagaaga    120
tgtgctgaga ccgacatcca atccggacga ta    152

<210> SEQ ID NO 407
<211> LENGTH: 152
<212> TYPE: DNA
<213> ORGANISM: Artificial Sequence
<220> FEATURE:
<223> OTHER INFORMATION: target_10X_oligo_266

<400> SEQUENCE: 407
gaatcctagt acaagtggcc ggtctcgatt gtggaacccg aagtatacgc cgcctttctg    60
gctttgaccg accctggcgg ccgcttcctg aaagtgtcac cttcagaaga tgtgctgccc    120
gcggacgaga ccgacatcca atccggacga ta    152

<210> SEQ ID NO 408
<211> LENGTH: 152
<212> TYPE: DNA
<213> ORGANISM: Artificial Sequence
<220> FEATURE:
<223> OTHER INFORMATION: target_10X_oligo_267

<400> SEQUENCE: 408
gaatcctagt acaagtggcc ggtctccccg aagtatacgc cgcctttctg gctttgaccg    60
accctggcgg ccgcttcctg aaagtgtcac cttcagaaga tgtgctgccc gcggacgaaa    120
acagacgaga ccgacatcca atccggacga ta    152

<210> SEQ ID NO 409
<211> LENGTH: 152
<212> TYPE: DNA
<213> ORGANISM: Artificial Sequence
<220> FEATURE:
<223> OTHER INFORMATION: target_10X_oligo_268

<400> SEQUENCE: 409
gaatcctagt acaagtggcc ggtctcacgc cgcctttctg gctttgaccg accctggcgg    60
ccgcttcctg aaagtgtcac cttcagaaga tgtgctgccc gcggacgaaa acagacatat    120
cgtgctgaga ccgacatcca atccggacga ta    152

<210> SEQ ID NO 410
<211> LENGTH: 152
<212> TYPE: DNA
<213> ORGANISM: Artificial Sequence
<220> FEATURE:
<223> OTHER INFORMATION: target_10X_oligo_269

<400> SEQUENCE: 410
gaatcctagt acaagtggcc ggtctctctg gctttgaccg accctggcgg ccgcttcctg    60
aaagtgtcac cttcagaaga tgtgctgccc gcggacgaaa acagacatat cgtgctgtca    120
gatagagaga ccgacatcca atccggacga ta    152

<210> SEQ ID NO 411
<211> LENGTH: 152
<212> TYPE: DNA
<213> ORGANISM: Artificial Sequence
<220> FEATURE:
<223> OTHER INFORMATION: target_10X_oligo_270

<400> SEQUENCE: 411
gaatcctagt acaagtggcc ggtctcaccg accctggcgg ccgcttcctg aaagtgtcac    60
cttcagaaga tgtgctgccc gcggacgaaa acagacatat cgtgctgtca gatagagtcc    120
tggggcgaga ccgacatcca atccggacga ta    152

<210> SEQ ID NO 412
<211> LENGTH: 152
<212> TYPE: DNA
<213> ORGANISM: Artificial Sequence
<220> FEATURE:
<223> OTHER INFORMATION: target_10X_oligo_271

<400> SEQUENCE: 412
gaatcctagt acaagtggcc ggtctcgcgg ccgcttcctg aaagtgtcac cttcagaaga    60
tgtgctgccc gcggacgaaa acagacatat cgtgctgtca gatagagtcc tggggccacg    120
ggacaggaga ccgacatcca atccggacga ta    152

<210> SEQ ID NO 413
<211> LENGTH: 152
<212> TYPE: DNA
<213> ORGANISM: Artificial Sequence
<220> FEATURE:
<223> OTHER INFORMATION: target_10X_oligo_272

<400> SEQUENCE: 413
gaatcctagt acaagtggcc ggtctccctg aaagtgtcac cttcagaaga tgtgctgccc    60
gcggacgaaa acagacatat cgtgctgtca gatagagtcc tggggccacg ggacagagtg    120
aagctggaga ccgacatcca atccggacga ta    152

<210> SEQ ID NO 414
<211> LENGTH: 152
<212> TYPE: DNA
<213> ORGANISM: Artificial Sequence
<220> FEATURE:
<223> OTHER INFORMATION: target_10X_oligo_273

<400> SEQUENCE: 414
gaatcctagt acaagtggcc ggtctctcac cttcagaaga tgtgctgccc gcggacgaaa      60
acagacatat cgtgctgtca gatagagtcc tggggccacg ggacagagtg aagctgttcc     120
cagacggaga ccgacatcca atccggacga ta                                    152

<210> SEQ ID NO 415
<211> LENGTH: 152
<212> TYPE: DNA
<213> ORGANISM: Artificial Sequence
<220> FEATURE:
<223> OTHER INFORMATION: target_10X_oligo_274

<400> SEQUENCE: 415
gaatcctagt acaagtggcc ggtctcaaga tgtgctgccc gcggacgaaa acagacatat      60
cgtgctgtca gatagagtcc tggggccacg ggacagagtg aagctgttcc cagacgaccg     120
gggaaggaga ccgacatcca atccggacga ta                                    152

<210> SEQ ID NO 416
<211> LENGTH: 152
<212> TYPE: DNA
<213> ORGANISM: Artificial Sequence
<220> FEATURE:
<223> OTHER INFORMATION: target_10X_oligo_275

<400> SEQUENCE: 416
gaatcctagt acaagtggcc ggtctcgccc gcggacgaaa acagacatat cgtgctgtca      60
gatagagtcc tggggccacg ggacagagtg aagctgttcc cagacgaccg gggaagtata     120
agggtggaga ccgacatcca atccggacga ta                                    152

<210> SEQ ID NO 417
<211> LENGTH: 152
<212> TYPE: DNA
<213> ORGANISM: Artificial Sequence
<220> FEATURE:
<223> OTHER INFORMATION: target_10X_oligo_276

<400> SEQUENCE: 417
gaatcctagt acaagtggcc ggtctcgaaa acagacatat cgtgctgtca gatagagtcc      60
tggggccacg ggacagagtg aagctgttcc cagacgaccg gggaagtata agggtgcgag     120
ggggtggaga ccgacatcca atccggacga ta                                    152

<210> SEQ ID NO 418
<211> LENGTH: 152
<212> TYPE: DNA
<213> ORGANISM: Artificial Sequence
<220> FEATURE:
<223> OTHER INFORMATION: target_10X_oligo_277

<400> SEQUENCE: 418
gaatcctagt acaagtggcc ggtctcatat cgtgctgtca gatagagtcc tggggccacg      60
ggacagagtg aagctgttcc cagacgaccg gggaagtata agggtgcgag ggggtgcggc     120
gtatatgaga ccgacatcca atccggacga ta                                    152

<210> SEQ ID NO 419
<211> LENGTH: 152
<212> TYPE: DNA
<213> ORGANISM: Artificial Sequence
<220> FEATURE:
<223> OTHER INFORMATION: target_10X_oligo_278

<400> SEQUENCE: 419

```
gaatcctagt acaagtggcc ggtctcgtca gatagagtcc tggggccacg ggacagagtg      60
aagctgttcc cagacgaccg gggaagtata agggtgcgag ggggtgcggc gtatattgct     120
agcttcgaga ccgacatcca atccggacga ta                                   152
```

<210> SEQ ID NO 420
<211> LENGTH: 152
<212> TYPE: DNA
<213> ORGANISM: Artificial Sequence
<220> FEATURE:
<223> OTHER INFORMATION: target_10X_oligo_279

<400> SEQUENCE: 420

```
gaatcctagt acaagtggcc ggtctcgtcc tggggccacg ggacagagtg aagctgttcc      60
cagacgaccg gggaagtata agggtgcgag ggggtgcggc gtatattgct agcttccacc     120
acgctcgaga ccgacatcca atccggacga ta                                   152
```

<210> SEQ ID NO 421
<211> LENGTH: 152
<212> TYPE: DNA
<213> ORGANISM: Artificial Sequence
<220> FEATURE:
<223> OTHER INFORMATION: target_10X_oligo_280

<400> SEQUENCE: 421

```
gaatcctagt acaagtggcc ggtctccacg ggacagagtg aagctgttcc cagacgaccg      60
gggaagtata agggtgcgag ggggtgcggc gtatattgct agcttccacc acgctcgcgt     120
gtttaggaga ccgacatcca atccggacga ta                                   152
```

<210> SEQ ID NO 422
<211> LENGTH: 152
<212> TYPE: DNA
<213> ORGANISM: Artificial Sequence
<220> FEATURE:
<223> OTHER INFORMATION: target_10X_oligo_281

<400> SEQUENCE: 422

```
gaatcctagt acaagtggcc ggtctcagtg aagctgttcc cagacgaccg gggaagtata      60
agggtgcgag ggggtgcggc gtatattgct agcttccacc acgctcgcgt gtttaggtgg     120
ggaagcgaga ccgacatcca atccggacga ta                                   152
```

<210> SEQ ID NO 423
<211> LENGTH: 152
<212> TYPE: DNA
<213> ORGANISM: Artificial Sequence
<220> FEATURE:
<223> OTHER INFORMATION: target_10X_oligo_282

<400> SEQUENCE: 423

```
gaatcctagt acaagtggcc ggtctcttcc cagacgaccg gggaagtata agggtgcgag      60
ggggtgcggc gtatattgct agcttccacc acgctcgcgt gtttaggtgg ggaagctctc     120
acagccgaga ccgacatcca atccggacga ta                                   152
```

<210> SEQ ID NO 424
<211> LENGTH: 152
<212> TYPE: DNA
<213> ORGANISM: Artificial Sequence
<220> FEATURE:
<223> OTHER INFORMATION: target_10X_oligo_283

<400> SEQUENCE: 424
gaatcctagt acaagtggcc ggtctcaccg gggaagtata agggtgcgag ggggtgcggc    60
gtatattgct agcttccacc acgctcgcgt gtttaggtgg ggaagctctc acagcccctc   120
atttgcgaga ccgacatcca atccggacga ta                                 152

<210> SEQ ID NO 425
<211> LENGTH: 152
<212> TYPE: DNA
<213> ORGANISM: Artificial Sequence
<220> FEATURE:
<223> OTHER INFORMATION: target_10X_oligo_284

<400> SEQUENCE: 425
gaatcctagt acaagtggcc ggtctctata agggtgcgag ggggtgcggc gtatattgct    60
agcttccacc acgctcgcgt gtttaggtgg ggaagctctc acagcccctc atttgccctg   120
ctgcgcgaga ccgacatcca atccggacga ta                                 152

<210> SEQ ID NO 426
<211> LENGTH: 152
<212> TYPE: DNA
<213> ORGANISM: Artificial Sequence
<220> FEATURE:
<223> OTHER INFORMATION: target_10X_oligo_285

<400> SEQUENCE: 426
gaatcctagt acaagtggcc ggtctccgag ggggtgcggc gtatattgct agcttccacc    60
acgctcgcgt gtttaggtgg ggaagctctc acagcccctc atttgccctg ctgcgcgtca   120
gtcttggaga ccgacatcca atccggacga ta                                 152

<210> SEQ ID NO 427
<211> LENGTH: 152
<212> TYPE: DNA
<213> ORGANISM: Artificial Sequence
<220> FEATURE:
<223> OTHER INFORMATION: target_10X_oligo_286

<400> SEQUENCE: 427
gaatcctagt acaagtggcc ggtctccggc gtatattgct agcttccacc acgctcgcgt    60
gtttaggtgg ggaagctctc acagcccctc atttgccctg ctgcgcgtca gtcttgcaga   120
tcttgcgaga ccgacatcca atccggacga ta                                 152

<210> SEQ ID NO 428
<211> LENGTH: 152
<212> TYPE: DNA
<213> ORGANISM: Artificial Sequence
<220> FEATURE:
<223> OTHER INFORMATION: target_10X_oligo_287

<400> SEQUENCE: 428
gaatcctagt acaagtggcc ggtctctgct agcttccacc acgctcgcgt gtttaggtgg    60
ggaagctctc acagcccctc atttgccctg ctgcgcgtca gtcttgcaga tcttgcggta   120
gccggagaga ccgacatcca atccggacga ta                                 152

<210> SEQ ID NO 429
<211> LENGTH: 152
<212> TYPE: DNA
<213> ORGANISM: Artificial Sequence
<220> FEATURE:
<223> OTHER INFORMATION: target_10X_oligo_288

<400> SEQUENCE: 429
gaatcctagt acaagtggcc ggtctccacc acgctcgcgt gtttaggtgg ggaagctctc    60
acagcccctc atttgccctg ctgcgcgtca gtcttgcaga tcttgcggta gccggactgt   120
tgaggggaga ccgacatcca atccggacga ta                                 152

<210> SEQ ID NO 430
<211> LENGTH: 152
<212> TYPE: DNA
<213> ORGANISM: Artificial Sequence
<220> FEATURE:
<223> OTHER INFORMATION: target_10X_oligo_289

<400> SEQUENCE: 430
gaatcctagt acaagtggcc ggtctcgcgt gtttaggtgg ggaagctctc acagcccctc    60
atttgccctg ctgcgcgtca gtcttgcaga tcttgcggta gccggactgt tgagggatgg   120
ggtggagaga ccgacatcca atccggacga ta                                 152

<210> SEQ ID NO 431
<211> LENGTH: 152
<212> TYPE: DNA
<213> ORGANISM: Artificial Sequence
<220> FEATURE:
<223> OTHER INFORMATION: target_10X_oligo_290

<400> SEQUENCE: 431
gaatcctagt acaagtggcc ggtctcgtgg ggaagctctc acagcccctc atttgccctg    60
ctgcgcgtca gtcttgcaga tcttgcggta gccggactgt tgagggatgg ggtggacgtc   120
ttcactgaga ccgacatcca atccggacga ta                                 152

<210> SEQ ID NO 432
<211> LENGTH: 152
<212> TYPE: DNA
<213> ORGANISM: Artificial Sequence
<220> FEATURE:
<223> OTHER INFORMATION: target_10X_oligo_291

<400> SEQUENCE: 432
gaatcctagt acaagtggcc ggtctctctc acagcccctc atttgccctg ctgcgcgtca    60
gtcttgcaga tcttgcggta gccggactgt tgagggatgg ggtggacgtc ttcactgccg   120
aactccgaga ccgacatcca atccggacga ta                                 152

<210> SEQ ID NO 433
<211> LENGTH: 152
<212> TYPE: DNA
<213> ORGANISM: Artificial Sequence
<220> FEATURE:
<223> OTHER INFORMATION: target_10X_oligo_292

<400> SEQUENCE: 433
gaatcctagt acaagtggcc ggtctccctc atttgccctg ctgcgcgtca gtcttgcaga    60
tcttgcggta gccggactgt tgagggatgg ggtggacgtc ttcactgccg aactccctcc   120
ttggacgaga ccgacatcca atccggacga ta                                 152

<210> SEQ ID NO 434
<211> LENGTH: 152
<212> TYPE: DNA
<213> ORGANISM: Artificial Sequence
<220> FEATURE:

<223> OTHER INFORMATION: target_10X_oligo_293

<400> SEQUENCE: 434
gaatcctagt acaagtggcc ggtctccctg ctgcgcgtca gtcttgcaga tcttgcggta     60
gccggactgt tgagggatgg ggtggacgtc ttcactgccg aactccctcc ttggacacct    120
gcctgggaga ccgacatcca atccggacga ta                                 152

<210> SEQ ID NO 435
<211> LENGTH: 152
<212> TYPE: DNA
<213> ORGANISM: Artificial Sequence
<220> FEATURE:
<223> OTHER INFORMATION: target_10X_oligo_294

<400> SEQUENCE: 435
gaatcctagt acaagtggcc ggtctcgtca gtcttgcaga tcttgcggta gccggactgt     60
tgagggatgg ggtggacgtc ttcactgccg aactccctcc ttggacacct gcctggaggt    120
atgcgtgaga ccgacatcca atccggacga ta                                 152

<210> SEQ ID NO 436
<211> LENGTH: 152
<212> TYPE: DNA
<213> ORGANISM: Artificial Sequence
<220> FEATURE:
<223> OTHER INFORMATION: target_10X_oligo_295

<400> SEQUENCE: 436
gaatcctagt acaagtggcc ggtctccaga tcttgcggta gccggactgt tgagggatgg     60
ggtggacgtc ttcactgccg aactccctcc ttggacacct gcctggaggt atgcgtcaat    120
cgctctgaga ccgacatcca atccggacga ta                                 152

<210> SEQ ID NO 437
<211> LENGTH: 152
<212> TYPE: DNA
<213> ORGANISM: Artificial Sequence
<220> FEATURE:
<223> OTHER INFORMATION: target_10X_oligo_296

<400> SEQUENCE: 437
gaatcctagt acaagtggcc ggtctcggta gccggactgt tgagggatgg ggtggacgtc     60
ttcactgccg aactccctcc ttggacacct gcctggaggt atgcgtcaat cgctctggtc    120
aaagcggaga ccgacatcca atccggacga ta                                 152

<210> SEQ ID NO 438
<211> LENGTH: 152
<212> TYPE: DNA
<213> ORGANISM: Artificial Sequence
<220> FEATURE:
<223> OTHER INFORMATION: target_10X_oligo_297

<400> SEQUENCE: 438
gaatcctagt acaagtggcc ggtctcctgt tgagggatgg ggtggacgtc ttcactgccg     60
aactccctcc ttggacacct gcctggaggt atgcgtcaat cgctctggtc aaagcggtcg    120
agagtggaga ccgacatcca atccggacga ta                                 152

<210> SEQ ID NO 439
<211> LENGTH: 152
<212> TYPE: DNA
<213> ORGANISM: Artificial Sequence
<220> FEATURE:
<223> OTHER INFORMATION: target_10X_oligo_298

<400> SEQUENCE: 439
gaatcctagt acaagtggcc ggtctcatgg ggtggacgtc ttcactgccg aactccctcc    60
ttggacacct gcctggaggt atgcgtcaat cgctctggtc aaagcggtcg agagtggcga   120
tgctaagaga ccgacatcca atccggacga ta    152

<210> SEQ ID NO 440
<211> LENGTH: 152
<212> TYPE: DNA
<213> ORGANISM: Artificial Sequence
<220> FEATURE:
<223> OTHER INFORMATION: target_10X_oligo_299

<400> SEQUENCE: 440
gaatcctagt acaagtggcc ggtctccgtc ttcactgccg aactccctcc ttggacacct    60
gcctggaggt atgcgtcaat cgctctggtc aaagcggtcg agagtggcga tgctaaacag   120
gttggcgaga ccgacatcca atccggacga ta    152

<210> SEQ ID NO 441
<211> LENGTH: 152
<212> TYPE: DNA
<213> ORGANISM: Artificial Sequence
<220> FEATURE:
<223> OTHER INFORMATION: target_10X_oligo_300

<400> SEQUENCE: 441
gaatcctagt acaagtggcc ggtctcgccg aactccctcc ttggacacct gcctggaggt    60
atgcgtcaat cgctctggtc aaagcggtcg agagtggcga tgctaaacag gttggctggt   120
tggtccgaga ccgacatcca atccggacga ta    152

<210> SEQ ID NO 442
<211> LENGTH: 152
<212> TYPE: DNA
<213> ORGANISM: Artificial Sequence
<220> FEATURE:
<223> OTHER INFORMATION: target_10X_oligo_301

<400> SEQUENCE: 442
gaatcctagt acaagtggcc ggtctcctcc ttggacacct gcctggaggt atgcgtcaat    60
cgctctggtc aaagcggtcg agagtggcga tgctaaacag gttggctggt tggtccctgg   120
cgacgagaga ccgacatcca atccggacga ta    152

<210> SEQ ID NO 443
<211> LENGTH: 152
<212> TYPE: DNA
<213> ORGANISM: Artificial Sequence
<220> FEATURE:
<223> OTHER INFORMATION: target_10X_oligo_302

<400> SEQUENCE: 443
gaatcctagt acaagtggcc ggtctcacct gcctggaggt atgcgtcaat cgctctggtc    60
aaagcggtcg agagtggcga tgctaaacag gttggctggt tggtccctgg cgacgagctg   120
gacttcgaga ccgacatcca atccggacga ta    152

<210> SEQ ID NO 444
<211> LENGTH: 152
<212> TYPE: DNA

```
<213> ORGANISM: Artificial Sequence
<220> FEATURE:
<223> OTHER INFORMATION: target_10X_oligo_303

<400> SEQUENCE: 444
gaatcctagt acaagtggcc ggtctcaggt atgcgtcaat cgctctggtc aaagcggtcg      60
agagtggcga tgctaaacag gttggctggt tggtccctgg cgacgagctg gacttcgggc     120
ctgaaggaga ccgacatcca atccggacga ta                                   152

<210> SEQ ID NO 445
<211> LENGTH: 152
<212> TYPE: DNA
<213> ORGANISM: Artificial Sequence
<220> FEATURE:
<223> OTHER INFORMATION: target_10X_oligo_304

<400> SEQUENCE: 445
gaatcctagt acaagtggcc ggtctccaat cgctctggtc aaagcggtcg agagtggcga      60
tgctaaacag gttggctggt tggtccctgg cgacgagctg gacttcgggc ctgaaggggt     120
caccacgaga ccgacatcca atccggacga ta                                   152

<210> SEQ ID NO 446
<211> LENGTH: 152
<212> TYPE: DNA
<213> ORGANISM: Artificial Sequence
<220> FEATURE:
<223> OTHER INFORMATION: target_10X_oligo_305

<400> SEQUENCE: 446
gaatcctagt acaagtggcc ggtctcggtc aaagcggtcg agagtggcga tgctaaacag      60
gttggctggt tggtccctgg cgacgagctg gacttcgggc ctgaaggggt caccacagcg     120
gcgggcgaga ccgacatcca atccggacga ta                                   152

<210> SEQ ID NO 447
<211> LENGTH: 152
<212> TYPE: DNA
<213> ORGANISM: Artificial Sequence
<220> FEATURE:
<223> OTHER INFORMATION: target_10X_oligo_306

<400> SEQUENCE: 447
gaatcctagt acaagtggcc ggtctcgtcg agagtggcga tgctaaacag gttggctggt      60
tggtccctgg cgacgagctg gacttcgggc ctgaaggggt caccacagcg gcgggcgacc     120
tcagtagaga ccgacatcca atccggacga ta                                   152

<210> SEQ ID NO 448
<211> LENGTH: 152
<212> TYPE: DNA
<213> ORGANISM: Artificial Sequence
<220> FEATURE:
<223> OTHER INFORMATION: target_10X_oligo_307

<400> SEQUENCE: 448
gaatcctagt acaagtggcc ggtctcgcga tgctaaacag gttggctggt tggtccctgg      60
cgacgagctg gacttcgggc ctgaaggggt caccacagcg gcgggcgacc tcagtatgtt     120
cttgaagaga ccgacatcca atccggacga ta                                   152

<210> SEQ ID NO 449
<211> LENGTH: 152
```

```
<212> TYPE: DNA
<213> ORGANISM: Artificial Sequence
<220> FEATURE:
<223> OTHER INFORMATION: target_10X_oligo_308

<400> SEQUENCE: 449
gaatcctagt acaagtggcc ggtctcacag gttggctggt tggtccctgg cgacgagctg      60
gacttcgggc ctgaagggg caccacagcg gcgggcgacc tcagtatgtt cttgaaatat     120
tttccagaga ccgacatcca atccggacga ta                                   152

<210> SEQ ID NO 450
<211> LENGTH: 152
<212> TYPE: DNA
<213> ORGANISM: Artificial Sequence
<220> FEATURE:
<223> OTHER INFORMATION: target_10X_oligo_309

<400> SEQUENCE: 450
gaatcctagt acaagtggcc ggtctctggt tggtccctgg cgacgagctg gacttcgggc      60 ctgaagggg caccacagcg gcgggcgacc tcagtatgtt cttgaaatat tttccagagc     120
gccactgaga ccgacatcca atccggacga ta                                   152

<210> SEQ ID NO 451
<211> LENGTH: 152
<212> TYPE: DNA
<213> ORGANISM: Artificial Sequence
<220> FEATURE:
<223> OTHER INFORMATION: target_10X_oligo_310

<400> SEQUENCE: 451
gaatcctagt acaagtggcc ggtctcctgg cgacgagctg gacttcgggc ctgaagggg t     60 caccacagcg gcgggcgacc tcagtatgtt cttgaaatat tttccagagc gccactgggt    120
tgttacgaga ccgacatcca atccggacga ta                                   152

<210> SEQ ID NO 452
<211> LENGTH: 152
<212> TYPE: DNA
<213> ORGANISM: Artificial Sequence
<220> FEATURE:
<223> OTHER INFORMATION: target_10X_oligo_311

<400> SEQUENCE: 452
gaatcctagt acaagtggcc ggtctcgctg gacttcgggc ctgaagggg t caccacagcg      60 gcgggcgacc tcagtatgtt cttgaaatat tttccagagc gccactgggt tgttacagga    120
tttgaagaga ccgacatcca atccggacga ta                                   152

<210> SEQ ID NO 453
<211> LENGTH: 152
<212> TYPE: DNA
<213> ORGANISM: Artificial Sequence
<220> FEATURE:
<223> OTHER INFORMATION: target_10X_oligo_312

<400> SEQUENCE: 453
gaatcctagt acaagtggcc ggtctcgggc ctgaagggg t caccacagcg gcgggcgacc      60
tcagtatgtt cttgaaatat tttccagagc gccactgggt tgttacagga tttgaagacg    120
ataagagaga ccgacatcca atccggacga ta                                   152

<210> SEQ ID NO 454
```

```
<211> LENGTH: 152
<212> TYPE: DNA
<213> ORGANISM: Artificial Sequence
<220> FEATURE:
<223> OTHER INFORMATION: target_10X_oligo_313

<400> SEQUENCE: 454
gaatcctagt acaagtggcc ggtctcgggt caccacagcg gcgggcgacc tcagtatgtt      60
cttgaaatat tttccagagc gccactgggt tgttacagga tttgaagacg ataagagaat     120
caacctgaga ccgacatcca atccggacga ta                                   152

<210> SEQ ID NO 455
<211> LENGTH: 152
<212> TYPE: DNA
<213> ORGANISM: Artificial Sequence
<220> FEATURE:
<223> OTHER INFORMATION: target_10X_oligo_314

<400> SEQUENCE: 455
gaatcctagt acaagtggcc ggtctcagcg gcgggcgacc tcagtatgtt cttgaaatat      60
tttccagagc gccactgggt tgttacagga tttgaagacg ataagagaat caaccttaag     120
cccgccgaga ccgacatcca atccggacga ta                                   152

<210> SEQ ID NO 456
<211> LENGTH: 152
<212> TYPE: DNA
<213> ORGANISM: Artificial Sequence
<220> FEATURE:
<223> OTHER INFORMATION: target_10X_oligo_315

<400> SEQUENCE: 456
gaatcctagt acaagtggcc ggtctcgacc tcagtatgtt cttgaaatat tttccagagc      60
gccactgggt tgttacagga tttgaagacg ataagagaat caaccttaag cccgccttcc     120
tctctggaga ccgacatcca atccggacga ta                                   152

<210> SEQ ID NO 457
<211> LENGTH: 152
<212> TYPE: DNA
<213> ORGANISM: Artificial Sequence
<220> FEATURE:
<223> OTHER INFORMATION: target_10X_oligo_316

<400> SEQUENCE: 457
gaatcctagt acaagtggcc ggtctctgtt cttgaaatat tttccagagc gccactgggt      60
tgttacagga tttgaagacg ataagagaat caaccttaag cccgccttcc tctctgctga     120
acaggcgaga ccgacatcca atccggacga ta                                   152

<210> SEQ ID NO 458
<211> LENGTH: 152
<212> TYPE: DNA
<213> ORGANISM: Artificial Sequence
<220> FEATURE:
<223> OTHER INFORMATION: target_10X_oligo_317

<400> SEQUENCE: 458
gaatcctagt acaagtggcc ggtctcatat tttccagagc gccactgggt tgttacagga      60
tttgaagacg ataagagaat caaccttaag cccgccttcc tctctgctga acaggcagag     120
gtgctggaga ccgacatcca atccggacga ta                                   152
```

```
<210> SEQ ID NO 459
<211> LENGTH: 152
<212> TYPE: DNA
<213> ORGANISM: Artificial Sequence
<220> FEATURE:
<223> OTHER INFORMATION: target_10X_oligo_318

<400> SEQUENCE: 459
gaatcctagt acaagtggcc ggtctcgagc gccactgggt tgttacagga tttgaagacg    60
ataagagaat caaccttaag cccgccttcc tctctgctga acaggcagag gtgctgcgca   120
ccgagcgaga ccgacatcca atccggacga ta                                 152

<210> SEQ ID NO 460
<211> LENGTH: 152
<212> TYPE: DNA
<213> ORGANISM: Artificial Sequence
<220> FEATURE:
<223> OTHER INFORMATION: target_10X_oligo_319

<400> SEQUENCE: 460
gaatcctagt acaagtggcc ggtctcgggt tgttacagga tttgaagacg ataagagaat    60
caaccttaag cccgccttcc tctctgctga acaggcagag gtgctgcgca ccgagcgcag   120
tgaccggaga ccgacatcca atccggacga ta                                 152

<210> SEQ ID NO 461
<211> LENGTH: 152
<212> TYPE: DNA
<213> ORGANISM: Artificial Sequence
<220> FEATURE:
<223> OTHER INFORMATION: target_10X_oligo_320

<400> SEQUENCE: 461
gaatcctagt acaagtggcc ggtctcagga tttgaagacg ataagagaat caaccttaag    60
cccgccttcc tctctgctga acaggcagag gtgctgcgca ccgagcgcag tgaccggccg   120
gacaccgaga ccgacatcca atccggacga ta                                 152

<210> SEQ ID NO 462
<211> LENGTH: 152
<212> TYPE: DNA
<213> ORGANISM: Artificial Sequence
<220> FEATURE:
<223> OTHER INFORMATION: target_10X_oligo_321

<400> SEQUENCE: 462
gaatcctagt acaagtggcc ggtctcgacg ataagagaat caaccttaag cccgccttcc    60
tctctgctga acaggcagag gtgctgcgca ccgagcgcag tgaccggccg gacaccctga   120
ccgagggaga ccgacatcca atccggacga ta                                 152

<210> SEQ ID NO 463
<211> LENGTH: 152
<212> TYPE: DNA
<213> ORGANISM: Artificial Sequence
<220> FEATURE:
<223> OTHER INFORMATION: target_10X_oligo_322

<400> SEQUENCE: 463
gaatcctagt acaagtggcc ggtctcgaat caaccttaag cccgccttcc tctctgctga    60
acaggcagag gtgctgcgca ccgagcgcag tgaccggccg gacaccctga ccgaggctgg   120
agagatgaga ccgacatcca atccggacga ta                                 152
```

<210> SEQ ID NO 464
<211> LENGTH: 152
<212> TYPE: DNA
<213> ORGANISM: Artificial Sequence
<220> FEATURE:
<223> OTHER INFORMATION: target_10X_oligo_323

<400> SEQUENCE: 464

```
gaatcctagt acaagtggcc ggtctctaag cccgccttcc tctctgctga acaggcagag      60
gtgctgcgca ccgagcgcag tgaccggccg gacaccctga ccgaggctgg agagatactc     120
gcccaagaga ccgacatcca atccggacga ta                                   152
```

<210> SEQ ID NO 465
<211> LENGTH: 152
<212> TYPE: DNA
<213> ORGANISM: Artificial Sequence
<220> FEATURE:
<223> OTHER INFORMATION: target_10X_oligo_324

<400> SEQUENCE: 465

```
gaatcctagt acaagtggcc ggtctcttcc tctctgctga acaggcagag gtgctgcgca      60
ccgagcgcag tgaccggccg gacaccctga ccgaggctgg agagatactc gcccaatttt     120
tcccccgaga ccgacatcca atccggacga ta                                   152
```

<210> SEQ ID NO 466
<211> LENGTH: 152
<212> TYPE: DNA
<213> ORGANISM: Artificial Sequence
<220> FEATURE:
<223> OTHER INFORMATION: target_10X_oligo_325

<400> SEQUENCE: 466

```
gaatcctagt acaagtggcc ggtctcctga acaggcagag gtgctgcgca ccgagcgcag      60
tgaccggccg gacaccctga ccgaggctgg agagatactc gcccaatttt tcccccgctg     120
ttggaggaga ccgacatcca atccggacga ta                                   152
```

<210> SEQ ID NO 467
<211> LENGTH: 152
<212> TYPE: DNA
<213> ORGANISM: Artificial Sequence
<220> FEATURE:
<223> OTHER INFORMATION: target_10X_oligo_326

<400> SEQUENCE: 467

```
gaatcctagt acaagtggcc ggtctcagag gtgctgcgca ccgagcgcag tgaccggccg      60
gacaccctga ccgaggctgg agagatactc gcccaatttt tcccccgctg ttggagagca     120
accgtcgaga ccgacatcca atccggacga ta                                   152
```

<210> SEQ ID NO 468
<211> LENGTH: 152
<212> TYPE: DNA
<213> ORGANISM: Artificial Sequence
<220> FEATURE:
<223> OTHER INFORMATION: target_10X_oligo_327

<400> SEQUENCE: 468

```
gaatcctagt acaagtggcc ggtctccgca ccgagcgcag tgaccggccg gacaccctga      60
ccgaggctgg agagatactc gcccaatttt tcccccgctg ttggagagca accgtcgcca     120
aggtgcgaga ccgacatcca atccggacga ta                                   152
```

<210> SEQ ID NO 469
<211> LENGTH: 152
<212> TYPE: DNA
<213> ORGANISM: Artificial Sequence
<220> FEATURE:
<223> OTHER INFORMATION: target_10X_oligo_328

<400> SEQUENCE: 469

```
gaatcctagt acaagtggcc ggtctcgcag tgaccggccg gacaccctga ccgaggctgg    60
agagatactc gcccaatttt tcccccgctg ttggagagca accgtcgcca aggtgctctg   120
tcacccgaga ccgacatcca atccggacga ta                                 152
```

<210> SEQ ID NO 470
<211> LENGTH: 152
<212> TYPE: DNA
<213> ORGANISM: Artificial Sequence
<220> FEATURE:
<223> OTHER INFORMATION: target_10X_oligo_329

<400> SEQUENCE: 470

```
gaatcctagt acaagtggcc ggtctcgccg gacaccctga ccgaggctgg agagatactc    60
gcccaatttt tcccccgctg ttggagagca accgtcgcca aggtgctctg tcacccggga   120
ctgacggaga ccgacatcca atccggacga ta                                 152
```

<210> SEQ ID NO 471
<211> LENGTH: 152
<212> TYPE: DNA
<213> ORGANISM: Artificial Sequence
<220> FEATURE:
<223> OTHER INFORMATION: target_10X_oligo_330

<400> SEQUENCE: 471

```
gaatcctagt acaagtggcc ggtctcctga ccgaggctgg agagatactc gcccaatttt    60
tcccccgctg ttggagagca accgtcgcca aggtgctctg tcacccggga ctgacggtta   120
ttagaagaga ccgacatcca atccggacga ta                                 152
```

<210> SEQ ID NO 472
<211> LENGTH: 152
<212> TYPE: DNA
<213> ORGANISM: Artificial Sequence
<220> FEATURE:
<223> OTHER INFORMATION: target_10X_oligo_331

<400> SEQUENCE: 472

```
gaatcctagt acaagtggcc ggtctcctgg agagatactc gcccaatttt tcccccgctg    60
ttggagagca accgtcgcca aggtgctctg tcacccggga ctgacggtta ttagaagaac   120
agccctgaga ccgacatcca atccggacga ta                                 152
```

<210> SEQ ID NO 473
<211> LENGTH: 152
<212> TYPE: DNA
<213> ORGANISM: Artificial Sequence
<220> FEATURE:
<223> OTHER INFORMATION: target_10X_oligo_332

<400> SEQUENCE: 473

```
gaatcctagt acaagtggcc ggtctcactc gcccaatttt tcccccgctg ttggagagca    60
accgtcgcca aggtgctctg tcacccggga ctgacggtta ttagaagaac agcccttggc   120
```

```
cagccagaga ccgacatcca atccggacga ta                                    152

<210> SEQ ID NO 474
<211> LENGTH: 152
<212> TYPE: DNA
<213> ORGANISM: Artificial Sequence
<220> FEATURE:
<223> OTHER INFORMATION: target_10X_oligo_333

<400> SEQUENCE: 474
gaatcctagt acaagtggcc ggtctctttt tcccccgctg ttggagagca accgtcgcca       60
aggtgctctg tcacccggga ctgacggtta ttagaagaac agcccttggc cagccaaggt      120
ggcgaagaga ccgacatcca atccggacga ta                                    152

<210> SEQ ID NO 475
<211> LENGTH: 152
<212> TYPE: DNA
<213> ORGANISM: Artificial Sequence
<220> FEATURE:
<223> OTHER INFORMATION: target_10X_oligo_334

<400> SEQUENCE: 475
gaatcctagt acaagtggcc ggtctcgctg ttggagagca accgtcgcca aggtgctctg       60
tcacccggga ctgacggtta ttagaagaac agcccttggc cagccaaggt ggcgaagggg      120
tcacctgaga ccgacatcca atccggacga ta                                    152

<210> SEQ ID NO 476
<211> LENGTH: 152
<212> TYPE: DNA
<213> ORGANISM: Artificial Sequence
<220> FEATURE:
<223> OTHER INFORMATION: target_10X_oligo_335

<400> SEQUENCE: 476
gaatcctagt acaagtggcc ggtctcagca accgtcgcca aggtgctctg tcacccggga       60
ctgacggtta ttagaagaac agcccttggc cagccaaggt ggcgaagggg tcacctgcca      120
tatagcgaga ccgacatcca atccggacga ta                                    152

<210> SEQ ID NO 477
<211> LENGTH: 152
<212> TYPE: DNA
<213> ORGANISM: Artificial Sequence
<220> FEATURE:
<223> OTHER INFORMATION: target_10X_oligo_336

<400> SEQUENCE: 477
gaatcctagt acaagtggcc ggtctcgcca aggtgctctg tcacccggga ctgacggtta       60
ttagaagaac agcccttggc cagccaaggt ggcgaagggg tcacctgcca tatagctggc      120
gtccctgaga ccgacatcca atccggacga ta                                    152

<210> SEQ ID NO 478
<211> LENGTH: 152
<212> TYPE: DNA
<213> ORGANISM: Artificial Sequence
<220> FEATURE:
<223> OTHER INFORMATION: target_10X_oligo_337

<400> SEQUENCE: 478
gaatcctagt acaagtggcc ggtctctctg tcacccggga ctgacggtta ttagaagaac       60
agcccttggc cagccaaggt ggcgaagggg tcacctgcca tatagctggc gtccctggtc      120
```
agccgagaga ccgacatcca atccggacga ta           152

<210> SEQ ID NO 479
<211> LENGTH: 152
<212> TYPE: DNA
<213> ORGANISM: Artificial Sequence
<220> FEATURE:
<223> OTHER INFORMATION: target_10X_oligo_338

<400> SEQUENCE: 479
gaatcctagt acaagtggcc ggtctcggga ctgacggtta ttagaagaac agcccttggc           60
cagccaaggt ggcgaagggg tcacctgcca tatagctggc gtccctggtc agccgaccca          120
tggagcgaga ccgacatcca atccggacga ta           152

<210> SEQ ID NO 480
<211> LENGTH: 152
<212> TYPE: DNA
<213> ORGANISM: Artificial Sequence
<220> FEATURE:
<223> OTHER INFORMATION: target_10X_oligo_339

<400> SEQUENCE: 480
gaatcctagt acaagtggcc ggtctcgtta ttagaagaac agcccttggc cagccaaggt           60
ggcgaagggg tcacctgcca tatagctggc gtccctggtc agccgaccca tggagcggtg          120
gaacccgaga ccgacatcca atccggacga ta           152

<210> SEQ ID NO 481
<211> LENGTH: 152
<212> TYPE: DNA
<213> ORGANISM: Artificial Sequence
<220> FEATURE:
<223> OTHER INFORMATION: target_10X_oligo_340

<400> SEQUENCE: 481
gaatcctagt acaagtggcc ggtctcgaac agcccttggc cagccaaggt ggcgaagggg           60
tcacctgcca tatagctggc gtccctggtc agccgaccca tggagcggtg gaaccccaag         120
cagggcgaga ccgacatcca atccggacga ta           152

<210> SEQ ID NO 482
<211> LENGTH: 152
<212> TYPE: DNA
<213> ORGANISM: Artificial Sequence
<220> FEATURE:
<223> OTHER INFORMATION: target_10X_oligo_341

<400> SEQUENCE: 482
gaatcctagt acaagtggcc ggtctctggc cagccaaggt ggcgaagggg tcacctgcca           60
tatagctggc gtccctggtc agccgaccca tggagcggtg gaaccccaag cagggctgac          120
cccaaggaga ccgacatcca atccggacga ta           152

<210> SEQ ID NO 483
<211> LENGTH: 152
<212> TYPE: DNA

```
<213> ORGANISM: Artificial Sequence
<220> FEATURE:
<223> OTHER INFORMATION: target_10X_oligo_342

<400> SEQUENCE: 483
gaatcctagt acaagtggcc ggtctcaggt ggcgaagggg tcacctgcca tatagctggc    60
gtccctggtc agccgaccca tggagcggtg gaaccccaag cagggctgac cccaagaaga   120
agaggagaga ccgacatcca atccggacga ta                                 152

<210> SEQ ID NO 484
<211> LENGTH: 152
<212> TYPE: DNA
<213> ORGANISM: Artificial Sequence
<220> FEATURE:
<223> OTHER INFORMATION: target_10X_oligo_343

<400> SEQUENCE: 484
gaatcctagt acaagtggcc ggtctcgggg tcacctgcca tatagctggc gtccctggtc    60
agccgaccca tggagcggtg gaaccccaag cagggctgac cccaagaaga agaggaaggt   120
gaggtcgaga ccgacatcca atccggacga ta                                 152

<210> SEQ ID NO 485
<211> LENGTH: 152
<212> TYPE: DNA
<213> ORGANISM: Artificial Sequence
<220> FEATURE:
<223> OTHER INFORMATION: target_10X_oligo_344

<400> SEQUENCE: 485
gaatcctagt acaagtggcc ggtctcgcca tatagctggc gtccctggtc agccgaccca    60
tggagcggtg gaaccccaag cagggctgac cccaagaaga agaggaaggt gaggtccggc   120
ggcggagaga ccgacatcca atccggacga ta                                 152

<210> SEQ ID NO 486
<211> LENGTH: 152
<212> TYPE: DNA
<213> ORGANISM: Artificial Sequence
<220> FEATURE:
<223> OTHER INFORMATION: target_10X_oligo_345

<400> SEQUENCE: 486
gaatcctagt acaagtggcc ggtctctggc gtccctggtc agccgaccca tggagcggtg    60
gaaccccaag cagggctgac cccaagaaga agaggaaggt gaggtccggc ggcggagagg   120
gcagaggaga ccgacatcca atccggacga ta                                 152

<210> SEQ ID NO 487
<211> LENGTH: 152
<212> TYPE: DNA
<213> ORGANISM: Artificial Sequence
<220> FEATURE:
<223> OTHER INFORMATION: target_10X_oligo_346

<400> SEQUENCE: 487
gaatcctagt acaagtggcc ggtctcggtc agccgaccca tggagcggtg gaaccccaag    60
cagggctgac cccaagaaga agaggaaggt gaggtccggc ggcggagagg gcagaggaag   120
tcttctgaga ccgacatcca atccggacga ta                                 152
```